(12) United States Patent
Boyce et al.

(10) Patent No.: US 7,820,646 B2
(45) Date of Patent: Oct. 26, 2010

(54) CYCLIZED DERIVATIVES AS EG-5 INHIBITORS

(75) Inventors: Rustum Boyce, Singapore (SG); Eric Martin, El Cerrito, CA (US); Weibo Wang, Moraga, CA (US); Hong Yang, Fremont, CA (US); Paul A. Barsanti, Pleasant Hill, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 56 days.

(21) Appl. No.: 11/969,164

(22) Filed: Jan. 3, 2008

(65) Prior Publication Data
US 2008/0207589 A1  Aug. 28, 2008

Related U.S. Application Data

(60) Provisional application No. 60/883,740, filed on Jan. 5, 2007.

(51) Int. Cl.
C07D 403/06 (2006.01)
C07D 413/06 (2006.01)
A61K 31/422 (2006.01)
A61P 35/00 (2006.01)

(52) U.S. Cl. ............... 514/211.03; 514/218; 514/228.8; 514/230.8; 514/326; 514/376; 540/488; 540/492; 544/97; 544/139; 544/370; 548/231

(58) Field of Classification Search ............ 514/211.03, 514/218, 228.8, 230.8, 326, 376; 540/488, 540/492; 544/97, 139, 370; 548/231
See application file for complete search history.

(56) References Cited

U.S. PATENT DOCUMENTS

| | | | |
|---|---|---|---|
| 4,152,440 | A | 5/1979 | Gebert et al. |
| 4,235,871 | A | 11/1980 | Papahadjopoulos et al. |
| 4,501,728 | A | 2/1985 | Geho et al. |
| 4,837,028 | A | 6/1989 | Allen |
| 5,011,472 | A | 4/1991 | Aebischer et al. |
| 5,023,252 | A | 6/1991 | Hseih |
| 6,172,087 | B1 | 1/2001 | Steiner et al. |
| 6,271,241 | B1 | 8/2001 | DeSimone et al. |
| 6,545,004 | B1 | 4/2003 | Finer et al. |
| 6,562,831 | B1 | 5/2003 | Finer et al. |
| 6,630,479 | B1 | 10/2003 | Finer et al. |
| 7,291,641 | B2 | 11/2007 | Chabrier De Lassauniere et al. |
| 2004/0132788 | A1 | 7/2004 | Chabrier De Lassauniere et al. |
| 2005/0187277 | A1 | 8/2005 | Mjalli |
| 2005/0215546 | A1 | 9/2005 | Hurnaus et al. |
| 2005/0228002 | A1 | 10/2005 | Wang et al. |
| 2005/0261337 | A1 | 11/2005 | Wang et al. |
| 2006/0009472 | A1 | 1/2006 | Wang et al. |
| 2006/0084687 | A1 | 4/2006 | Boyce et al. |
| 2007/0037853 | A1 | 2/2007 | Barsanti et al. |
| 2008/0200462 | A1 | 8/2008 | Xi et al. |

FOREIGN PATENT DOCUMENTS

| | | |
|---|---|---|
| GB | 2 157 285 | 10/1985 |
| WO | WO 98/27108 | 6/1998 |
| WO | WO 00/23487 | 4/2000 |
| WO | WO 00/59887 | 10/2000 |
| WO | WO 01/26656 | 4/2001 |
| WO | WO 01/30768 | 5/2001 |
| WO | WO 01/83575 | 11/2001 |
| WO | WO 01/94317 | 12/2001 |
| WO | WO 01/94318 | 12/2001 |
| WO | WO 01/98278 | 12/2001 |
| WO | WO 02/10140 | 2/2002 |
| WO | WO 02/28839 | 4/2002 |
| WO | WO 02/46168 | 6/2002 |
| WO | WO 02/056880 | 7/2002 |
| WO | WO 02/057244 | 7/2002 |
| WO | WO 02/083143 | 10/2002 |
| WO | WO 03/039460 | 5/2003 |
| WO | WO 03/043995 | 5/2003 |
| WO | WO 03/049527 | 6/2003 |
| WO | WO 03/049678 | 6/2003 |
| WO | WO 03/049679 | 6/2003 |
| WO | WO 03/050064 | 6/2003 |
| WO | WO 03/050122 | 6/2003 |
| WO | WO 03/059289 | 7/2003 |
| WO | WO 03/070701 | 8/2003 |
| WO | WO 03/076432 | 9/2003 |
| WO | WO 03/079973 | 10/2003 |
| WO | WO 03/088903 | 10/2003 |
| WO | WO 03/093263 | 11/2003 |
| WO | WO 03/093264 | 11/2003 |

(Continued)

OTHER PUBLICATIONS

U.S. Appl. No. 12/242,360, filed Sep. 30, 2008, Wang et al.

(Continued)

*Primary Examiner*—Bruck Kifle
(74) *Attorney, Agent, or Firm*—Vinit Kathardekar

(57) ABSTRACT

The present invention relates to new substituted imidazole compounds have the following Formula (I) and to the pharmaceutically acceptable salts, esters, or prodrugs thereof, to compositions of the compounds together with pharmaceutically acceptable carriers, and to uses of the compounds:

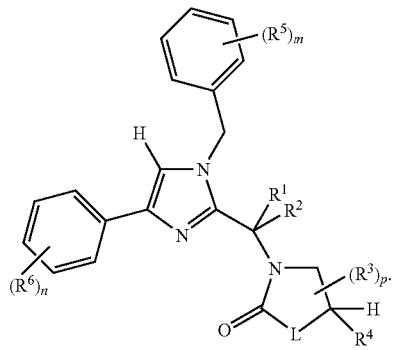

(I)

20 Claims, No Drawings

FOREIGN PATENT DOCUMENTS

| | | |
|---|---|---|
| WO | WO 03/094839 | 11/2003 |
| WO | WO 03/097053 | 11/2003 |
| WO | WO 03/097643 | 11/2003 |
| WO | WO 03/099211 | 12/2003 |
| WO | WO 03/103575 | 12/2003 |
| WO | WO 03/105855 | 12/2003 |
| WO | WO 03/106417 | 12/2003 |
| WO | WO 03/106426 | 12/2003 |
| WO | WO 2004/004652 | 1/2004 |
| WO | WO 2004/006865 | 1/2004 |
| WO | WO 2004/009036 | 1/2004 |
| WO | WO 2004/018058 | 3/2004 |
| WO | WO 2004/024086 | 3/2004 |
| WO | WO 2004/026226 | 4/2004 |
| WO | WO 2004/031174 | 4/2004 |
| WO | WO 2004/041808 | 5/2004 |
| WO | WO 2004/041809 | 5/2004 |
| WO | WO 2004/064741 | 8/2004 |
| WO | WO 2004/071448 | 8/2004 |
| WO | WO 2004/100873 | 11/2004 |
| WO | WO 2004/103282 | 12/2004 |
| WO | WO 2004/113335 | 12/2004 |
| WO | WO 2005/100322 | 10/2005 |
| WO | WO 2005/107762 | 11/2005 |
| WO | WO 2006/002236 | 1/2006 |
| WO | WO 2007/021794 | 2/2007 |

OTHER PUBLICATIONS

Kapoor, et al., "Probing Spindle Assembly Mechanisms with Monastrol, a Small Molecule Inhibitor of the Mitotic Kinesin, Eg5", *J. Cell Biol.*, 150:975-988 (2000).

Enos, et al., "Mutation of a Gene That Encodes a Kinesin-like Protein Blocks Nuclear Division in *A. nidulans*", *Cell* 60:1019-1027, (1990).

Hagan, et al., "Novel potential mitotic motor protein encoded by the fission yeast cut7+ gene", *Nature* 347:563-566, (1990).

Giet, et al., "The *Xenopus laevis* Aurora-related Protein Kinase pEg2 Associates with an Phosphorylates the Kinesin-related Protein X1Eg5*", *J. Biol. Chem.* 274(21): 15005-15013, (1999).

Mayer, et al., "Small Molecule Inhibitor of Mitotic Spindle Bipolarity Identified in a Phenotype-Based Screen", *Science* 286:971-974, (1999).

Debonis, et al., "Interaction of the Mitotic Inhibitor Monastrol with Human Kinesin Eg5+" *Biochemistry*, 42:338-349, (2003).

IUPAC, Commission on Nomenclature of Organic Chemistry, Organic Chemistry Division, "Rules for the Nomenclature of Organic Chemistry", Section E: Stereochemistry, *Pure & Appl. Chem.* 45:13-30, (1976).

Kaiser, et al., "All-*trans*-Retinoic Acid-mediated Growth Inhibition Involves Inhibition of Human Kinesin-related Protein HsEg5*", *J. Biol. Chem.* 274:18925-18931, (1999).

Shirley, et al., "The Metalation of 1-Methyl-, 1-Benzyl- and 1-Phenylimidazole with n-Butyllithium", *J. Amer. Chem. Soc.*, 79:4922-4927 (1957).

Whitten, et al., "A One Step Synthesis of 4-Substituted Imidazoles. An Important Observation When N-Alkylating Imidazoles", *J. Heterocyclic Chem*,. 25:1845-1847 (1988).

Matthews, et al., "Synthesis and Cardiotonic Activity of Novel Biimidazoles", *J. Med. Chem*, 33(1): 317-327 (1990).

Deng, et al., "Synthetic Applications of Azolium Ylides to a Traceless Solid-Phase Synthesis of 2-Substituted Azoles", *Organic Letters*, 4(23): 4017-4020 (2002).

Gebert, et al., Untersuchungen zur Struktur-Wirkung-Beziehung neuer Trans-aminatoren mit Imidazol-, Thiazol- und Benzimidazolgeriist**), Liebigs Ann. Chem., 644-654 (1974) (with English abstract).

Blangy, et al., "Phosphorylatin by p34$^{cdc2}$ Regulates Spindle Association of Human Eg5, a Kinesin-Related Motor Essential for Bipolar Spindle Formation In Vivo", Cell, vol. 83, 1159-1169 (1995).

Prodrug [online], [retrieved on Mar. 11, 2007]. Retrieved from the Internet, URL; http://en.wikipedia.org/wiki/Prodrugs.

RN 154508-94-8, retrieved from CAPLUS on Oct. 3, 2007.

RN 301154-06-3, retrieved from CAPLUS on Oct. 3, 2007.

Haque, et al., "Monastrol, a Prototype Anti-Cancer Drug That Inhibits a Mitotic Kinesin, Induces Rapid Burst of Axonal Outgrowth From Cultured Postmitotic Neurons, Cell Motility and the Cytoskeleton," Dept. of Neurobiology and Anatomy, Drexel University College of Medicine, Philidelphia, PA., 58:10-16 (2004).

CYCLIZED DERIVATIVES AS EG-5 INHIBITORS

CROSS-REFERENCE TO RELATED APPLICATION

This application claims the benefit under 35 U.S.C. §119(e) to U.S. provisional application Ser. No. 60/883,740, filed on Jan. 5, 2007, which is incorporated herein by reference in its entirety.

BACKGROUND OF THE INVENTION

1. Field of the Invention

This invention relates to substituted imidazole compounds and pharmaceutically acceptable salts, esters, or prodrugs thereof. This invention is further directed to compositions of such compounds together with pharmaceutically acceptable carriers and to uses of such compounds.

2. State of the Art

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIF11) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., Cell 83:1159-1169, 1995). Mutations in bimC and cut7 genes, which are considered to be homologues of KSP, cause failure in centrosome separation in *Aspergillus nidulans* (Enos, A. P., and N. R. Morris, Cell 60:1019-1027, 1990) and *Schizosaccharomyces pombe* (Hagan, I., and M. Yanagida, Nature 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., J. Biol. Chem. 274, 18925-18931, 1999). Interestingly, the *Xenopus laevis* Aurora-related protein kinase pEg2 was shown to associate and phosphorylate XlEg5 (Giet, R., et al., J. Biol. Chem. 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., Science 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., Biochemistry, 42:338-349, 2003; Kapoor, T. M., et al., J. Cell Biol., 150:975-988, 2000).

In light of the importance of improved chemotherapeutics, there is a need for KSP inhibitors that are effective in vivo inhibitors of KSP and KSP-related proteins.

SUMMARY OF THE INVENTION

This invention is directed to substituted imidazole compounds of Formula (I), to the pharmaceutically acceptable salts, esters, or prodrugs thereof, to their preparation, to pharmaceutical compositions comprising the compounds, and to their uses for treating KSP mediated diseases:

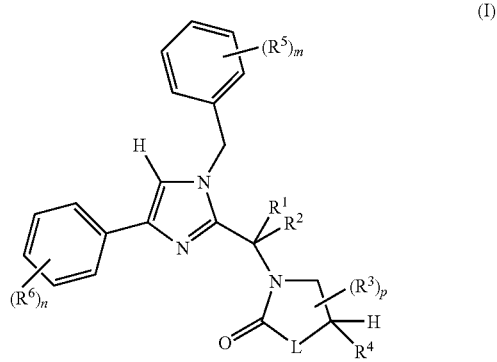

wherein:

$R^1$ is selected from the group consisting of alkyl and substituted alkyl;

$R^2$ is selected from the group consisting of hydrogen, alkyl, and substituted alkyl;

L is selected from the group consisting of
  a) —O—;
  b) —OCH$_2$—, —CH$_2$O—, —C(O)NR$^7$—;
  c) —CH$_2$OCH$_2$—, —CH$_2$NR$^7$CH$_2$—, —CH$_2$CH$_2$O—, —C(O)NR$^7$CH$_2$—, and —CH$_2$CH$_2$NR$^7$—;

$R^3$ and $R^4$ are independently selected from the group consisting of halo, alkyl, and substituted alkyl;

$R^5$ and $R^6$ are independently selected from the group consisting of cyano, alkyl, substituted alkyl, alkoxy, substituted alkoxy, halo, and hydroxy;

$R^7$ is selected from the group consisting of hydrogen, alkyl, and —SO$_2$alkyl;

m is 0, 1, 2, or 3;

n is 0, 1, 2, or 3; and p is 0 or 1.

DETAILED DESCRIPTION OF THE INVENTION

A. Compounds of the Invention

Compounds of the invention include those of Formula (I) or a pharmaceutically acceptable salt, ester, or prodrug thereof:

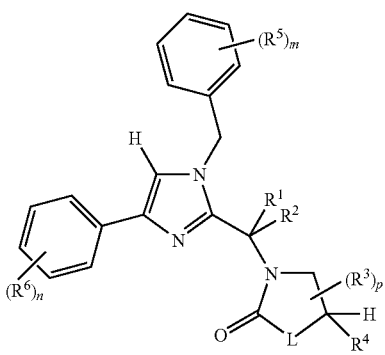

(I)

wherein:
R[1] is selected from the group consisting of alkyl and substituted alkyl;
R[2] is selected from the group consisting of hydrogen, alkyl, and substituted alkyl;
L is selected from the group consisting of
 a) —O—;
 b) —OCH$_2$—, —CH$_2$O—, —C(O)NR[7]—;
 c) —CH$_2$OCH$_2$—, —CH$_2$NR[7]CH$_2$—, —CH$_2$CH$_2$O—, —C(O)NR[7]CH$_2$—, and —CH$_2$CH$_2$NR[7]—;
R[3] and R[4] are independently selected from the group consisting of halo, alkyl, and substituted alkyl;
R[5] and R[6] are independently selected from the group consisting of cyano, alkyl, substituted alkyl, alkoxy, substituted alkoxy, halo, and hydroxy;
R[7] is selected from the group consisting of hydrogen, alkyl, and —SO$_2$alkyl;
m is 0, 1, 2, or 3;
n is 0, 1, 2, or 3; and
p is 0 or 1.

In one embodiment, R[1] and R[2] are alkyl. In one aspect, R[1] and R[2] are methyl.

In one embodiment, R[1] is alkyl and R[2] is hydrogen. In some aspects R[1] is selected from the group consisting of isopropyl, t-butyl, and propyl.

In one embodiment, p is 0.

In another embodiment, p is 1. In some aspects R[3] is alkyl such as methyl. In other aspects, R[3] is halo.

When p is 1, R[3] can be attached to any carbon atom of the ring suitable for substitution, including substitutable carbon atoms of L. In one embodiment, R[3] can be on the carbon atom to which R[4] is attached, for example as in the following formula:

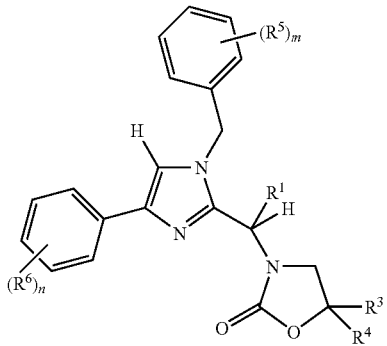

wherein R[1], R[3], R[4], R[5], R[6], n, and m are as defined for Formula (I).

The substituents R[3] and R[4] do not include groups that cyclize to form a Spiro ring. Such rings are not included in the definition of alkyl and substituted alkyl.

In one embodiment, R[4] is substituted alkyl. In some aspects, R[4] is alkyl substituted with 1 to 5 substituents selected from the group consisting of amino, substituted amino, halo, alkoxy, substituted alkoxy, and hydroxy.

In one embodiment, R[4] is selected from the group consisting of halo, —CH$_2$NH$_2$, —(CH$_2$)$_2$NH$_2$, —(CH$_2$)$_3$NH$_2$, and —CH$_2$OH.

In one embodiment and independent of R[4], R[3] is selected from the group consisting of halo, —CH$_2$NH$_2$, —(CH$_2$)$_2$NH$_2$, —(CH$_2$)$_3$NH$_2$, and —CH$_2$OH.

In one embodiment, m is 0.

In one embodiment, R[6] is halo.

In one embodiment, R[6] and the phenyl ring to which it is attached is selected from the group consisting of phenyl, 3-bromophenyl, 3-chlorophenyl, 4-cyanophenyl, 2,5-difluorophenyl, 3-fluorophenyl, 2-methoxyphenyl, 3-methoxyphenyl, 4-methoxyphenyl, 4-methylphenyl, 2-trifluoromethylphenyl, and 3-trifluoromethylphenyl.

The linker L is a divalent linker and is disclosed herein in the —C(O)-L-CHR[4]— orientation.

In one embodiment, L and the atoms to which it is joined together with (R[3])$_p$ and R[4] form a ring selected from the group consisting of:

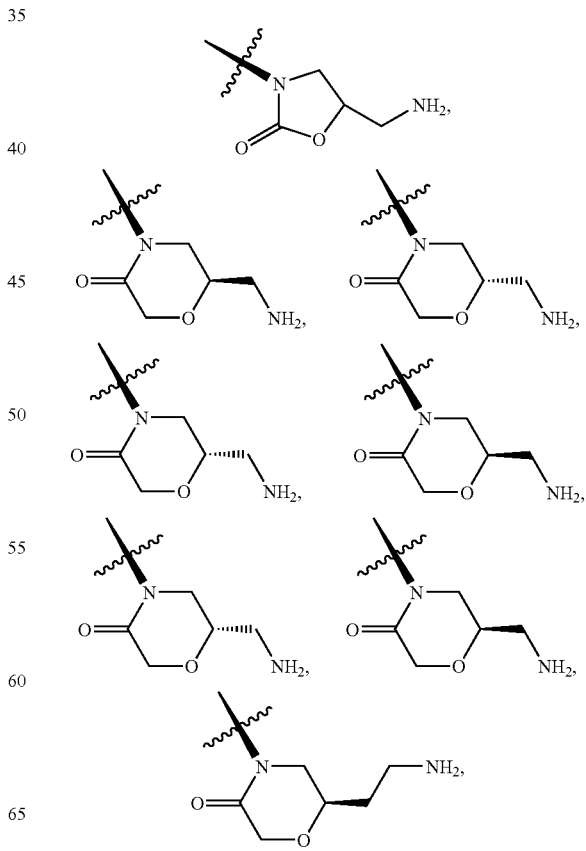

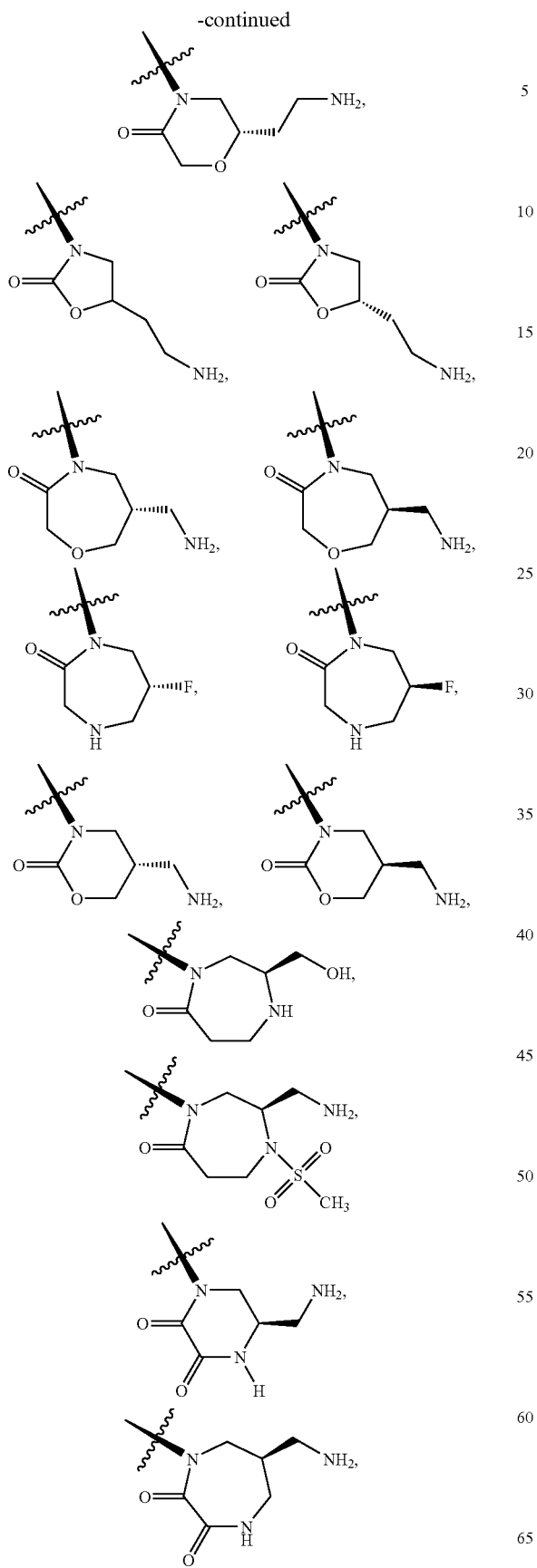
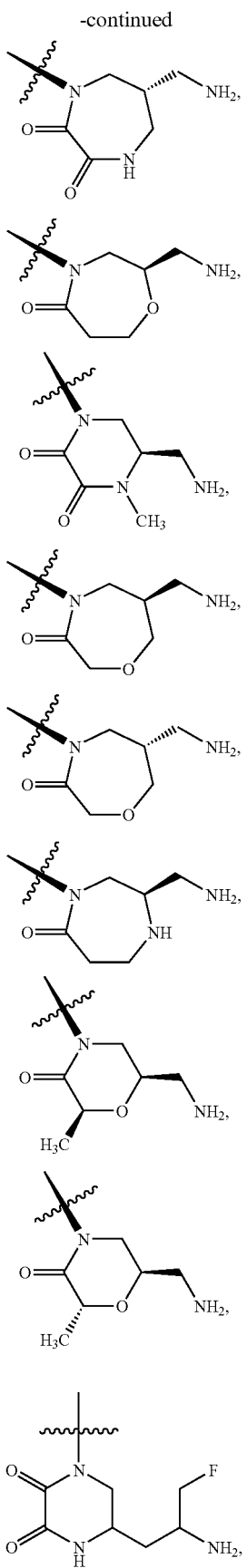

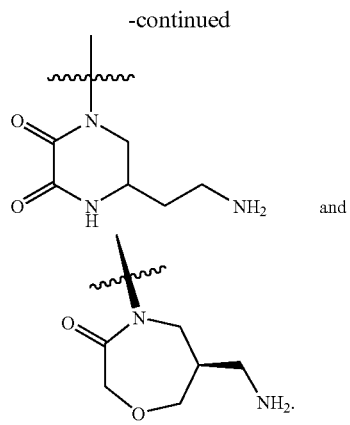 and 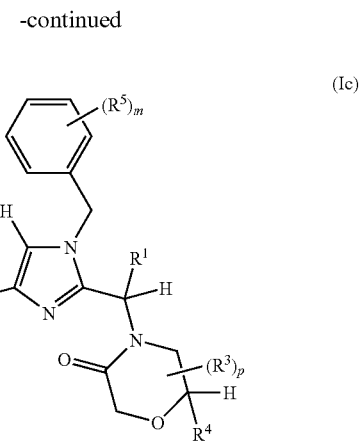

In one embodiment, provided is a compound having Formula (Ia) or a pharmaceutically acceptable salt, ester, or prodrug thereof:

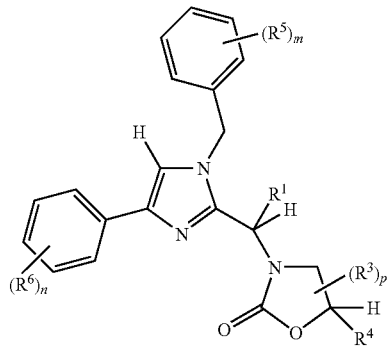
(Ia)

wherein $R^1$, $R^3$, $R^4$, $R^5$, $R^6$, n, m, and p are as defined for Formula (I).

In one embodiment, provided is a compound having Formula (Ib)-(Id) or a pharmaceutically acceptable salt, ester, or prodrug thereof:

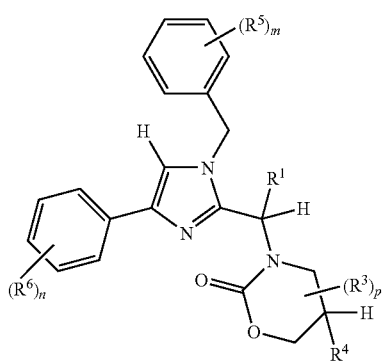
(Ib)

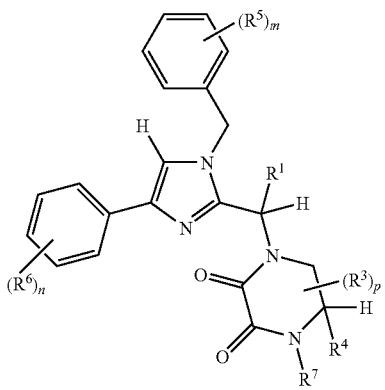
(Ic)

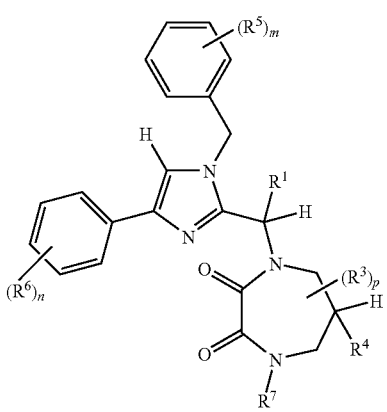
(Id)

wherein $R^1$, $R^3$, $R^4$, $R^5$, $R^6$, n, m, and p are as defined for Formula (I).

In one embodiment, provided is a compound having Formula (Ie)-(Ii) or a pharmaceutically acceptable salt, ester, or prodrug thereof:

(Ie)

-continued

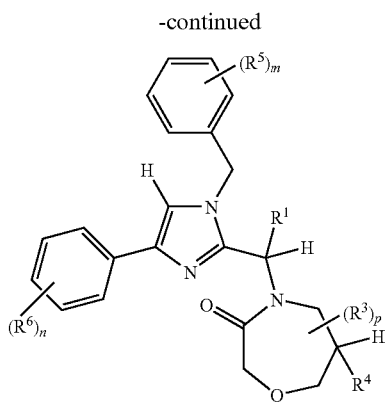

(If)

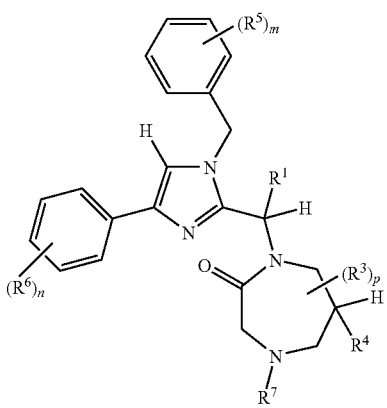

(Ig)

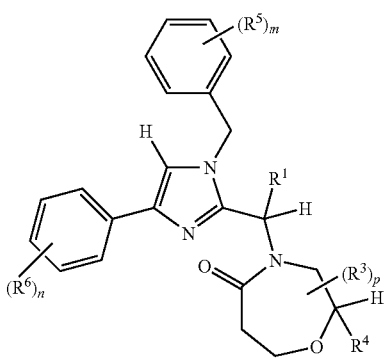

(Ih)

-continued

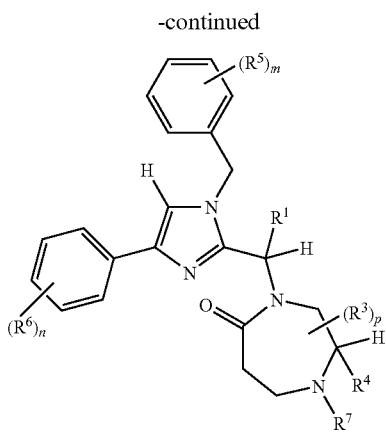

(Ii)

wherein $R^1$, $R^3$, $R^4$, $R^5$, $R^6$, n, m, and p are as defined for Formula (I).

In one embodiment of the compounds of Formula (Ia)-(Ii), $R^1$ is alkyl. In another embodiment $R^1$ is selected from the group consisting of isopropyl, t-butyl, and propyl.

In one embodiment, $R^4$ is substituted alkyl. In some aspects, $R^4$ is alkyl substituted with 1 to 5 substituents selected from the group consisting of amino, substituted amino, halo, alkoxy, substituted alkoxy, and hydroxy.

In one embodiment, $R^4$ is selected from the group consisting of halo, —$CH_2NH_2$, —$(CH_2)_2NH_2$, —$(CH_2)_3NH_2$, and —$CH_2OH$.

In one embodiment, and independent of $R^4$, $R^3$ is selected from the group consisting of halo, —$CH_2NH_2$, —$(CH_2)_2NH_2$, —$(CH_2)_3NH_2$, and —$CH_2OH$.

In some aspects, m is 1. In one embodiment, $R^5$ is halo.
In one embodiment, m is 0.
In some aspects, n is 1 or 2. In one embodiment, $R^6$ is halo.
In one embodiment, $R^6$ and the phenyl ring to which it is attached is selected from the group consisting of phenyl, 3-bromophenyl, 3-chlorophenyl, 4-cyanophenyl, 2,5-difluorophenyl, 3-fluorophenyl, 2-methoxyphenyl, 3-methoxyphenyl, 4-methoxyphenyl, 4-methylphenyl, 2-trifluoromethylphenyl, and 3-trifluoromethylphenyl.

In one embodiment, provided is a compound in Table 1 or a pharmaceutically acceptable salt, ester, or prodrug thereof. In one embodiment, provided is a stereoisomer of any one of the compounds in Table 1. In one aspect, the stereoisomer is an enantiomer. In another aspect, the stereoisomer is a diastereomer.

TABLE 1

| Compound | Structure | Name |
|---|---|---|
| 1 | 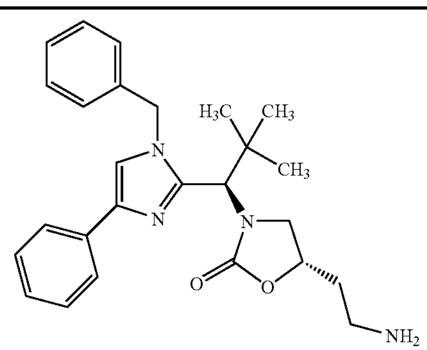 | (5R)-5-(2-aminoethyl)-3-[(1R)-1-(1-benzyl-4-phenyl-1H-imidazol-2-yl)-2,2-dimethylpropyl]-1,3-oxazolidin-2-one |

TABLE 1-continued

| Compound | Structure | Name |
|---|---|---|
| 2 | 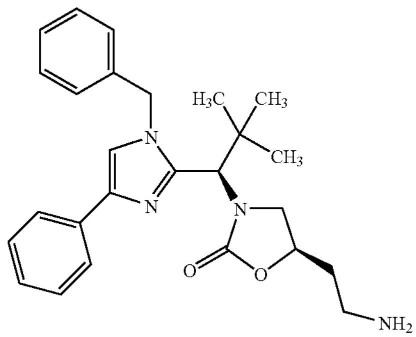 | (5S)-5-(2-aminoethyl)-3-[(1R)-1-(1-benzyl-4-phenyl-1H-imidazol-2-yl)-2,2-dimethylpropyl]-1,3-oxazolidin-2-one |
| 3 | 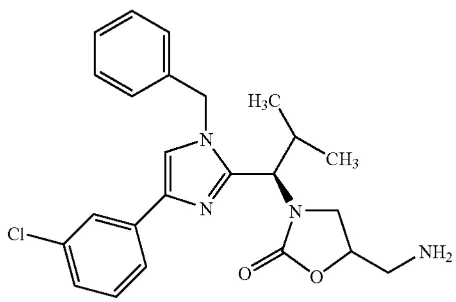 | 5-(aminomethyl)-3-{(1R)-1-[1-benzyl-4-(3-chlorophenyl)-1H-imidazol-2-yl]-2-methylpropyl}-1,3-oxazolidin-2-one |
| 4 | 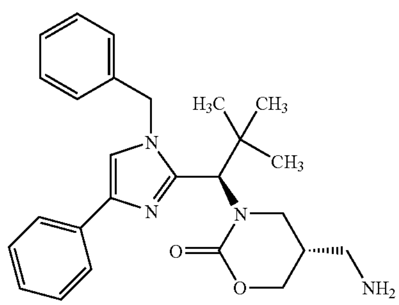 | (5S)-5-(aminomethyl)-3-[(1R)-1-(1-benzyl-4-phenyl-1H-imidazol-2-yl)-2,2-dimethylpropyl]-1,3-oxazinan-2-one |
| 5 | 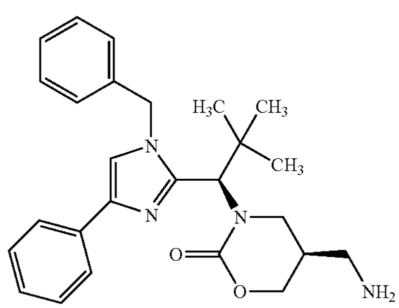 | (5R)-5-(aminomethyl)-3-[(1R)-1-(1-benzyl-4-phenyl-1H-imidazol-2-yl)-2,2-dimethylpropyl]-1,3-oxazinan-2-one |
| 6 | 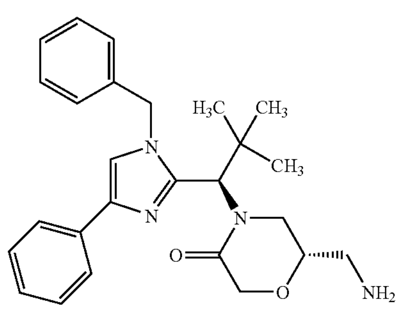 | (6S)-6-(aminomethyl)-4-[(1R)-1-(1-benzyl-4-phenyl-1H-imidazol-2-yl)-2,2-dimethylpropyl]morpholin-3-one |

TABLE 1-continued

| Compound | Structure | Name |
|---|---|---|
| 7 | 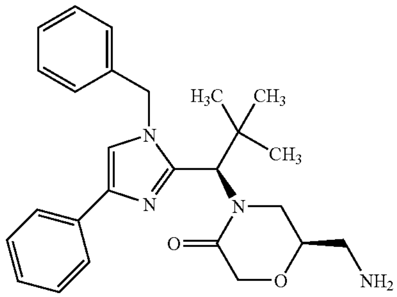 | (6R)-6-(aminomethyl)-4-[(1R)-1-(1-benzyl-4-phenyl-1H-imidazol-2-yl)-2,2-dimethylpropyl]morpholin-3-one |
| 8 | 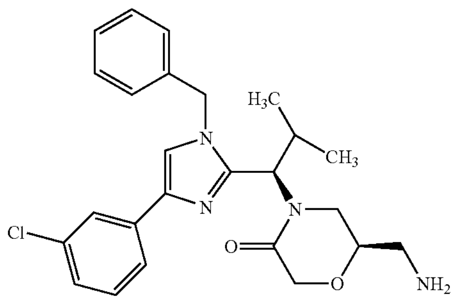 | (6R)-6-(aminomethyl)-4-{(1R)-1-[1-benzyl-4-(3-chlorophenyl)-1H-imidazol-2-yl]-2-methylpropyl}morpholin-3-one |
| 9 | 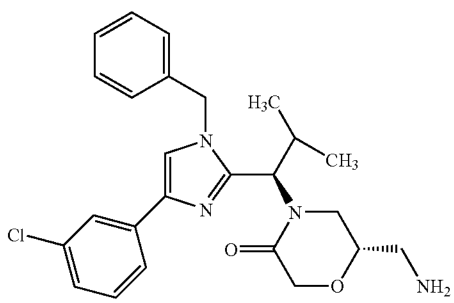 | (6S)-6-(aminomethyl)-4-{(1R)-1-[1-benzyl-4-(3-chlorophenyl)-1H-imidazol-2-yl]-2-methylpropyl}morpholin-3-one |
| 10 | 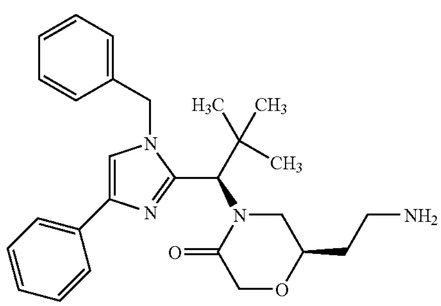 | (6R)-6-(2-aminoethyl)-4-[(1R)-1-(1-benzyl-4-phenyl-1H-imidazol-2-yl)-2,2-dimethylpropyl]morpholin-3-one |
| 11 | 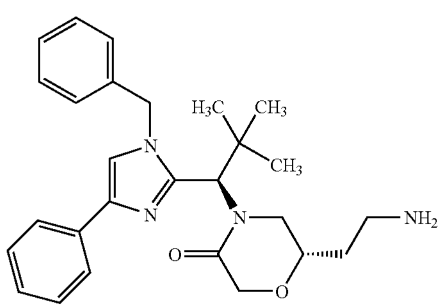 | (6S)-6-(2-aminoethyl)-4-[(1R)-1-(1-benzyl-4-phenyl-1H-imidazol-2-yl)-2,2-dimethylpropyl]morpholin-3-one |

TABLE 1-continued

| Compound | Structure | Name |
|---|---|---|
| 12 | 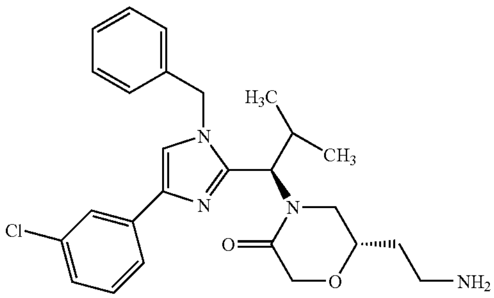 | (6S)-6-(2-aminoethyl)-4-{(1R)-1-[1-benzyl-4-(3-chlorophenyl)-1H-imidazol-2-yl]-2-methylpropyl}morpholin-3-one |
| 13 | 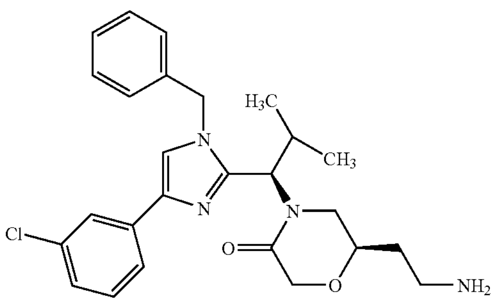 | (6R)-6-(2-aminoethyl)-4-{(1R)-1-[1-benzyl-4-(3-chlorophenyl)-1H-imidazol-2-yl]-2-methylpropyl}morpholin-3-one |
| 14 | 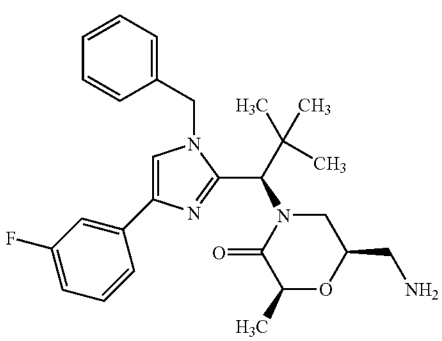 | (2S,6R)-6-(aminomethyl)-4-{(1R)-1-[1-benzyl-4-(3-fluorophenyl)-1H-imidazol-2-yl]-2,2-dimethylpropyl}-2-methylmorpholin-3-one |
| 15 | 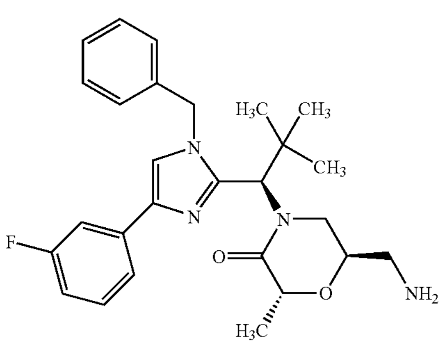 | (2R,6R)-6-(aminomethyl)-4-{(1R)-1-[1-benzyl-4-(3-fluorophenyl)-1H-imidazol-2-yl]-2,2-dimethylpropyl}-2-methylmorpholin-3-one |

TABLE 1-continued

| Compound | Structure | Name |
|---|---|---|
| 16 | 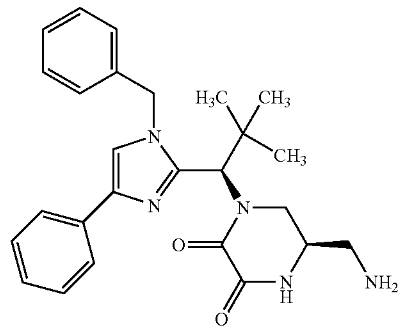 | (5R)-5-(aminomethyl)-1-[(1R)-1-(1-benzyl-4-phenyl-1H-imidazol-2-yl)-2,2-dimethylpropyl]piperazine-2,3-dione |
| 17 | 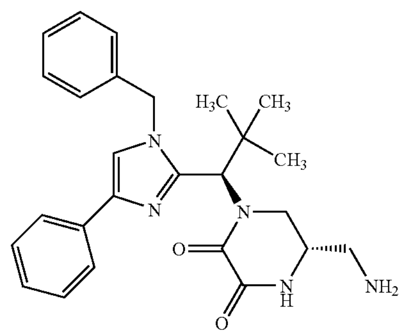 | (5S)-5-(aminomethyl)-1-[(1R)-1-(1-benzyl-4-phenyl-1H-imidazol-2-yl)-2,2-dimethylpropyl]piperazine-2,3-dione |
| 18 | 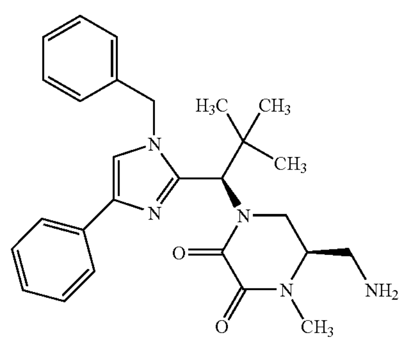 | (5R)-5-(aminomethyl)-1-[(1R)-1-(1-benzyl-4-phenyl-1H-imidazol-2-yl)-2,2-dimethylpropyl]-4-methylpiperazine-2,3-dione |
| 19 | 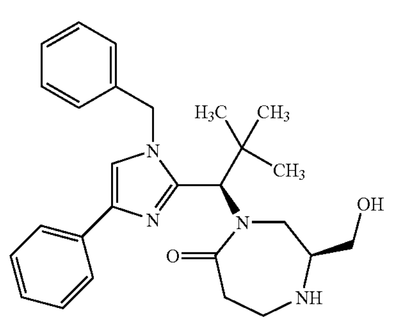 | (2S)-4-[(1R)-1-(1-benzyl-4-phenyl-1H-imidazol-2-yl)-2,2-dimethylpropyl]-2-(hydroxymethyl)-1,4-diazepan-5-one |

TABLE 1-continued

| Compound | Structure | Name |
|---|---|---|
| 20 | 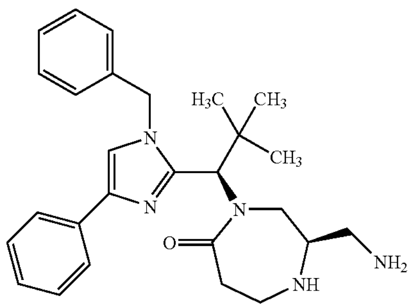 | (2R)-2-(aminomethyl)-4-[(1R)-1-(1-benzyl-4-phenyl-1H-imidazol-2-yl)-2,2-dimethylpropyl]-1,4-diazapan-5-one |
| 21 | 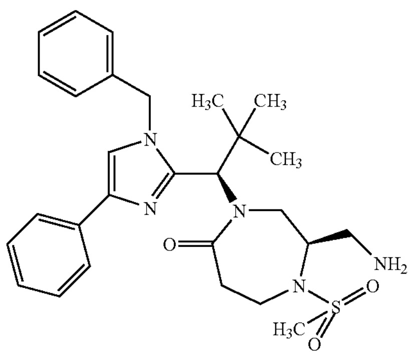 | (2R)-2-(aminomethyl)-4-[(1R)-1-(1-benzyl-4-phenyl-1H-imidazol-2-yl)-2,2-dimethylpropyl]-1-(methylsulfonyl)-1,4-diazepan-5-one |
| 22 | 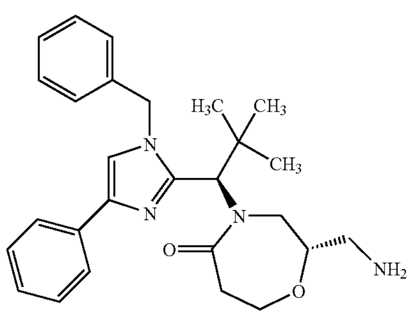 | (2S)-2-(aminomethyl)-4-[(1R)-1-(1-benzyl-4-phenyl-1H-imidazol-2-yl)-2,2-dimethylpropyl]-1,4-oxazepan-5-one |
| 23 | 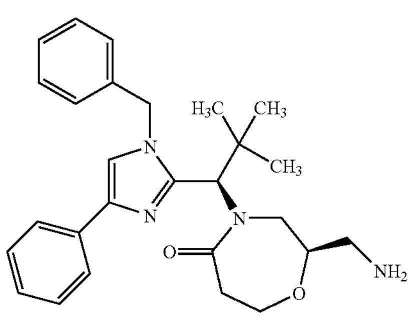 | (2R)-2-(aminomethyl)-4-[(1R)-1-(1-benzyl-4-phenyl-1H-imidazol-2-yl)-2,2-dimethylpropyl]-1,4-oxazepan-5-one |

TABLE 1-continued

| Compound | Structure | Name |
|---|---|---|
| 24 | 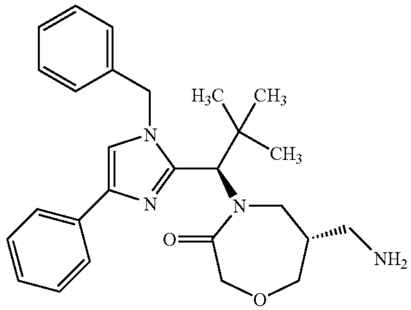 | (6S)-6-(aminomethyl)-4-[(1R)-1-(1-benzyl-4-phenyl-1H-imidazol-2-yl)-2,2-dimethylpropyl]-1,4-oxazepan-3-one |
| 25 | 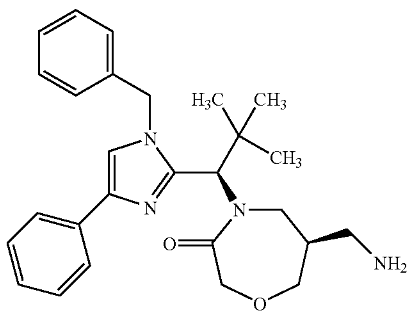 | (6R)-6-(aminomethyl)-4-[(1R)-1-(1-benzyl-4-phenyl-1H-imidazol-2-yl)-2,2-dimethylpropyl]-1,4-oxazepan-3-one |
| 26 | 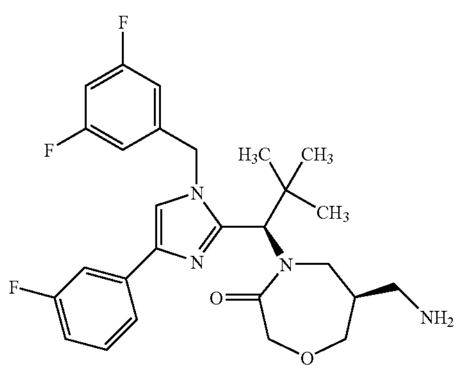 | (6R)-6-(aminomethyl)-4-{(1R)-1-[1-(3,5-difluorobenzyl)-4-(3-fluorophenyl)-1H-imidazol-2-yl]-2,2-dimethylpropyl}-1,4-oxazepan-3-one |
| 27 | 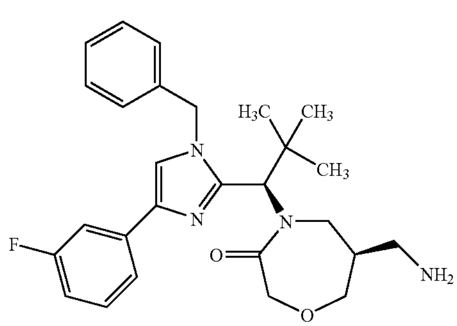 | (6R)-6-(aminomethyl)-4-{(1R)-1-[1-benzyl-4-(3-fluorophenyl)-1H-imidazol-2-yl]-2,2-dimethylpropyl}-1,4-oxazepan-3-one |

TABLE 1-continued

| Compound | Structure | Name |
|---|---|---|
| 28 | 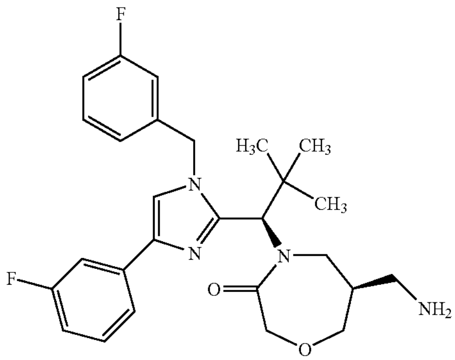 | (6R)-6-(aminomethyl)-4-{(1R)-1-[1-(3-fluorobenzyl)-4-(3-fluorophenyl)-1H-imidazol-2-yl]-2,2-dimethylpropyl}-1,4-oxazepan-3-one |
| 29 | 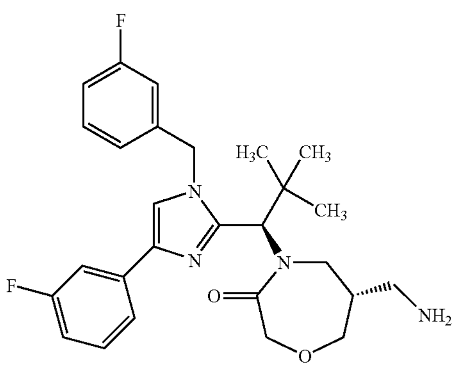 | (6S)-6-(aminomethyl)-4-{(1R)-1-[1-(3-fluorobenzyl)-4-(3-fluorophenyl)-1H-imidazol-2-yl]-2,2-dimethylpropyl}-1,4-oxazepan-3-one |
| 30 | 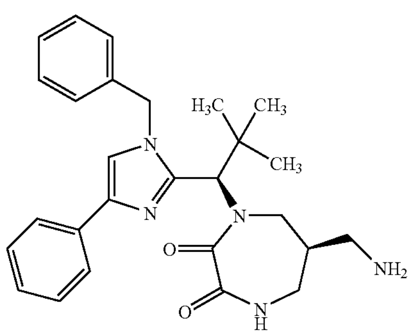 | (6S)-6-(aminomethyl)-1-[(1R)-1-(1-benzyl-4-phenyl-1H-imidazol-2-yl)-2,2-dimethylpropyl]-1,4-diazepane-2,3-dione |
| 31 | 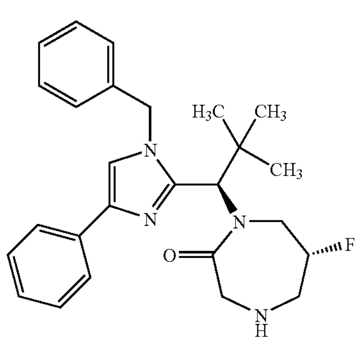 | (6R)-1-[(1R)-1-(1-benzyl-4-phenyl-1H-imidazol-2-yl)-2,2-dimethylpropyl]-6-fluoro-1,4-diazepan-2-one |

TABLE 1-continued

| Compound | Structure | Name |
|---|---|---|
| 32 | 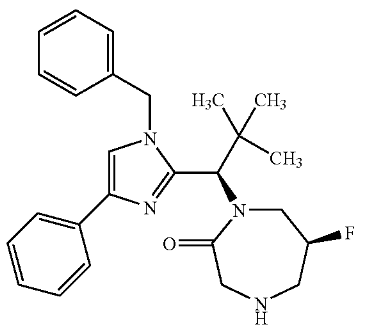 | (6S)-1-[(1R)-1-(1-benzyl-4-phenyl-1H-imidazol-2-yl)-2,2-dimethylpropyl]-6-fluoro-1,4-diazepan-2-one |
| 33 | 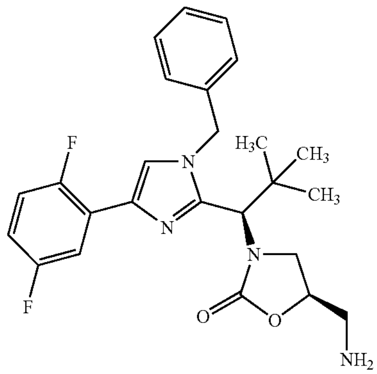 | (R)-5-(aminomethyl)-3-((R)-1-(1-benzyl-4-(2,5-difluorophenyl)-1H-imidazol-2-yl)-2,2-dimethylpropyl)oxazolidin-2-one |
| 34 | 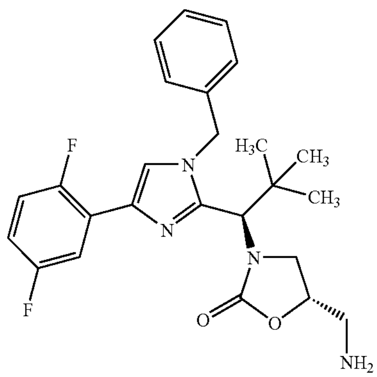 | (S)-5-(aminomethyl)-3-((R)-1-(1-benzyl-4-(2,5-difluorophenyl)-1H-imidazol-2-yl)-2,2-dimethylpropyl)oxazolidin-2-one |

Methods and Compositions of the Invention

Also provided is a composition comprising a compound of Formula (I) or (Ia)-(Ii) (including mixtures and/or salts thereof) and a pharmaceutically acceptable excipient or carrier.

In another aspect, the present invention provides methods of treating a mammalian patient suffering from a disorder mediated, at least in part, by KSP. Thus, the present invention provides methods of treating a mammalian patient in need of such treatment comprising administering to the patient a therapeutically effective amount of a compound of Formula (I) or (Ia)-(Ii) (including mixtures thereof) either alone or in combination with other anticancer agents.

B. Definitions and Overview

As discussed above, the present invention is directed in part to new substituted pyrazole and triazole compounds.

It is to be understood that the terminology used herein is for the purpose of describing particular embodiments only and is not intended to limit the scope of the present invention. It must be noted that as used herein and in the claims, the singular forms "a" and "the" include plural referents unless the context clearly dictates otherwise. In this specification and in the claims which follow, reference will be made to a number of terms which shall be defined to have the following meanings:

As used herein, "alkyl" refers to monovalent saturated aliphatic hydrocarbyl groups having from 1 to 6 carbon atoms and preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, aryloxy, cyano, halogen, hydroxy, nitro, carboxyl, carboxyl ester, cycloalkyl, substituted cycloalkyl, spirocycloalkyl, heteroaryl, substituted heteroaryl, heterocyclic, substituted heterocyclic, —SO$_2$-alkyl, and —SO$_2$-substituted alkyl.

"Alkylene" refers to divalent saturated aliphatic hydrocarbyl groups preferably having from 1 to 5 and preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) or (—CH(CH$_3$)CH$_2$—) and the like.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxyacyl" or "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic with the proviso that any hydroxy substitution is not attached to an acetylenic carbon atom.

"Amino" refers to the group —NH$_2$.

"Cyano" refers to the group —CN.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' or R" is hydrogen.

"Acylamino" refers to the groups —NRC(O)alkyl, —NRC(O) substituted alkyl, —NRC(O)cycloalkyl, —NRC(O) substituted cycloalkyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O) heterocyclic, and —NRC(O) substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) in which the condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl ester, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl($NH_2$—$SO_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Spirocycloalkyl" refers to cyclic groups from 3 to 10 carbon atoms having a cycloalkyl ring with a spiro union (the union formed by a single atom which is the only common member of the rings) as exemplified by the following structure:

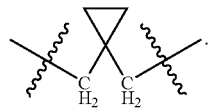

"Substituted cycloalkyl" refers to a cycloalkyl group, having from 1 to 5 substituents selected from the group consisting of alkyl, substituted alkyl, oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, substituted heterocyclic, —$SO_2$-alkyl and —$SO_2$-cycloalkyl.

"Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

"Nitrogen-containing heteroaryl" and "nitrogen-containing substituted heteroaryl" refers to heteroaryl groups and substituted heteroaryl groups comprising at least one nitrogen ring atom and optionally comprising other non-nitrogen hetero ring atoms such as sulfur, oxygen and the like.

"Heteroaryloxy" refers to the group —O-heteroaryl and "substituted heteroaryloxy" refers to the group —O-substituted heteroaryl wherein heteroaryl and substituted heteroaryl are as defined herein.

"Heterocycle" or "heterocyclic" or "heterocycloalkyl" or "heterocyclyl" refers to a saturated or unsaturated (but not aromatic) group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring. In one embodiment, the nitrogen and/or sulfur atom(s) of the heterocyclic group are optionally oxidized to provide for the N-oxide, sulfinyl, and sulfonyl moieties.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitrogen-containing heterocyclic" and "nitrogen-containing substituted heterocyclic" refers to heterocyclic groups and substituted heterocyclic groups comprising at least one nitrogen ring atom and optionally comprising other non-nitrogen hetero ring atoms such as sulfur, oxygen and the like.

"Thiol" refers to the group —SH.

"Alkylthio" or "thioalkoxy" refers to the group —S-alkyl.

"Substituted alkylthio" or "substituted thioalkoxy" refers to the group —S-substituted alkyl.

"Arylthio" refers to the group —S-aryl, where aryl is defined above.

"Substituted arylthio" refers to the group —S-substituted aryl, where substituted aryl is defined above.

"Heteroarylthio" refers to the group —S-heteroaryl, where heteroaryl is defined above.

"Substituted heteroarylthio" refers to the group —S-substituted heteroaryl, where substituted heteroaryl is defined above.

"Heterocyclicthio" refers to the group —S-heterocyclic and "substituted heterocyclicthio" refers to the group —S-substituted heterocyclic, where heterocyclic and substituted heterocyclic are defined above.

"Heterocyclyloxy" refers to the group heterocyclyl-O— and "substituted heterocyclyloxy" refers to the group substituted heterocyclyl-O— where heterocyclyl and substituted heterocyclyl are defined above.

"Cycloalkylthio" refers to the group —S-cycloalkyl and "substituted cycloalkylthio" refers to the group —S-substituted cycloalkyl, where cycloalkyl and substituted cycloalkyl are defined above.

"Biological activity" as used herein refers to an inhibition concentration when tested in at least one of the assays outlined herein and as defined in at least one example thereof.

As used herein, the term "pharmaceutically acceptable salts" refers to the nontoxic acid or alkaline earth metal salts of the compounds of Formula (I) and (Ia)-(Ii). These salts can be prepared in situ during the final isolation and purification of the compounds of Formula (I) and (Ia)-(Ii) or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of Formula (I) and (Ia)-(Ii) or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which hydrolyze in vivo and include those that break down in the human body to leave the parent compound, a salt thereof, or a pharmaceutically active metabolite. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound or a pharmaceutically active metabolite of Formula (I) or (Ia)-(Ii), for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above definitions are not intended to include impermissible substitution patterns (e.g., methyl substituted with 5 fluoro groups or a hydroxy group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Depiction of the compounds of Formula (I) and (Ia)-(Ii) includes the stereoisomers thereof unless the stereochemistry of a particular stereocenter is indicated otherwise. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

C. Compound Preparation

The compounds of this invention can be prepared from readily available starting materials using the following general methods and procedures. Unless otherwise indicated, the starting materials are commercially available and well known in the art. Suitable starting materials may be prepared as in PCT/US2005/022062, published as WO2006/002236, and as in PCT/US2006/031129, published as WO2007/021794, both of which are herein incorporated by reference in their entirety. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The intermediates may be used directly in the next step after being recovered from the reaction mixture, or optionally the intermediates can be recrystallized or purified via conventional means before used in the next step. All R groups are as defined for Formula (I).

Step A: Keto-Ester Synthesis

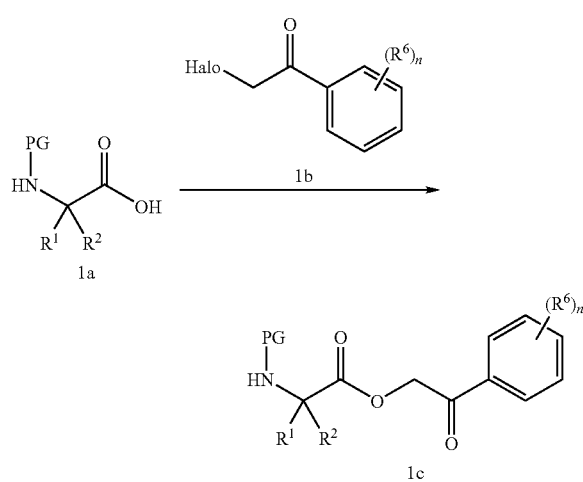

Specifically, in Step A, an appropriately protected amino acid 1a, is dissolved in a suitable amount of an inert solvent such as methanol, ethanol or acetone. Suitable protecting groups (PG) include the well-known Boc protecting group. It should be noted that amino acid 1a, is typically commercially available as are α,α-disubstituted amino acids (PG-NH—C(R$^1$)(R$^2$)—COOH). To 1a is added a stoichiometric amount of a monovalent cation, such as cesium carbonate (Cs$_2$CO$_3$) and potassium carbonate (K$_2$CO$_3$), to form the carboxylate salt (not shown). Upon substantial completion of the reaction, typically about 15 minutes to about 2 hours, excess solvent is removed by evaporation under reduced pressure. The residual cesium salt is then re-dissolved in a suitable solvent, such as DMF and then treated with one to four equivalents of the appropriate α-halo-ketone 1b (1 eq.), e.g., 2-bromoacetophenone and stirred at RT until the reaction is substantially complete. Alternatively, compounds 1a and 1b can be mixed with K$_2$CO$_3$ in acetone containing KI to give compound 1c.

The product 1c is then recovered by conventional methods such as extraction, filtration, evaporation, and the like or alternatively used directly in the next step without further purification and/or isolation.

Step B: Imidazole Formation

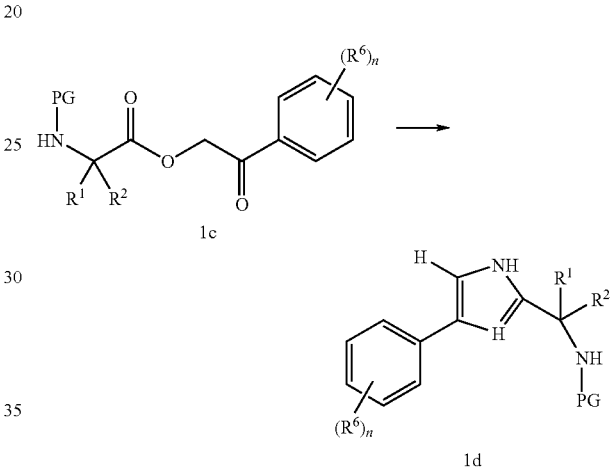

To a stirred solution of keto-ester 1c from step A in a suitable amount of inert solvent, such as toluene and xylenes, is added an excess of ammonium acetate, typically from about 2 to about 20 equivalents and preferably about 5 equivalents. In one embodiment, a Dean-Stark trap is added and the reaction mixture is heated to about 120° C. to about 160° C. until the reaction is substantially complete. In another embodiment, toluene is used without a Dean-Stark trap. Once the reaction is substantially complete, the mixture is allowed to cool to room temperature. The product, imidazole 1d, is then recovered by conventional methods such as extraction, filtration, evaporation, and the like. It is generally pure enough to use directly in the next step.

Step C: N-Alkylation of the Imidazole

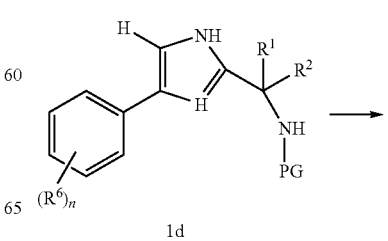

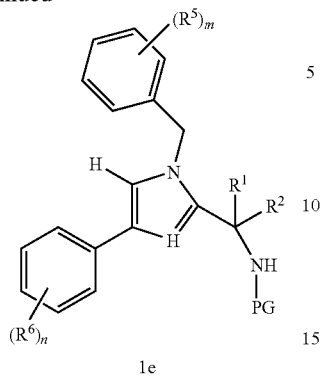

1e

The imidazole 1d is then reacted with an appropriate aryl- or heteroaryl-substituted alkyl halide, such as benzyl bromide. Typically, this can be accomplished by stirring the imidazole 1d with an excess of potassium carbonate and DMF and then adding at least an equimolar amount of the aryl- or heteroaryl-substituted alkyl halide. Once the reaction is substantially complete, the N-alkyl imidazole 1e is recovered by conventional methods such as extraction, filtration, evaporation, recrystallization, and the like.

In either case, imidazole 1e is used in Step D below.

Step D: Deprotection to the Free Amine

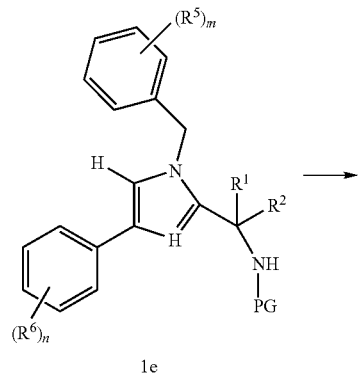

1e

1f

The protecting group, PG is then removed by conventional techniques to provide amine 1f, which is then optionally purified by conventional methods such as extraction, filtration, evaporation, and the like. The amine 1f is used directly in the next step.

Step E: Formation of Amine Heterocycle

Amine 1f is converted to compounds of Formula (I) using a variety of ring forming methods. Certain of these methods are illustrated in Schemes 1-9 and in Examples 1-26. In the Schemes, the imidazoyl moiety of amine 1f is abbreviated as "Ar". Modifications or adaptations of these methods can also be used to prepare compounds of the invention. Such modifications will be apparent to one of skill in the art.

Scheme 1

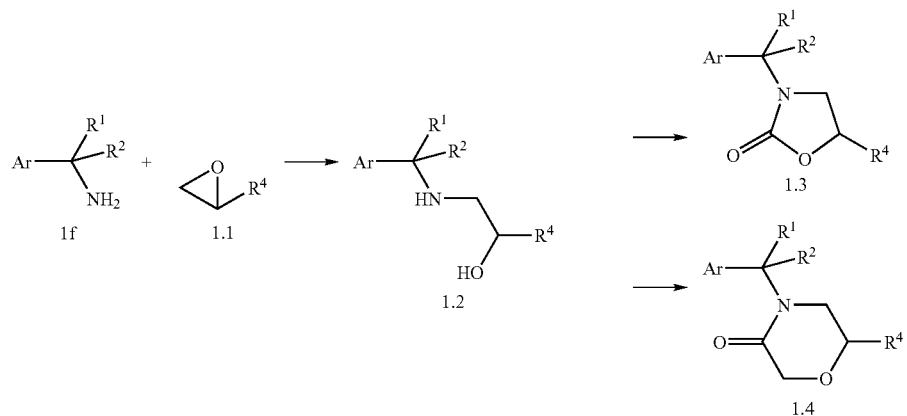

Scheme 1 shows a synthesis of the compounds of Formula (I) where, for illustrative purposes, L is —O— or —CH$_2$O— and p is 0. Amine 1f is reacted with epoxide 1.1 where R$^4$ is as previously defined for Formula (I) in the presence of a Lewis acid such as Yb(OTf)$_3$ to give amino alcohol 1.2. Treatment of 1.2 with phosgene or a phosgene equivalent under cyclization conditions gives the five-membered carbamate 1.3. An example of this transformation is given in Example 3. Alternatively, reaction of 1.2 with chloroacetyl chloride in the presence of an organic base such as triethylamine gives the six-membered lactam 1.4.

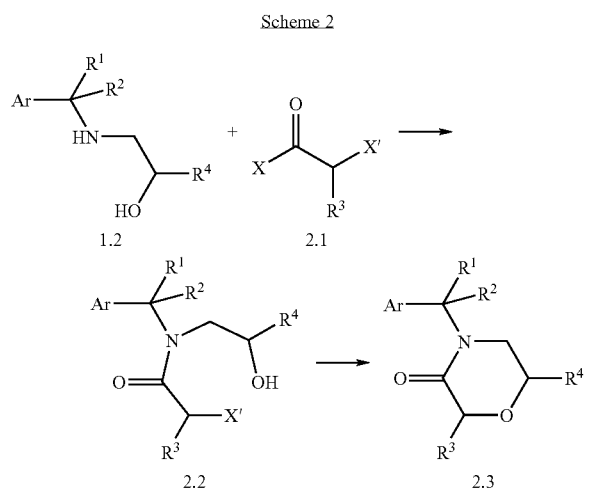

Scheme 2 shows a synthesis of the compounds of Formula (I) where, for illustrative purposes, L is —CH$_2$O— and p is 1. Amino alcohol 1.2 is reacted under acylation conditions with compound 2.1 where X and X' are leaving groups such as chlorine and R$^3$ is as previously defined to give amide 2.2. Exposure of 2.2 to basic conditions such as CsCO$_3$ and optionally in the presence of catalytic TBAI (t-butyl ammonium iodide) in DMF gives lactam 2.3.

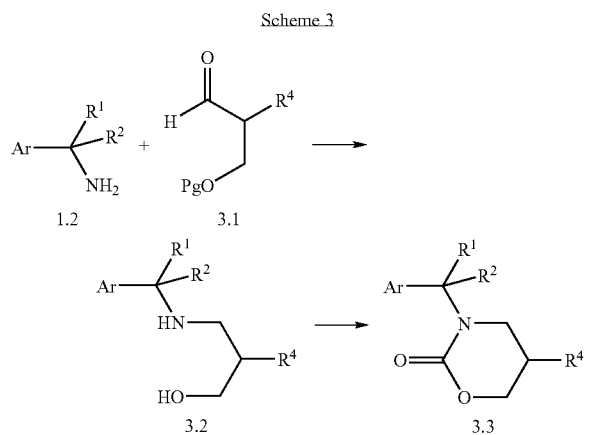

Scheme 3 shows a synthesis of the compounds of Formula (I) where, for illustrative purposes, L is —OCH$_2$—. Amine 1.2 is reacted under reductive amination conditions with aldehyde 3.1, where Pg is an oxygen protecting group and R$^4$ is as previously defined for Formula (I) to give the corresponding amine. Suitable reductive amination conditions include condensation of 1.2 and 3.1 in methylene chloride followed by reduction of the imine with a borohydride such sodium triacetoxyborohydride. Removal of the oxygen protecting group from the resulting amine gives amino alcohol 3.2. Reaction of 3.2 with phosgene or a phosgene equivalent under cyclization conditions gives the six-membered carbamate 3.3.

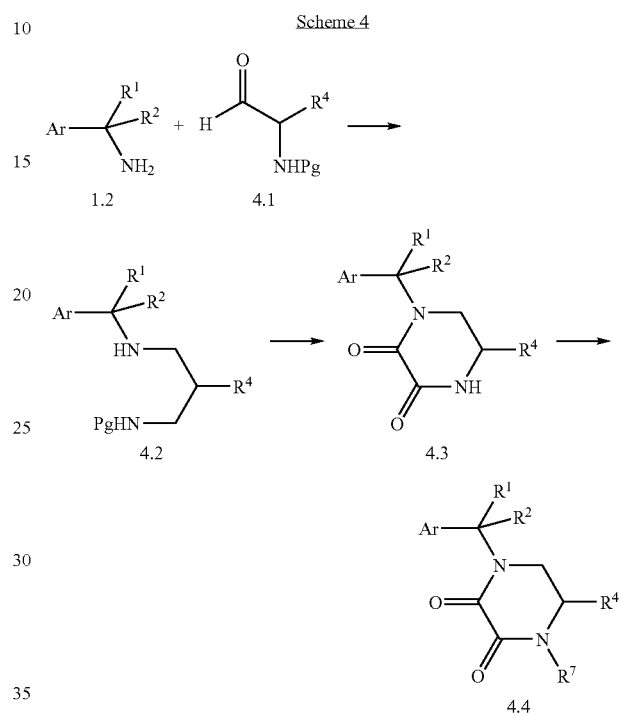

Scheme 4 shows a synthesis of the compounds of Formula (I) where, for illustrative purposes, L is —C(O) NR$^7$—. Amine 1.2 is reacted under reductive amination conditions with aldehyde 4.1 where Pg is a nitrogen protecting group such as Boc and R$^4$ is as previously defined for Formula (I) to give the corresponding amine 4.2. Suitable reductive amination conditions include condensation of 1.2 and 4.1 in methylene chloride followed by reduction of the imine with a borohydride such sodium triacetoxyborohydride. Amine 4.2 is reacted with oxalyl chloride ClC(O)C(O)Cl in the presence of triethyl amine to give the corresponding amide. Isolation of the intermediate amide and removal of the protecting group followed by heating gives the cyclized di-keto compound 4.3, that can then be functionalized to form 4.4 using known procedures. Such methods include alkylation of the amine with an alkyl halide or reaction with an alkyl sulfonyl halide to give the corresponding sulfonamide.

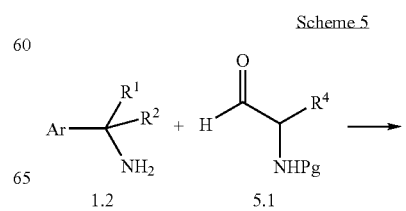

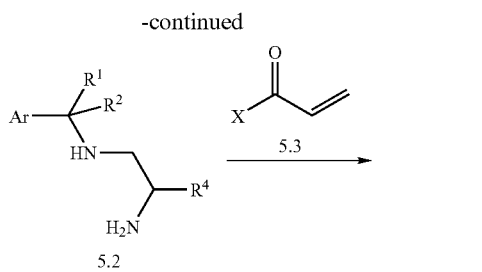

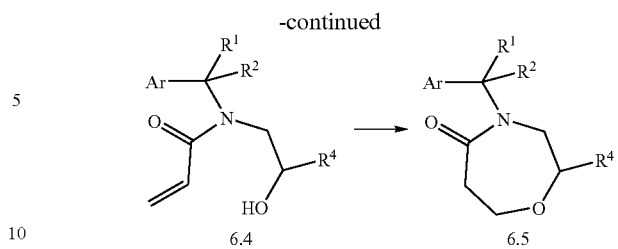

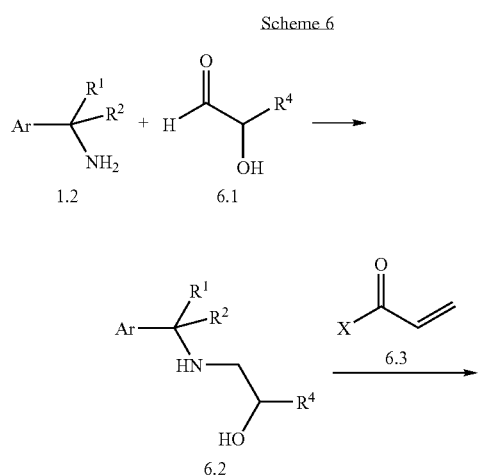

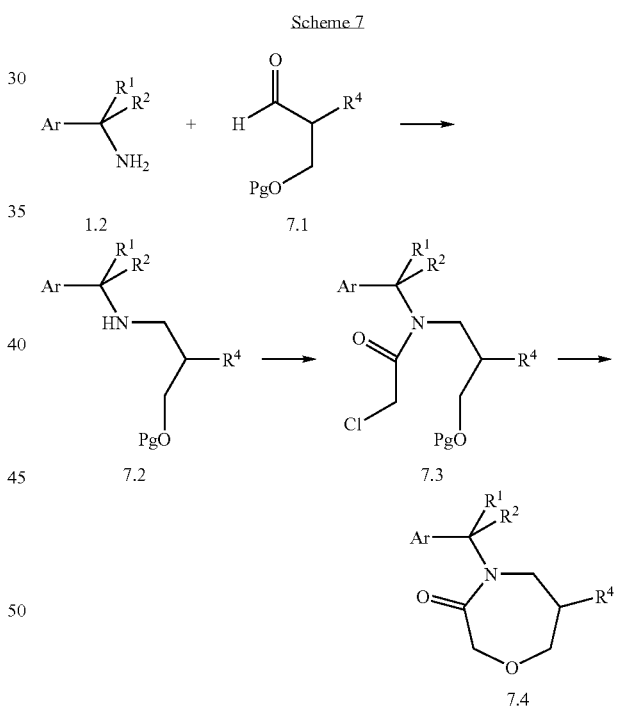

Scheme 5 shows a synthesis of the compounds of Formula (I) where, for illustrative purposes, L is —$CH_2CH_2NR^7$—. Amine 1.2 is reacted under reductive amination conditions with aldehyde 5.1 where Pg is a nitrogen protecting group such as Boc and $R^4$ is as previously defined for Formula (I) to give the corresponding amine. Suitable reductive amination conditions include condensation of 1.2 and 5.1 in methylene chloride followed by reduction of the imine with a borohydride such sodium triacetoxyborohydride. Removal of the protecting group gives 5.2 that is then reacted with 5.3 where X is a leaving group such as chlorine. The resulting amide intermediate is next treated with acid such as trifluoroacetic acid to give the Michael addition product 5.4. Functionalization of 5.4 using known procedures gives 5.5. Such methods include alkylation of the amine with an alkyl halide or reaction with an alkyl sulfonyl halide to give the corresponding sulfonamide.

Scheme 6 shows a synthesis of the compounds of Formula (I) where, for illustrative purposes, L is —$CH_2CH_2O$—. Amine 1.2 is reacted under reductive amination conditions with aldehyde 6.1, where $R^4$ is as previously defined for Formula (I), to give the corresponding amine 6.2. Suitable table reductive amination conditions include condensation of 1.2 and 6.1 in methylene chloride followed by reduction of the imine with a borohydride such sodium triacetoxyborohydride. Amine 2.2 is reacted with the acrolein compound 6.3 where X is a leaving group such as chlorine to give the corresponding amide 6.4. Reaction of 6.4 with a mercuric acetate such as mercuric trifluoroacetate followed by sodium borohydride under cyclization conditions gives 6.5.

Scheme 7 shows a synthesis of the compounds of Formula (I) where, for illustrative purposes, L is —$CH_2OCH_2$—. Amine 1.2 is reacted under reductive amination conditions with aldehyde 7.1, where Pg is an oxygen protecting group and $R^4$ is as previously defined for Formula (I), to give the corresponding amine. Suitable reductive amination conditions include condensation of 1.2 and 7.1 in methylene chloride followed by reduction of the imine with a borohydride such sodium triacetoxyborohydride. Amine 7.2 is reacted with chloroacetyl chloride to give the corresponding amide 7.3. Removal of the protecting group from 7.3 and exposure of the resulting alcohol to cyclization conditions such as CsCO₃ and optionally catalytic TBAI (t-butyl ammonium iodide) in DMF gives lactam 7.4.

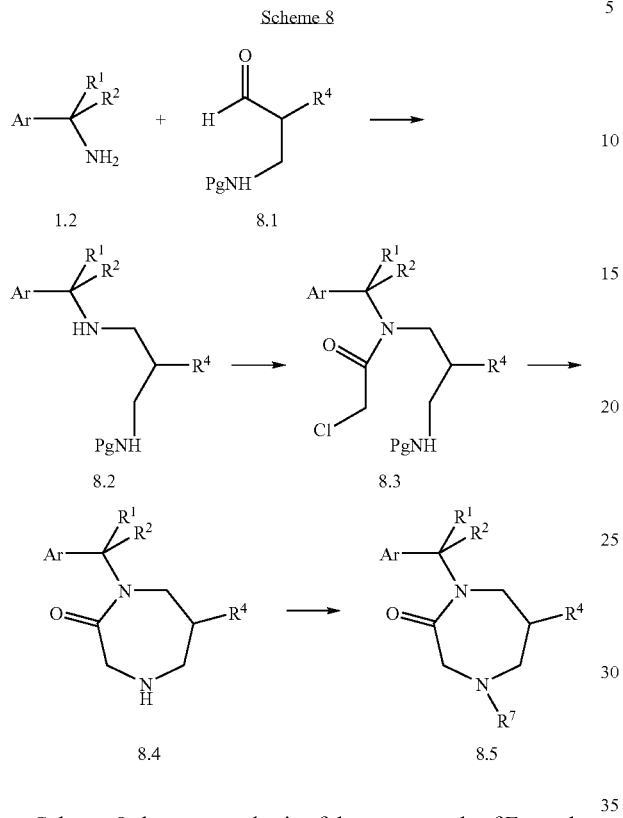

Scheme 8 shows a synthesis of the compounds of Formula (I) where, for illustrative purposes, L is —CH₂NR⁷CH₂—. Amine 1.2 is reacted under reductive amination conditions with aldehyde 8.1 where Pg is a nitrogen protecting group such as Boc and R⁴ is as previously defined for Formula (I) to give the corresponding amine 8.2. Suitable reductive amination conditions include condensation of 1.2 and 8.1 in methylene chloride followed by reduction of the imine with a borohydride such sodium triacetoxyborohydride. Amine 8.2 is reacted with chloroacetyl chloride to give the corresponding amide 8.3. Removal of the protecting group from 8.3 and exposure of the resulting amine to cyclization conditions such as heating in a polar solvent gives lactam 8.4 that can then be further functionalized to form 8.5 using known procedures. Such methods include alkylation of the amine with an alkyl halide or reaction with an alkyl sulfonyl halide to give the corresponding sulfonamide.

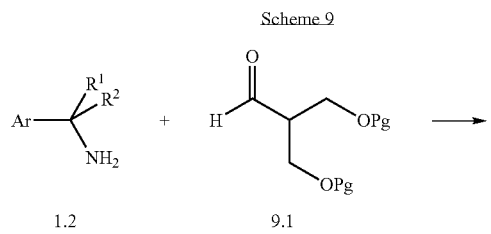

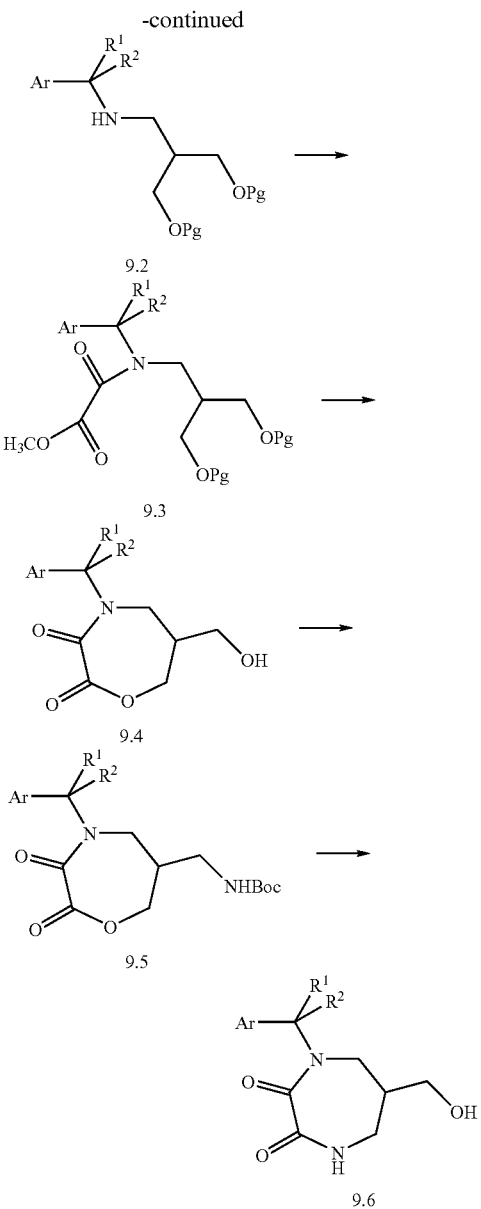

Scheme 9 shows a synthesis of the compounds of Formula (I) where, for illustrative purposes, L is —C(O)NR⁷CH₂— and R⁴ is CH₂OH. Amine 1.2 is reacted under reductive amination conditions with aldehyde 9.1 where Pg is an oxygen protecting group to give the corresponding amine 9.2. Suitable reductive amination conditions include condensation of 1.2 and 9.1 in methylene chloride followed by reduction of the imine with a borohydride such sodium triacetoxyborohydride. Amine 9.2 is reacted with methyl-2-chloro-2-oxoacetate to give the corresponding amide 9.3. Removal of the protecting groups from 9.3 and exposure of the resulting diol to cyclization conditions such as CsCO₃ and optionally catalytic TBAI (t-butyl ammonium iodide) in DMF gives lactam 9.4. Treatment of 9.4 with PPh₃, diisopropylazodicarboxylate (DIAD), and (EtO)₂P(O)NHBoc under Mitsunobu conditions gives the protected amine 9.5. Removal of the protecting group such as by exposure to acidic conditions gives the rearranged diketo compound 9.6 that can be further functionalized to give additional compounds of Formula (I).

In another embodiment, provided is a method for preparing a free base of a compound of Formula (I) or (Ia)-(Ii) comprising reacting an acid addition salt of the compound with a base to form the corresponding free base.

In another embodiment, provided is a method for preparing a salt of a compound of Formula (I) or (Ia)-(Ii) comprising:

a) reacting a free base of a compound of Formula (I) or (Ia)-(Ii) with an acid to give an acid addition salt; or b) converting a salt of a compound of Formula (I) or (Ia)-(Ii) to another salt of a compound of Formula (I) or (Ia)-(Ii).

D. Pharmaceutical Formulations

When employed as pharmaceuticals, the compounds of the subject invention are usually administered in the form of pharmaceutical compositions. These compositions can be administered by a variety of routes including oral, parenteral, transdermal, topical, rectal, and intranasal. These compounds are effective, for example, as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, cancer in mammals, the compounds or pharmaceutical compositions thereof will be administered by any appropriate route, such as orally, topically, transdermally, and/or parenterally at a dosage to obtain and maintain a concentration, that is, an amount, or blood-level of active component in the mammal undergoing treatment that will be therapeutically effective. Generally, such therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%)/ Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
| --- | --- |
| Active Ingredient | 5.0 mg |
| Corn Oil | 1.0 mL |

FORMULATION EXAMPLE 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

An intravenous formulation may be prepared as follows:

| Ingredient | Quantity |
| --- | --- |
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mack Publishing Company, Philadelphia, Pa., 17th ed. (1985).

E. Dosage and Administration

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds of the instant invention are useful for inhibiting or treating a disorder mediated, at least in part, by the activity of KSP. In one aspect, the disorder that is mediated, at least in part by KSP, is a cellular proliferative disorder. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or mammalian subject in need of such treatment, comprising administering to the subject a therapeutically effective amount of a compound of Formula (I) or (Ia)-(Ii), either alone or in combination with other anticancer agents. In other aspects provided are uses of a compound of Formula (I) or (Ia)-(Ii) in the preparation of a medicament for use in treating a KSP mediated disorder.

The compounds of the present invention are also useful in assays evaluating relative activity of KSP kinesin inhibition. In such assays a compound of Formula (I) or (Ia)-(Ii) can be used to determine relative inhibitory activity of a test compound such as another compound of Formula (I) or (Ia)-(Ii) or another KSP inhibitor. When so employed, the compound of Formula (I) or (Ia)-(Ii) is employed in an amount sufficient to allow the skilled artisan to detect inhibition of the KSP kinesin. Such an amount is sometimes referred to herein as an "effective inhibitory amount." In a preferred embodiment the inhibitory amount is an amount that will reduce KSP kinesin activity by approximately 50% as compared to the activity in the absence of a compound of Formula (I) or (Ia)-(Ii). Test compounds can then be evaluated as providing greater or lesser inhibition at the same concentration so as to provide a ranking of relative activity. Such information is useful in determining structural changes and other modifications to the test compound to improve its activity. Accordingly the present invention provides a method for inhibiting the activity of KSP kinesin which method comprises contacting said kinesin with an effective inhibitory amount of a compound of Formula (I) or (Ia)-(Ii). Also provided is a method for inhibiting the activity of KSP kinesin in a cell, which method comprises contacting said cell with an effective inhibitory amount of a compound of Formula (I) or (Ia)-(Ii).

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas, sarcomas, and hematological malignancies.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound or composition of this invention may be administered to a mammal by a suitable route, such as orally, intravenously, parenterally, transdermally, topically, rectally, or intranasally.

Mammals include, for example, humans and other primates, pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-1), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 5 μg to about 50 mg per kilogram body weight per day, preferably about 1 mg to about 10 mg per kilogram body weight per day. In the alternative, for intravenous administration, the dose will typically be in the range of about 5 μg to about 50 mg per kilogram body weight, preferably about 500 μg to about 5000 μg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LC/MS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GC/MS analysis is performed on a Hewlett Packard instrument (HP6890 Series gas chromatograph with a Mass Selective Detector 5973; injector volume: 1 mL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices MeI-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, EtOAc, hexane, acetone, aqueous hydroxyamine and triethyl amine. Typical solvents employed for the reverse phase HPLC were varying concentrations of acetonitrile and water with 0.1% trifluoroacetic acid.

Unless otherwise stated all temperatures are in degrees Celsius. Also, in these examples and elsewhere, abbreviations have the following meanings:

AcOH=acetic acid
aq.=aqueous
ATP=adenosine triphosphate
Boc=tert-butyloxycarbonyl
BSA=bovine serum albumin
CAM=ceric ammonium molybdate
DCM=dichloromethane
DIAD=diisopropyl azodicarboxylate
DIBAL=diisobutylaluminum hydride
DIEA=diisopropylethylamine
DIPEA=diisopropylethylamine
DMAP=dimethylaminopyridine
DMF=dimethylformamide
DMSO=dimethylsulfoxide
DTT=dithiothreitol
eq.=equivalents
Et$_2$O=diethyl ether
Et$_3$N=triethyl amine
EtOAc=ethyl acetate
EtOH=ethanol
g=gram
h=hour
HPLC=high performance liquid chromatography
L=liter
LC/MS=liquid chromatography/mass spectroscopy
M=molar
m=meter
m/z=mass/charge ratio
MeNH$_2$=methyl amine
mg=milligram
min=minute
mL=milliliter
mm=millimeter
mM=millimolar
mmol=millimole
mol=mole
N=normal
nm=nanometer
nM=nanomolar
NMR=nuclear magnetic resonance
PPh$_3$=triphenyl phosphine
PhCF$_3$=trifluoromethylbenzene
psi=pounds per square inch
RT=room temperature
sat.=saturated
TEA=triethylamine
THF=tetrahydrofuran
TFA=trifluoroacetic acid
TLC=thin layer chromatography
TMS=trimethylsilyl
TMSCl=trimethylsilyl chloride
Yb(OTf)$_3$=Ytterbium (III) trifluoromethanesulfonate
μG=microgram
μL=microliter
μM=micromolar Example 1

(R)-1-(1-benzyl-4-phenyl-1H-imidazol-2-yl)-2,2-dimethylpropan-1-amine (1-5)

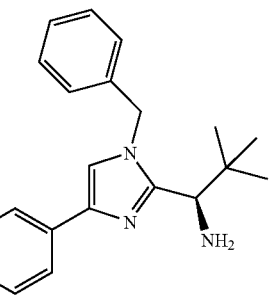

Step A

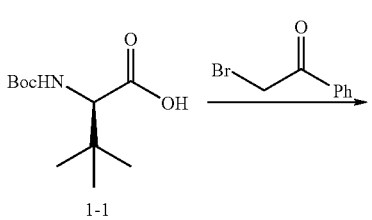

A stirred solution of the appropriate N-Boc-acid (4.0 mmol), e.g., tert-butyl leucine 1-1, in EtOH (10 mL) was treated with Cs$_2$CO$_3$ (2.0 mmol). After 45 min, the EtOH was removed by evaporation under reduced pressure. The residual cesium salt was re-dissolved in DMF (15 mL) and then treated with the appropriate α-halo-ketone, e.g., 2-bromoacetophenone (4.0 mmol) and stirred at RT until the reaction was complete. The reaction mixture was then partitioned between EtOAc and H$_2$O, and the organics separated, then washed with H$_2$O (×3), brine (×3), then dried (Na$_2$SO$_4$), filtered, and evaporated under reduced pressure to give the keto ester 1-2 which was pure enough to use directly in the next step.

Step B

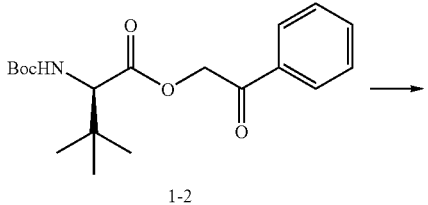

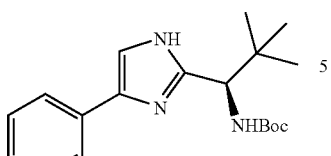

1-3

To a stirred solution of keto-ester 1-2 (4.0 mmol) in xylenes (40 mL) was added ammonium acetate (20 mmol). A Dean-Stark trap was added and the reaction heated to 140° C. Once the reaction was complete, the mixture was allowed to cool to RT, then partitioned between EtOAc and sat. aq. NaHCO₃. The organics were separated, then washed with sat. aq. NaHCO₃ (×2), H₂O (×3), brine (×3), then dried (Na₂SO₄), filtered, and evaporated under reduced pressure to give the phenyl imidazole 1-3 which was pure enough to use directly in the next step.

Step C

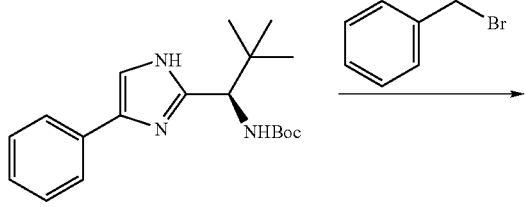

1-3

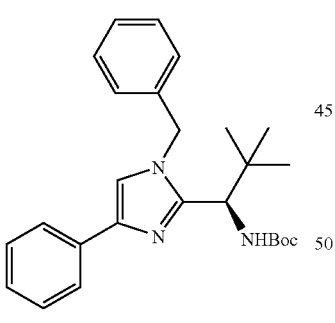

1-3

To a stirred solution/suspension of imidazole 1-3 (4.0 mmol) and K₂CO₃ (8.0 mmol) in DMF (10 mL) was added the benzylating agent, e.g., benzyl bromide (4.40 mmol). Once the reaction was complete, the mixture was partitioned between EtOAc and H₂O. The organic layer was separated and washed with H₂O (×3), brine (×3), then dried (Na₂SO₄), filtered, and evaporated under reduced pressure to give the crude benzylated phenyl imidazole. The crude reaction material was then crystallized (EtOAc, hexanes) to give pure product 1-4.

Step D

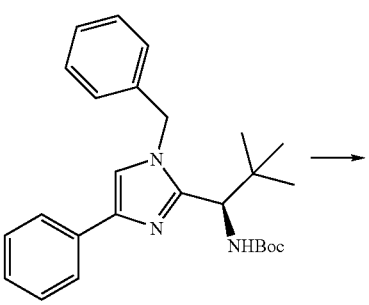

1-4

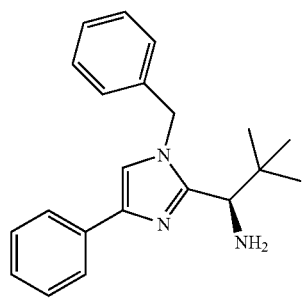

1-5

Boc-protected amine 1-4 (1.0 mmol) was treated with 10% TFA in DCM (5 mL). Once reaction was complete, the reaction mixture was concentrated in vacuo and then partitioned between EtOAc and sat. aq. NaHCO₃. The organics were separated, then washed with sat. aq. NaHCO₃ (×2), H₂O (×2), brine (×2), then dried (Na₂SO₄), filtered, and evaporated under reduced pressure to give the phenyl imidazole free amine 1-5.

Example 2

(R)-1-(1-benzyl-4-(2,5-difluorophenyl)-1H-imidazol-2-yl)-2,2-dimethylpropan-1-amine (2-6)

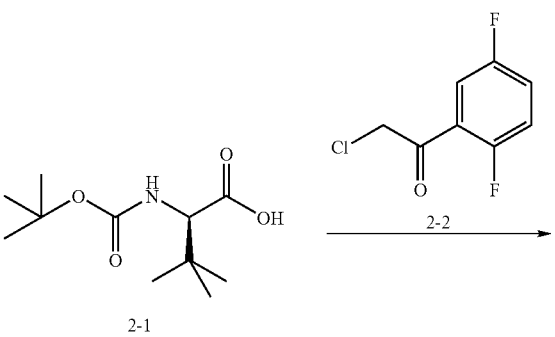

2-1     2-2

-continued

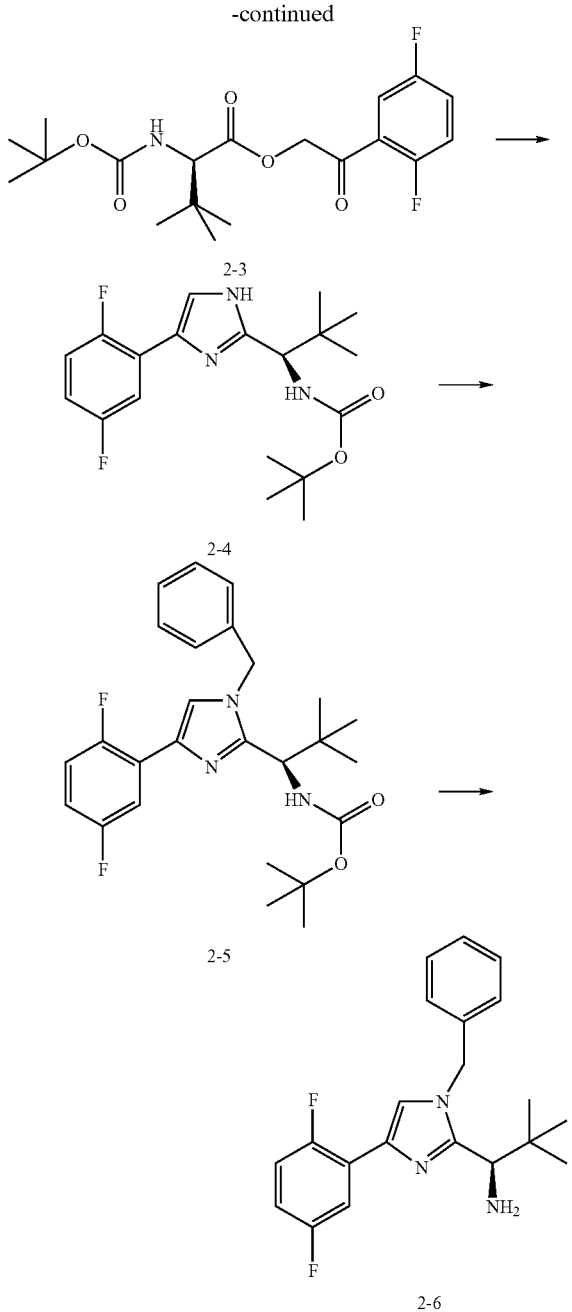

Step A: Preparation of Compound 2-3

To a 5-necked flask containing 1 eq. of Compound 2-1 was added 0.7 eq. of $K_2CO_3$ to give a 0.25M solution of $K_2CO_3$ in acetone. After being stirred under $N_2$ for 45 minutes, 1.0 eq. of Compound 2-2 in 1 M of acetone was added followed by addition of 0.2 eq. of KI in 5 M acetone. When the reaction is completed (about 3 hours), the reaction mixture was cooled with an ice bath. Ice water (equal to approximately 2.5× volume of acetone used in reaction) was added via addition funnel at such a speed that the temperature did not exceed 15° C. After being stirred in an ice bath for one hour, the product was collected by vacuum filtration. The filter cake was washed 3 times with 20% acetone and 3 times with water. The filter cake was air-dried and further dried in an oven at 50° C./5 torr until a consistent weight is reached. Yield 92.7 g (96%). HPLC purity: 99%.

Step B: Preparation of Compound 2-4

To a 0.19 M toluene solution of 2-3 in a reaction flask was added 20 eq. of $NH_4OAc$. The mixture was stirred under reflux until the reaction was completed (about 8 h). It was cooled to RT and then water (equal to approximately one fourth of the volume of toluene used in the reaction) was added. The organic phase was separated and washed with water, sat. $NaHCO_3$, and dried over $MgSO_4$. The solvent was removed in vacuo to give 2-4. Yield: 59.50 g (99.6%). HPLC purity: 91.4%.

Step C: Preparation of Compound 2-5

A flask containing a 0.5 M DMF and $K_2CO_3$ solution of 2-4 was stirred under $N_2$ for 30 min at 0-5° C., and then 1.1 eq. of $PhCH_2Br$ was added to it. The mixture was then stirred at RT overnight. It was then stirred in an ice bath during which ice water (approximately equal to the volume of DMF used in the reaction) was added dropwise. The product was collected by vacuum filtration, washed twice with 50% DMF, twice with 25% DMF and three times with water. The solid was dried in an oven at 50° C./5 torr. Yield: 69.20 g (95%). HPLC purity: 94%.

Step D: Preparation of Compound 2-6

MeOH was added to a flask and placed in an ice bath. To this was added 9.85 eq. of $CH_3COCl$ dropwise over 30 min. followed by 1 eq. of 2-5 to form a 0.25M solution of 2-5 in MeOH. The mixture was stirred at RT until the reaction was completed (about 12 h). After removing the solvent under reduced pressure, the obtained solid was suspended in MeOH (equal to approximately one half of the volume of MeOH used in the reaction) and stirred at 0-5° C. To this mixture were added 2.5 M NaOH/MeOH solution dropwise until the pH reached about 10 and water was then added. After being stirred at 0-5° C. for 1 h, the product 2-6 was collected by filtration. It was dried in an oven at 50° C./5 torr. Yield: 26.12 g (90.5%). HPLC purity: 97.0%. Optical purity was determined to be >99% (enantiomeric excess (ee)).

Example 3

(5R)-5-(2-aminoethyl)-3-[(1R)-1-(1-benzyl-4-phenyl-1H-imidazol-2-yl)-2,2-dimethylpropyl]-1,3-oxazolidin-2-one (1) and (5R)-5-(2-aminoethyl)-3-[(1R)-1-(1-benzyl-4-phenyl-1H-imidazol-2-yl)-2,2-dimethylpropyl]-1,3-oxazolidin-2-one (2)

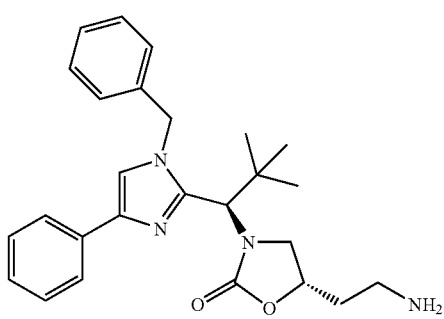

1

-continued

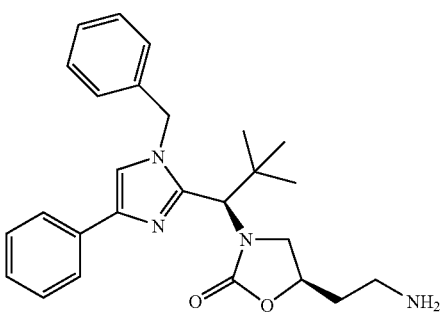

Step A

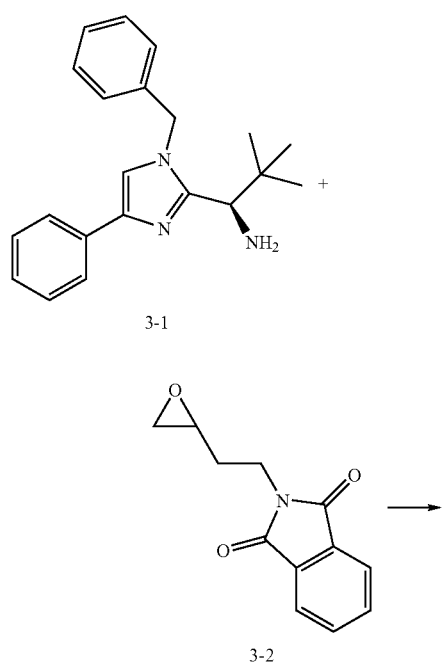

3-1

3-2

3-3

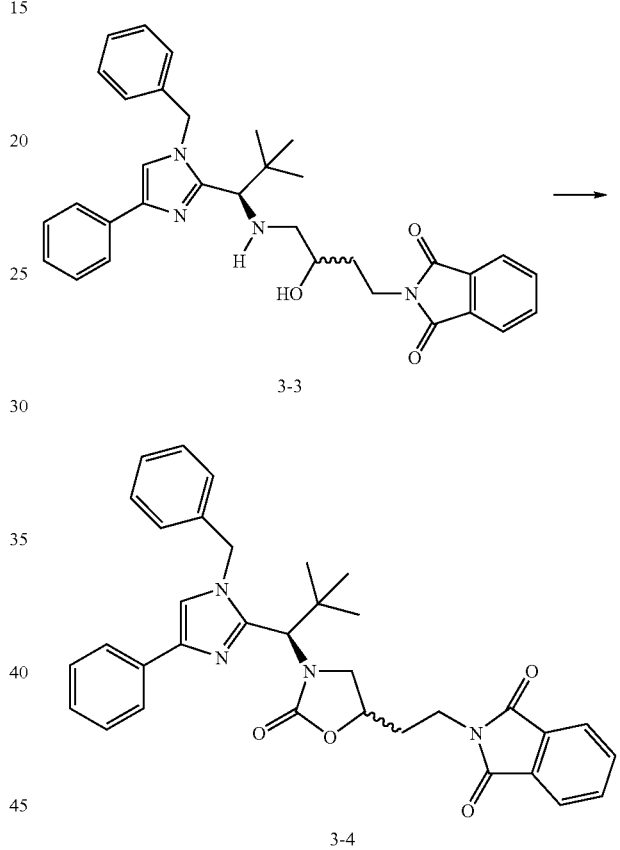

To a solution of amine 3-1 (1 eq.) in methylene chloride at room temperature was added epoxide 3-2 (1 eq.) followed by Yb(OTf)$_3$ (1 eq.). Reaction was heated at 40° C. for 14 hrs. After complete reaction, EtOAc was added followed by washing with water (2×). Organics were dried over sodium sulfate, filtered, and concentrated. Crude product was purified on silica gel with 0-100% EtOAc/Hexane gradient elution to provide compound 3-3.

Step B 3-3

3-4

To a solution of amine 3-3 (1 eq.) in methylene chloride at room temperature was added phosgene solution (1.1 eq.) followed by triethylamine (20 eq.). Reaction was heated at 30° C. until complete cyclization was observed. The reaction was washed with water and organic layer separated, dried, concentrated and purified on silica gel with 0-100% EtOAc/Hexane gradient elution to provide compound 3-4.

Step C

To a solution of phthalamide 3-4 (1 eq.) in EtOH was added hydrazine (25 eq.) at room temperature. Reaction was heated at 60° C. Upon completion, the cooled reaction was filtered and concentrated. The resulting oil was purified by reverse phase HPLC to provide the desired compounds 1 and 2; MH+ 433.2.

Example 4

5-(aminomethyl)-3-{(1R)-1-[1-benzyl-4-(3-chlorophenyl)-1H-imidazol-2-yl]-2-methylpropyl}-1,3-oxazolidin-2-one (3)

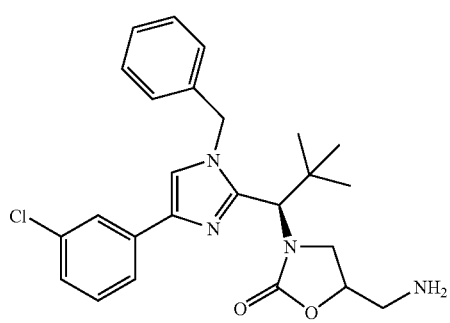

Step A

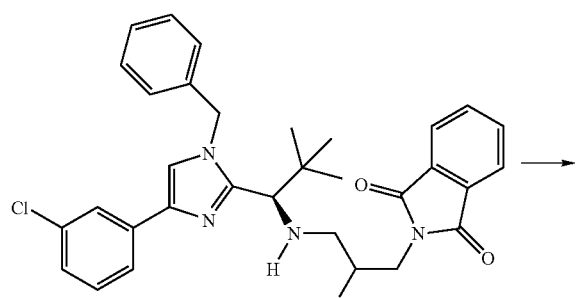

4-1

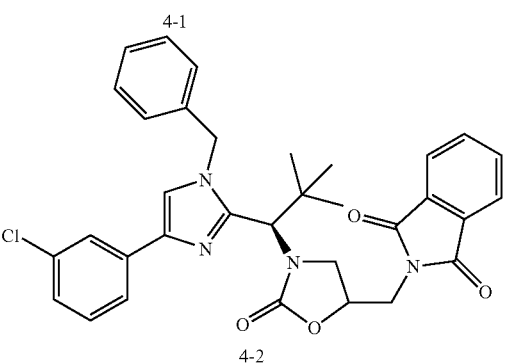

4-2

To a solution of 4-1 amine (1 eq.; prepared in a similar manner as in Examples 1 and 3) in methylene chloride at room temperature was added phosgene solution (1.1 eq.) followed by triethylamine (20 eq.). Reaction was heated at 30° C. until complete cyclization was observed. The reaction was washed with water and organic layer separated, dried, concentrated and purified on silica gel with 0-100% EtOAc/Hexane gradient elution to provide compound 4-2.

Step B

To a solution of phthalamide 4-2 (1 eq.) in EtOH was added hydrazine (25 eq.) at room temperature. Reaction was heated at 60° C. Upon completion, the cooled reaction was filtered and concentrated. The resulting oil was purified by reverse phase HPLC to provide the desired compound 3; MH+ 439.2.

Example 5

(5S)-5-(aminomethyl)-3-[(1R)-1-(1-benzyl-4-phenyl-1H-imidazol-2-yl)-2,2-dimethylpropyl]-1,3-oxazinan-2-one (4) and (5R)-5-(aminomethyl)-3-[(1R)-1-(1-benzyl-4-phenyl-1H-imidazol-2-yl)-2,2-dimethylpropyl]-1,3-oxazinan-2-one (5)

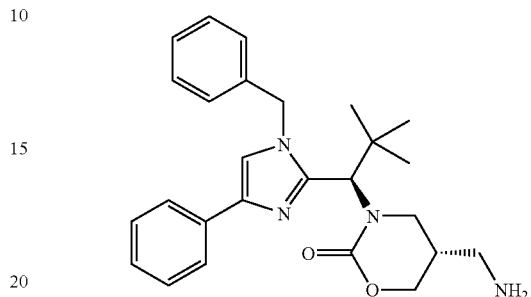

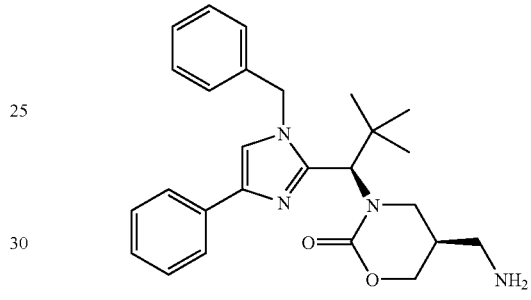

Step A

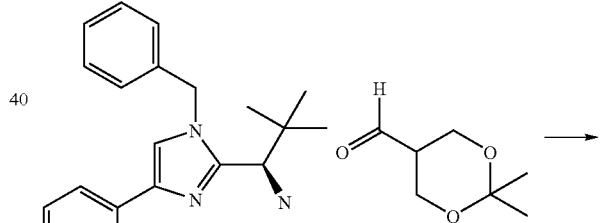

1-5     5-1

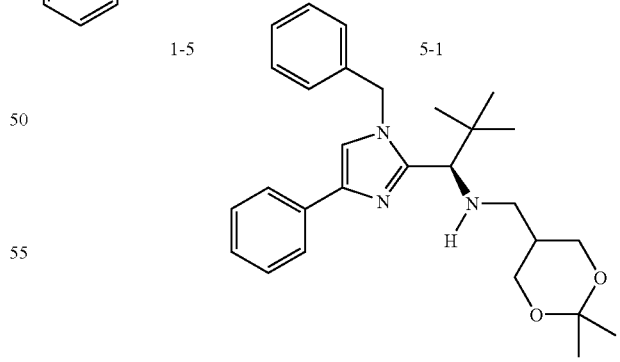

5-2

To a solution of amine 1-5 and aldehyde 5-1 (1.1 eq.) in methylene chloride at room temperature was added sodium triacetoxyborohydride (5 eq.) in portions. The reaction stirred for 12 hours and was quenched with water. The organic layer was separated, dried with magnesium sulfate, filtered and concentrated. The resulting residue was purified on silica gel with 0-100% EtOAc/Hexane gradient elution to provide compound 5-2.

Step B

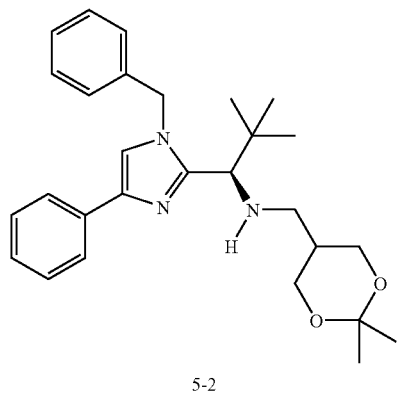

5-2

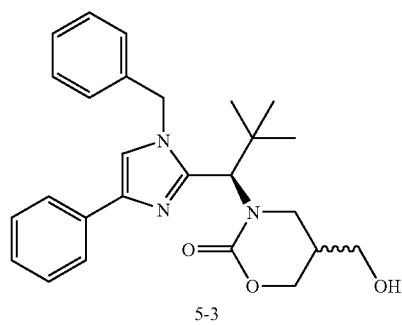

5-3

To a solution of amine 5-2 (1 eq.) in methylene chloride at room temperature was added phosgene solution (1.1 eq.) followed by triethylamine (20 eq.). Reaction was heated at 30° C. until complete cyclization was observed. The reaction was washed with water and organic layer separated, dried, concentrated and purified on silica gel with 0-100% EtOAc/Hexane gradient elution to provide compound 5-3.

Step C

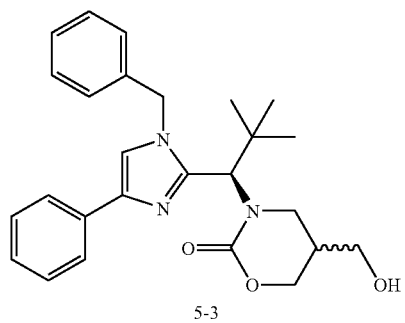

5-3

-continued

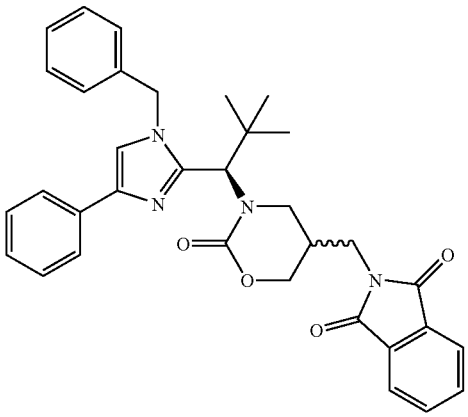

5-4

To a solution of alcohol 5-3 (1 eq.) in THF was added resin bound PPh₃ (2 eq.) followed by stirring at room temperature for 10 minutes. To this reaction were then added phthalamide (2 eq.) and DIAD (2 eq.). Reaction was heated at 40° C. for 30 minutes and upon cooling was diluted with EtOAc, filtered through a plug of Celite, concentrated and purified by reverse phase HPLC to provide compound 5-4.

Step D

To a solution of phthalamide 5-4 (1 eq.) in EtOH was added hydrazine (25 eq.) at room temperature. Reaction was heated at 60° C. Upon completion, the cooled reaction was filtered and concentrated. The resulting oil was purified by reverse phase HPLC to provide the desired compound 4 and 5; MH+ 433.2.

Example 6

(6S)-6-(aminomethyl)-4-[(1R)-1-(1-benzyl-4-phenyl-1H-imidazol-2-yl)-2,2-dimethylpropyl]morpholin-3-one (6) and (6R)-6-(aminomethyl)-4-[(1R)-1-(1-benzyl-4-phenyl-1H-imidazol-2-yl)-2,2-dimethylpropyl]morpholin-3-one (7)

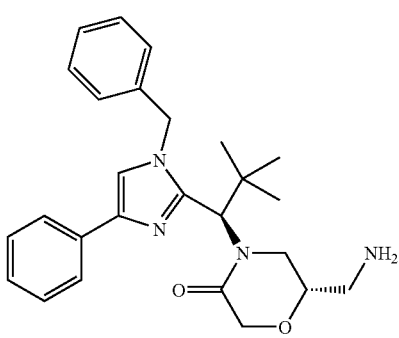

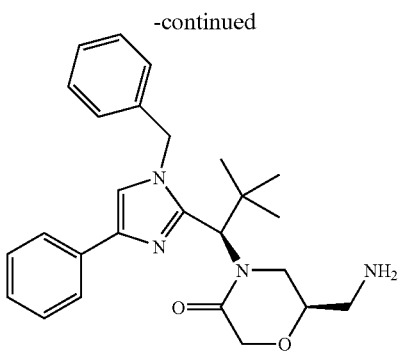

Step A

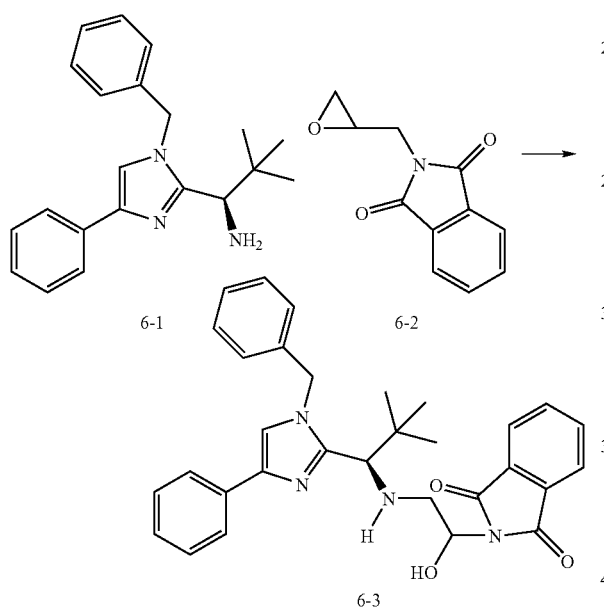

To a solution of amine 6-1 (1 eq.) in methylene chloride at room temperature was added epoxide 6-2 (1 eq.) followed by Yb(OTf)$_3$ (1 eq.). Reaction was heated at 40° C. for 14 hrs. After complete reaction, EtOAc was added followed by washing with water (2×). Organics were dried over sodium sulfate, filtered and concentrated. Crude product was purified on silica gel with 0-100% EtOAc/Hexane gradient elution to provide compound 6-3.

Step B

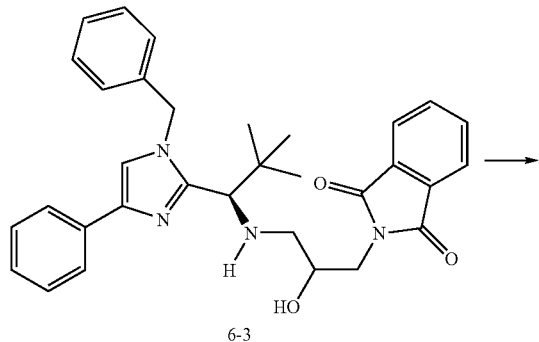

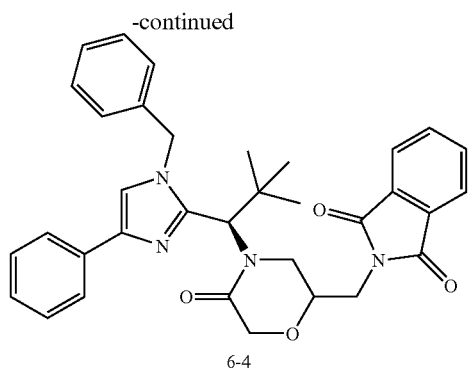

To a solution of amine 6-3 (1 eq.) in methylene chloride at 0° C. was added triethylamine (3 eq.) followed by chloroacetyl chloride (1.5 eq.). Reaction was allowed to stir at room temperature until complete whereupon the solution was quenched with water followed by methylene chloride extractions. Combined organics were dried over sodium sulfate, filtered and concentrated. Crude product was purified on silica gel with 0-100% EtOAc/Hexane gradient elution to provide the intermediate amide compound. To a DMF solution of the amide was added CsCO$_3$ (1 eq.) and TBAI (catalytic). Reaction was heated at 50° C. for 5 hours and upon completion was quenched by addition of sodium bicarbonate (saturated aq.) followed by EtOAc extraction (3×). Combined organics were dried over sodium sulfate, filtered and concentrated. Crude product was purified on silica gel with 0-100% EtOAc/Hexane gradient elution to provide compound 6-4.

Step C

To a solution of phthalamide 6-4 (1 eq.) in EtOH was added hydrazine (25 eq.) at room temperature. Reaction was heated at 60° C. Upon completion, the cooled reaction was filtered and concentrated. The resulting oil was purified by reverse phase HPLC to provide the desired compounds 6 and 7; MH+ 433.2.

Example 7

(6R)-6-(aminomethyl)-4-{(1R)-1-[1-benzyl-4-(3-chlorophenyl)-1H-imidazol-2-yl]-2-methylpropyl}morpholin-3-one (8) and (6S)-6-(aminomethyl)-4-{(1R)-1-[1-benzyl-4-(3-chlorophenyl)-1H-imidazol-2-yl]-2-methylpropyl}morpholin-3-one (9)

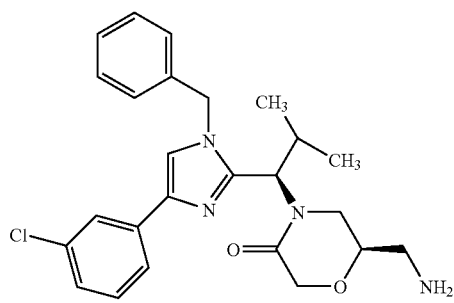

-continued

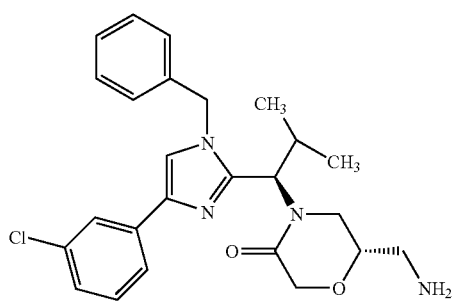

Compounds 8 and 9 were prepared in a similar manner as example 6; MH+ 453.2

Example 8

(6R)-6-(2-aminoethyl)-4-[(1R)-1-(1-benzyl-4-phenyl-1H-imidazol-2-yl)-2,2-dimethylpropyl]morpholin-3-one (10) and (6S)-6-(2-aminoethyl)-4-[(1R)-1-(1-benzyl-4-phenyl-1H-imidazol-2-yl)-2,2-dimethylpropyl]morpholin-3-one (11)

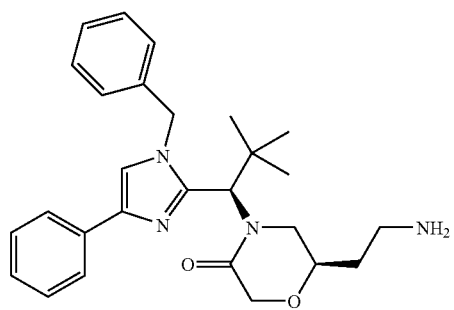

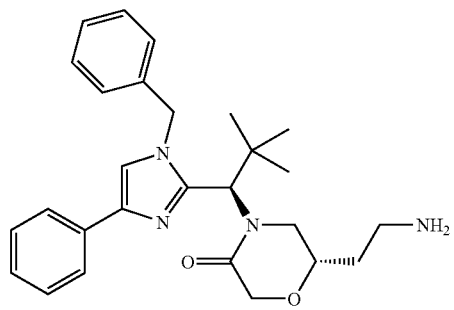

Compounds 10 and 11 were prepared in a similar manner as example 6; MH+ 447.3.

Example 9

(6S)-6-(2-aminoethyl)-4-{(1R)-1-[1-benzyl-4-(3-chlorophenyl)-1H-imidazol-2-yl]-2-methylpropyl}morpholin-3-one (12) and (6R)-6-(2-aminoethyl)-4-{(1R)-1-[1-benzyl-4-(3-chlorophenyl)-1H-imidazol-2-yl]-2-methylpropyl}morpholin-3-one (13)

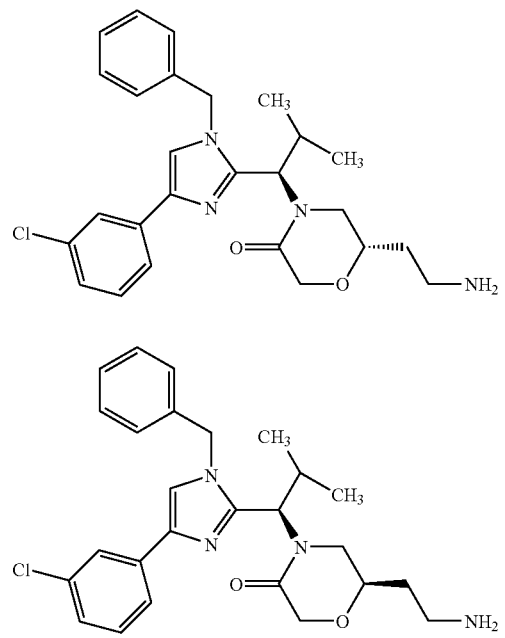

Compounds 12 and 13 were prepared in a similar manner as example 6; MH+ 467.2.

Example 10

(2S,6R)-6-(aminomethyl)-4-{(1R)-1-[1-benzyl-4-(3-fluorophenyl)-1H-imidazol-2-yl]-2,2-dimethylpropyl}-2-methylmorpholin-3-one (14) and (2R,6R)-6-(aminomethyl)-4-{(1R)-1-[1-benzyl-4-(3-fluorophenyl)-1H-imidazol-2-yl]-2,2-dimethylpropyl}-2-methylmorpholin-3-one (15)

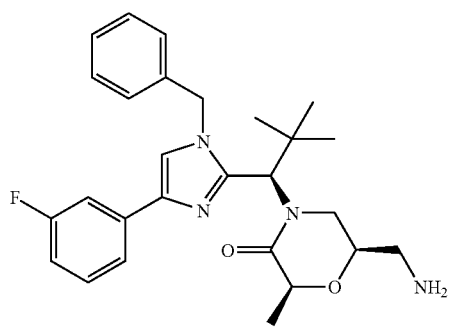

-continued

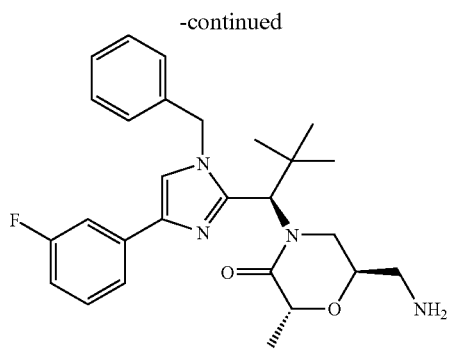

Step A

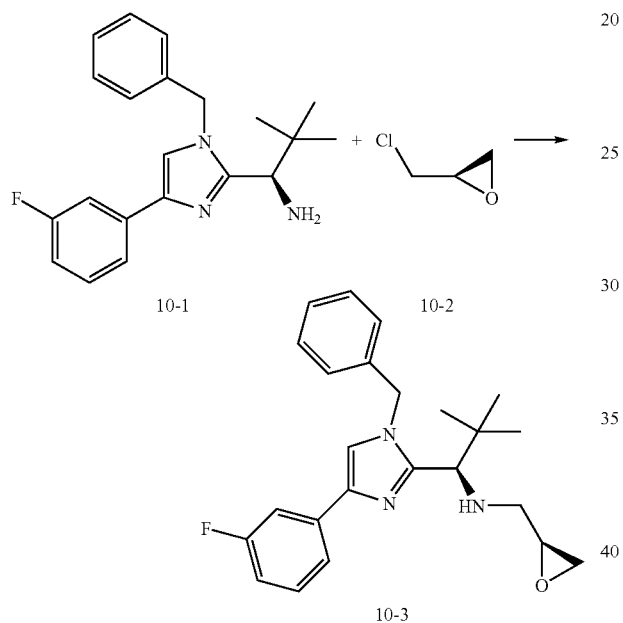

To a solution of amine 10-1 and epichlorohydrin 10-2 in methylene chloride was added Yb(OTf)₃ at room temperature. Reaction was heated to 45° C. until consumption of starting materials was complete. Reaction was concentrated and resulting residue was purified on silica gel with 0-100% EtOAc/Hexane gradient elution to provide compound 10-3.

Step B

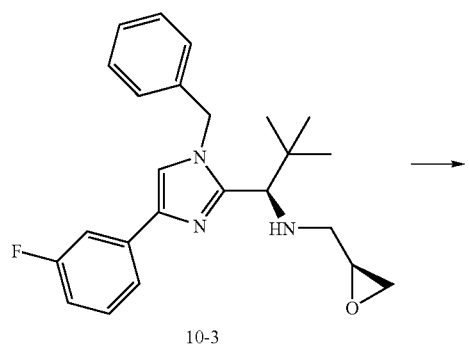

-continued

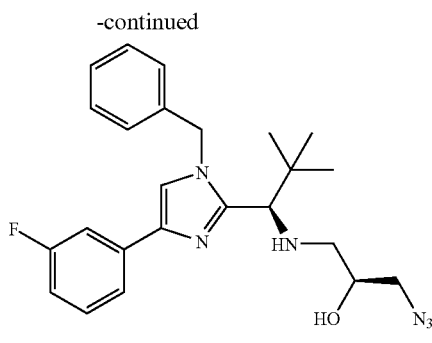

To a solution of amine 10-3 (1 eq.) in MeOH at room temperature was added NaN₃ (4 eq.). The reaction stirred for 3 days and was concentrated to give 10-4 that was used in the next step without further purification.

Step C

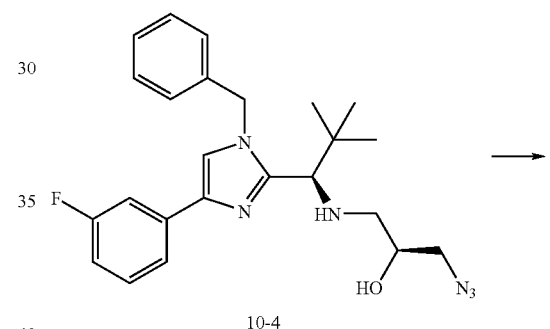

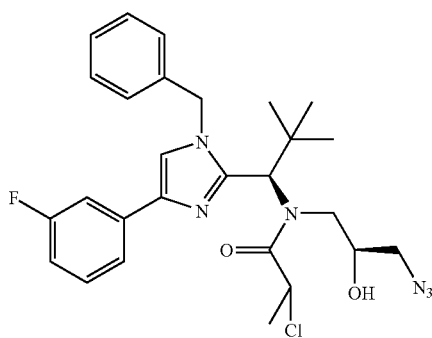

To a solution of crude amine 10-4 (1 eq.) in methylene chloride at 0° C. was added triethylamine (5 eq.) followed by 2-chloropropionyl chloride (2.5 eq.). Reaction was allowed to stir at room temperature until complete whereupon the solution was quenched with water followed by methylene chloride extractions. Combined organics were dried over sodium sulfate, filtered and concentrated. Crude product was purified on silica gel with 0-100% EtOAc/Hexane gradient elution to provide compound 10-5.

Step D

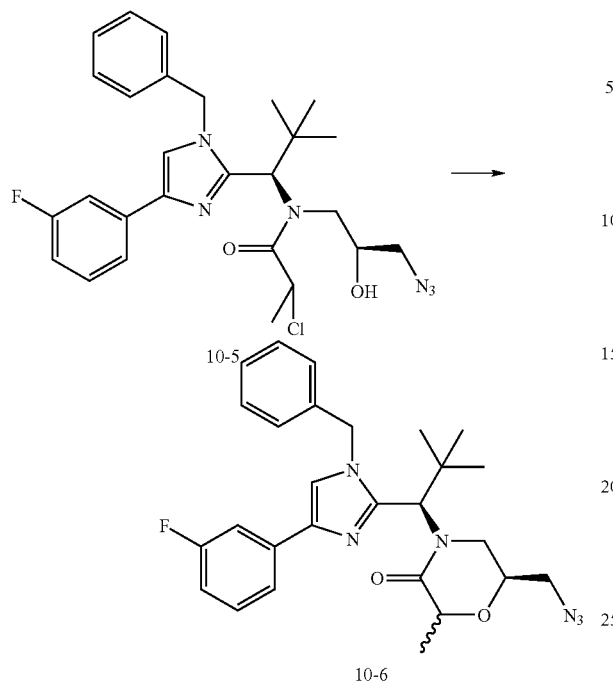

To a solution of alcohol 10-5 in DMF was added CsCO$_3$ (1 eq.) and TBAI (catalytic). Reaction was heated at 50° C. for 5 hours and upon completion was quenched by addition of sodium bicarbonate (saturated aq.) followed by EtOAc extraction (3×). Combined organics were dried over sodium sulfate, filtered and concentrated. Crude product was purified on silica gel with 0-100% EtOAc/Hexane gradient elution to provide compound 10-6.

Step E

To a solution of azide 10-6 in THF/H$_2$O was added triphenylphosphine at room temperature. Reaction was heated at 40° C. for 14 hours whereupon TFA (10 eq.) was added and reaction heated an additional hour at 40° C. then one hour at 80° C. Reaction was then cooled to room temperature and treated with a solution of LiOH in acetonitrile/water. This reaction was subjected to sonication for 10 minutes and then filtered through a pad of Celite. Filtrate was concentrated and purified by reverse phase HPLC to give the desired products 14 and 15; MH+ 465.3.

Example 11a (5R)-5-(aminomethyl)-1-[(1R)-1-(1-benzyl-4-phenyl-1H-imidazol-2-yl)-2,2-dimethylpropyl]piperazine-2,3-dione (16)

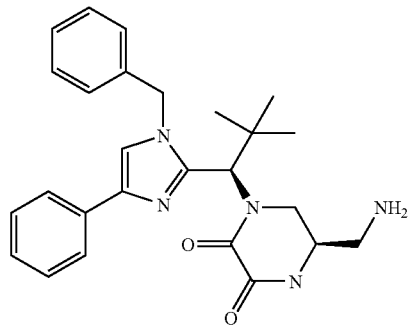

Step A

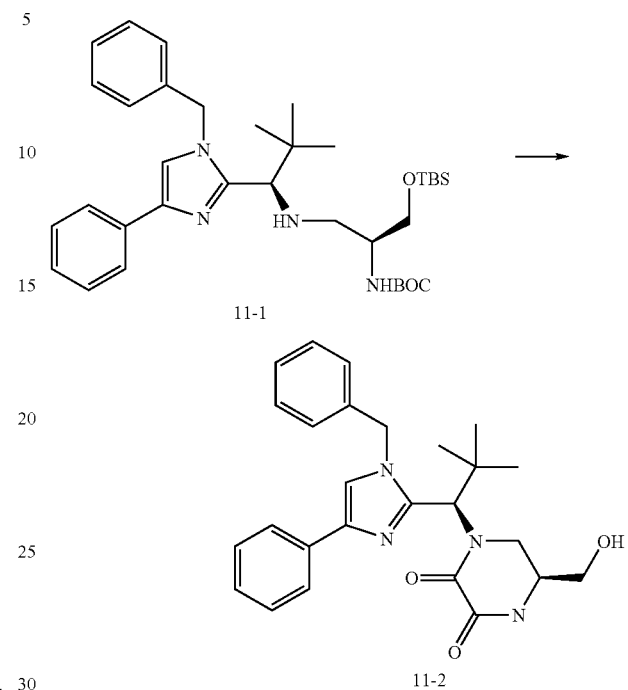

To a solution of amine 11-1 prepared as in Example 13, in methylene chloride at room temperature was added triethylamine (5 eq.) followed by oxalyl chloride (2.5 eq.) at room temperature. Reaction was stirred at room temperature until complete consumption of starting materials was observed. After this time, the reaction was washed with water and organic layer separated, dried and concentrated. The resulting crude material was then treated with 50% TFA in methylene chloride and heated at 40° C. until cyclization was complete. The reaction was then concentrated and crude oil was dissolved THF and treated with TBAF (2.5 eq.; 1M in THF). Reaction was heated at 40° C. and upon complete deprotection was concentrated and purified by reverse phase HPLC to give 11-2.

Steps B and C

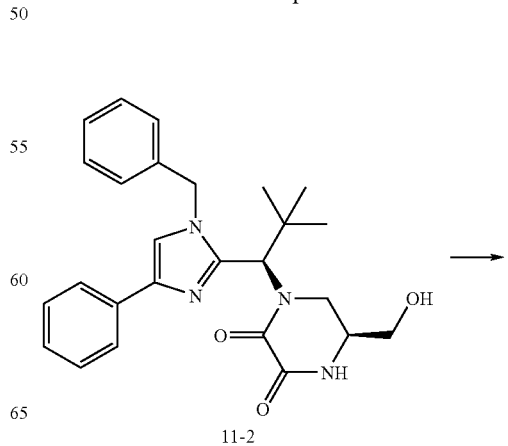

-continued

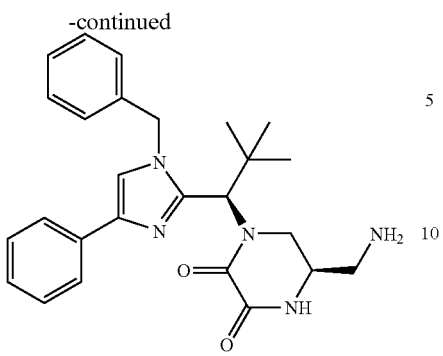

To a solution of alcohol 11-2 (1 eq.) in THF was added resin bound PPh₃ (2 eq.) followed by stirring at room temperature for 10 minutes. To this reaction were then added phthalamide (2 eq.) and DIAD (2 eq.). Reaction was heated at 40° C. for 30 minutes and upon cooling was diluted with EtOAc, filtered through a plug of Celite, concentrated and purified by reverse phase HPLC. Hydrazine (25 eq.) was then added to an EtOH solution of the phthalamide (1 eq.) at room temperature. Reaction was heated at 60° C. Upon completion, the cooled reaction was filtered and concentrated. The resulting oil was purified by reverse phase HPLC to provide 16; MH+ 446.2.

Example 11b (5S)-5-(aminomethyl)-1'-[(1R)-1'-(1-benzyl-4-phenyl-1H-imidazol-2-yl)-2,2-dimethylpropyl]piperazine-2,3-dione (17)

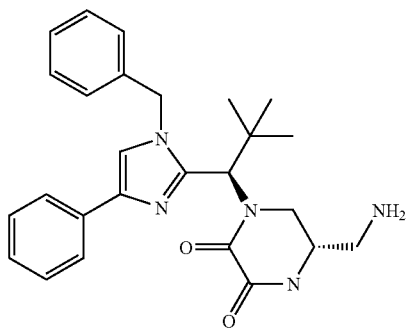

Prepare in a similar manner as Example 11a but starting from Boc-D-serine methyl ester; MH+ 446.2.

Example 12

(5R)-5-(aminomethyl)-1-[(1R)-1-(1-benzyl-4-phenyl-1H-imidazol-2-yl)-2,2-dimethylpropyl]-4-methylpiperazine-2,3-dione (18)

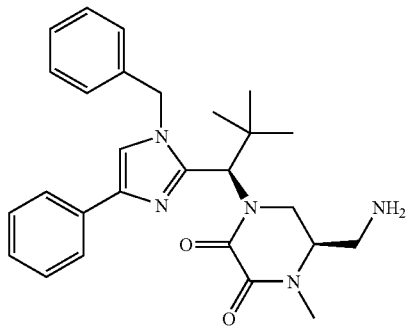

Step A

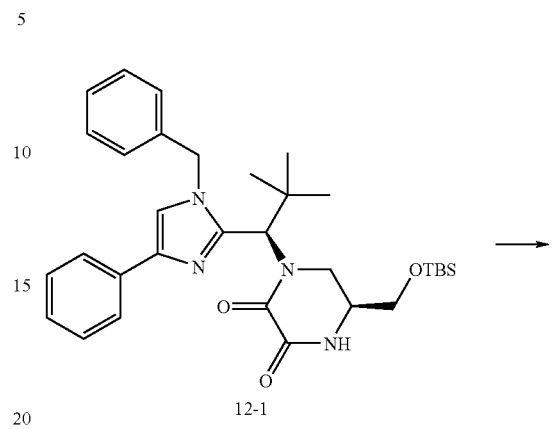

To a suspension of CsCO₃ (3 eq.) in dioxane was added amide 12-1, prepared as in Example 11, at room temperature and the reaction was stirred for 10 minutes. Methyl iodide was then added followed by stirring for one hour. Reaction was quenched with water and organics were separated, dried over Na₂SO₄ and concentrated. Crude product was purified on silica gel with 0-100% EtOAc/Hexane gradient elution to provide compound 12-2.

Step B

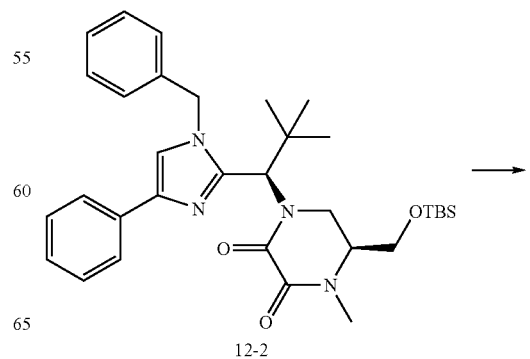

-continued

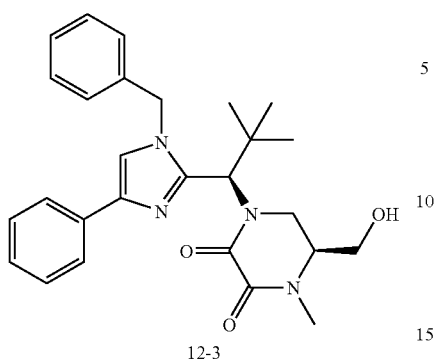

12-3

Alcohol 12-2 was dissolved THF and treated with TBAF (2.5 eq. of 1M in THF). Reaction was heated at 40° C. and upon complete deprotection was concentrated and purified by reverse phase HPLC to give 12-3.

Steps C and D

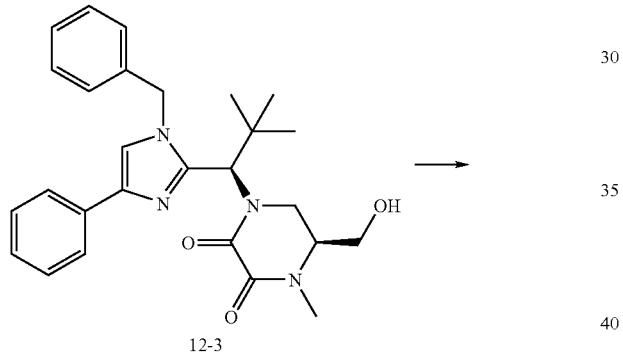

To a solution of alcohol 12-3 (1 eq.) in THF was added resin bound PPh₃ (2 eq.) followed by stirring at room temperature for 10 minutes. To this reaction was then added phthalamide (2 eq.) and DIAD (2 eq.). Reaction was heated at 40° C. for 30 minutes and upon cooling was diluted with EtOAc, filtered through a plug of Celite, concentrated and purified by reverse phase HPLC. To a solution of the phthalamide (1 eq.) in EtOH was added hydrazine (25 eq.) at room temperature. Reaction was heated at 60° C. Upon completion, the cooled reaction was filtered and concentrated. The resulting oil was purified by reverse phase HPLC to provide the desired compound 18; MH+ 460.3.

Example 13

(2S)-4-[(1R)-1-(1-benzyl-4-phenyl-1H-imidazol-2-yl)-2,2-dimethylpropyl]-2-(hydroxymethyl)-1,4-diazepan-5-one (19)

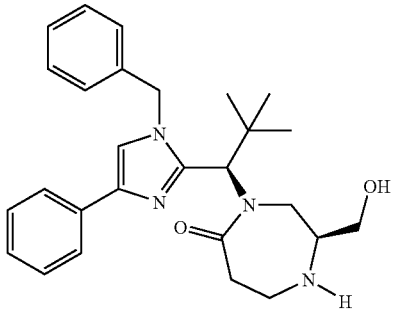

Step A

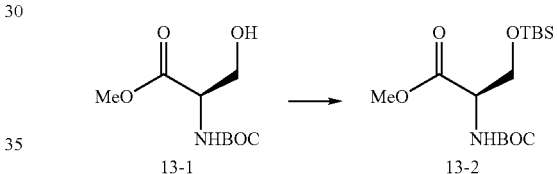

To a solution of alcohol 13-1 (1 eq.) in DMF was added triethylamine (3 eq.), DMAP (0.2 eq.) and TBDMSCl (2.2 eq.). Reaction was allowed to stir for 5 hrs. at room temperature and upon completion was quenched by addition of sodium bicarbonate (saturated aq.) followed by EtOAc extraction (3×). Combined organics were dried over sodium sulfate, filtered and concentrated. Crude product was purified on silica gel with 0-100% EtOAc/Hexane gradient elution to provide compound 13-2.

Step B

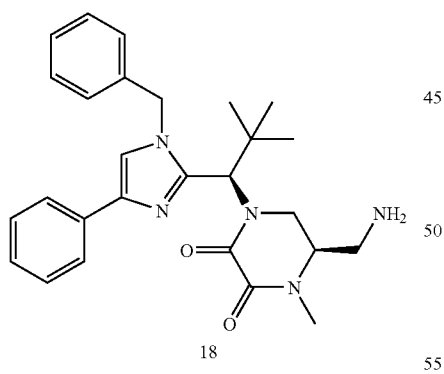

To a solution of BOC-L-serine methyl ester 13-2 in toluene was added DIBAL-H (3 eq. of 2.5 M in toluene) at 0° C. Reaction was allowed to warm to room temperature and stir until complete conversion was observed. After this time, reaction was treated with methanol and concentrated. To this residue was added 2M potassium sodium tartrate solution (sat. aqueous) and stirred vigorously for 30 minutes. The resulting residue was partitioned between EtOAc and water, layers were separated and aqueous was extracted with EtOAc three times. The combined organics were dried over sodium sulfate, filtered and concentrated. Crude product was purified on silica gel with 0-100% EtOAc/Hexane gradient elution to provide compound 13-3.

Step C

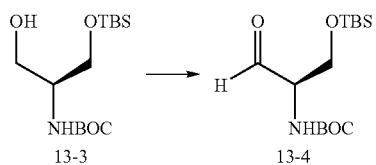

To a solution of oxalyl chloride (1.4 eq.) in anhydrous methylene chloride at −78° C. was added DMSO (2.2 eq.) followed by stirring for 10 minutes. A solution of alcohol 13-3 (1 eq.) in methylene chloride was then introduced drop wise and allowed to react for 5 minutes. Triethylamine (5 eq.) was then introduced slowly and upon complete addition, the reaction stirred for 10 min at −78° C. followed by 30 minutes at room temperature. Upon complete conversion, the reaction was diluted with EtOAc and washed with sodium bicarbonate (saturated aq.) three times. Organics were dried over sodium sulfate, filtered and concentrated. Crude product was purified on silica gel with 0-100% EtOAc/Hexane gradient elution to provide compound 13-4.

Step D

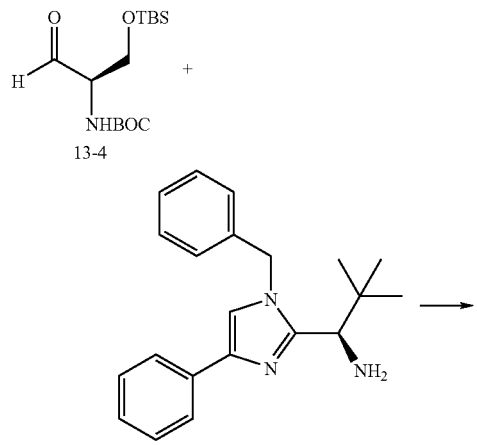

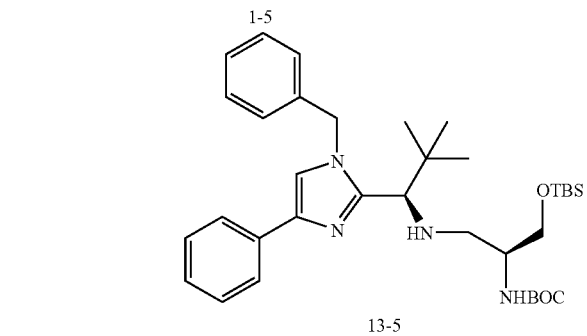

To a solution of aldehyde 13-4 and amine 1-5 (1.1 eq.) in methylene chloride at room temperature was added sodium triacetoxyborohydride (5 eq.) in portions. The reaction stirred for 12 hours and was quenched with water. The organic layer was separated, dried with magnesium sulfate, filtered and concentrated. The resulting residue was purified on silica gel with 0-100% EtOAc/Hexane gradient elution to provide compound 13-5.

Step E

To a solution of amine 13-5 in methylene chloride at room temperature was added triethylamine (5 eq.) followed by acryloyl chloride (3.3 eq.) at room temperature. Reaction was stirred at room temperature until complete consumption of starting materials was observed. After this time, the reaction was washed with water and organic layer separated, dried and concentrated. The resulting crude material was then treated with 50% TFA in methylene chloride and heated at 40° C. for a required period of time as to affect cyclization. After this time, the reaction was concentrated and crude oil was dissolved THF and treated with TBAF (2.5 eq. of 1M in THF). Reaction was heated at 40° C. and upon complete deprotection was concentrated and purified by reverse phase HPLC to give 19; MH+ 447.3.

Example 14

(2R)-2-(aminomethyl)-4-[(1R)-1-(1-benzyl-4-phenyl-1H-imidazol-2-yl)-2,2-dimethylpropyl]-1,4-diazepan-5-one (20)

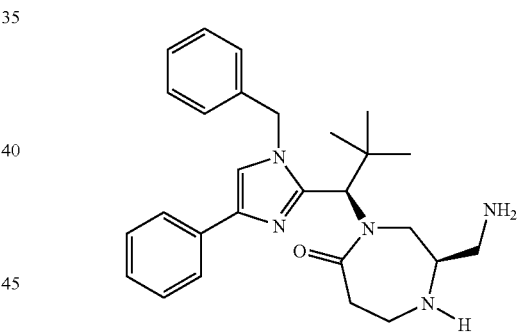

Step A

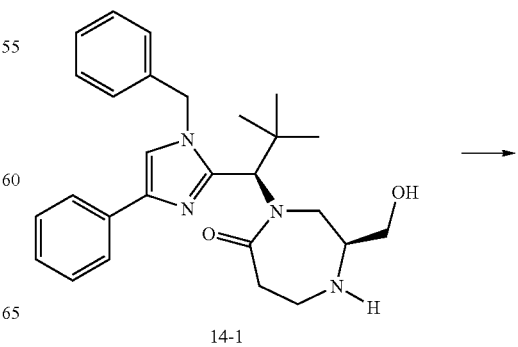

14-1

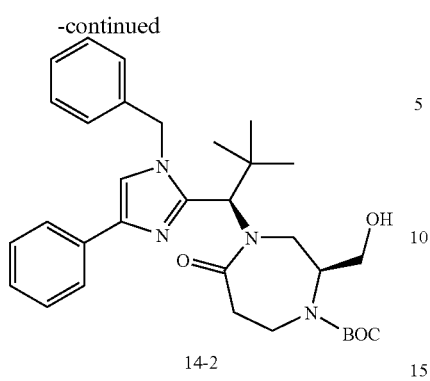

14-2

To a solution of amine 14-1, as prepared in Example 13, in MeOH was added BOC-anhydride (1.2 eq.) followed by triethylamine (3 eq.) at 0° C. The reaction was stirred at room temperature until complete consumption of starting materials was observed. Reaction was concentrated and resulting residue was purified on silica gel with 0-100% EtOAc/Hexane gradient elution to provide compound 14-2.

Step B

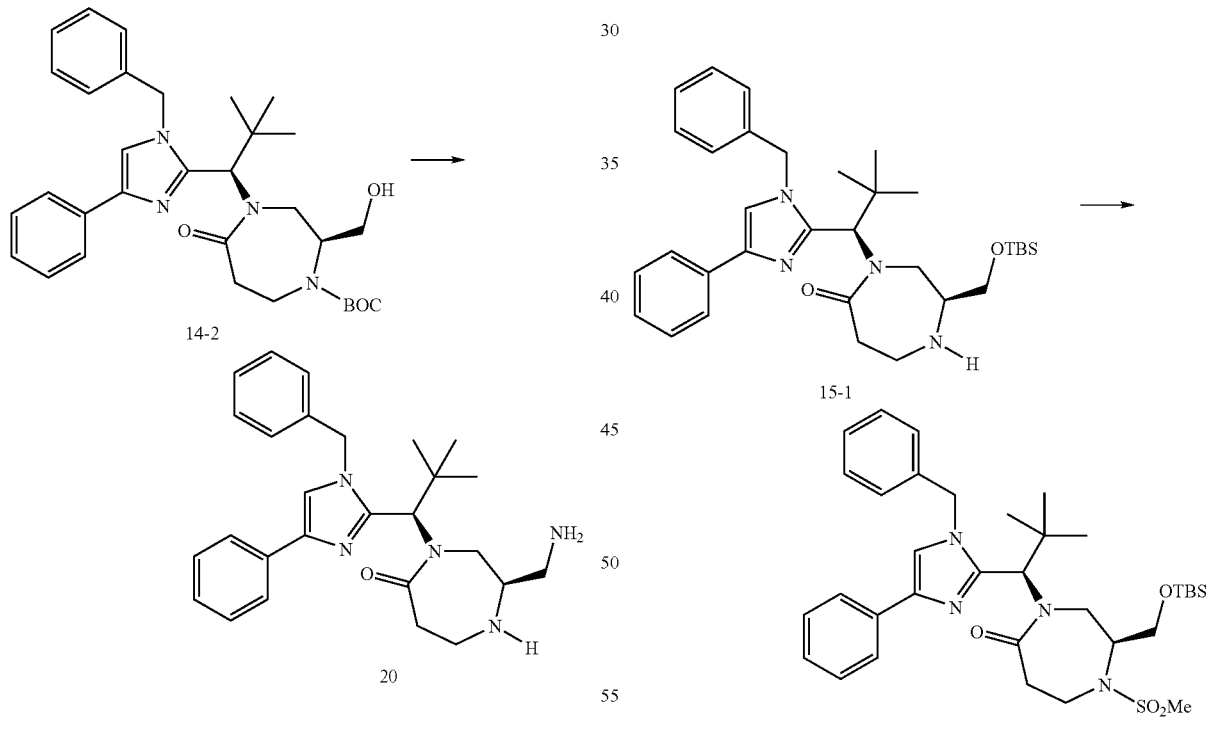

To a solution of alcohol 14-2 (1 eq.) in THF was added resin bound PPh$_3$ (2 eq.) followed by stirring at room temperature for 10 minutes. To this reaction were then added phthalamide (2 eq.) and DIAD (2 eq.). Reaction was heated at 40° C. for 30 minutes and upon cooling was diluted with EtOAc, filtered through a plug of Celite, concentrated and purified by reverse phase HPLC. To a solution of the phthalamide (1 eq.) in EtOH was added hydrazine (25 eq.) at room temperature. Reaction was heated at 60° C. Upon completion, the cooled reaction was filtered and concentrated. The resulting oil was dissolved in 20% TFA in methylene chloride and heated at 40° C. until complete deprotection was realized. The reaction was then concentrated and purified by reverse phase HPLC to provide 20; MH+ 446.3.

Example 15

(2R)-2-(aminomethyl)-4-[(1R)-1-(1-benzyl-4-phenyl-1H-imidazol-2-yl)-2,2-dimethylpropyl]-1-(methylsulfonyl)-1,4-diazepan-5-one (21)

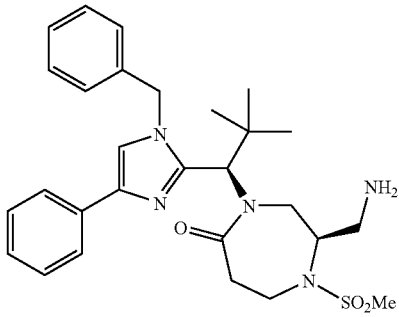

Step A

To a solution of amine 15-1 (1 eq.), as prepared in Example 13, in methylene chloride at 0° C. was added triethylamine (5 eq.) followed by methane sulfonyl chloride (2.5 eq.). Reaction was allowed to stir at room temperature until complete whereupon the solution was quenched with water followed by methylene chloride extractions. Combined organics were dried over sodium sulfate, filtered and concentrated. Crude product was purified on silica gel with 0-100% EtOAc/Hexane gradient elution to provide compound 15-2.

Step B

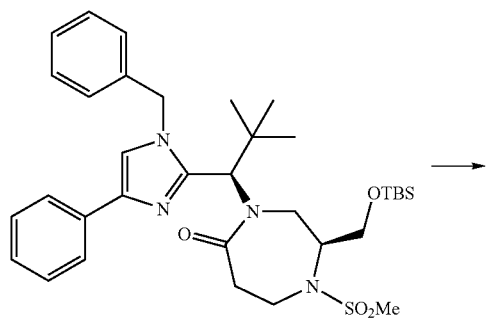

15-2

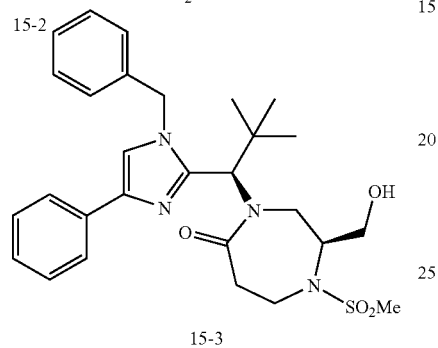

15-3

Sulfonamide 15-2 was dissolved THF and treated with TBAF (2.5 eq. of 1M in THF). Reaction was heated at 40° C. and upon complete deprotection was concentrated and purified by reverse phase HPLC to give 15-3.

Step C

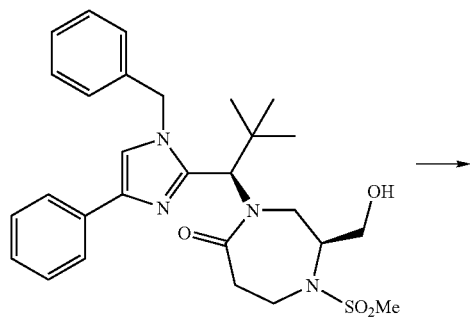

15-3

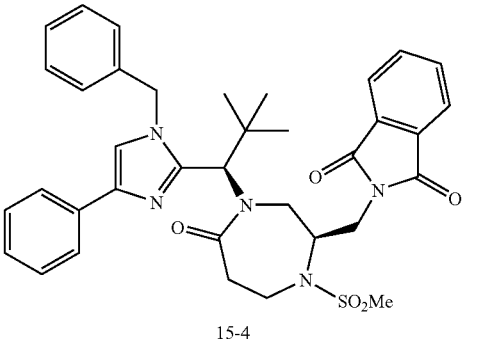

15-4

To a solution of alcohol 15-3 (1 eq.) in THF was added resin bound PPh₃ (2 eq.) followed by stirring at room temperature for 10 minutes. To this reaction were then added phthalamide (2 eq.) and DIAD (2 eq.). Reaction was heated at 40° C. for 30 minutes and upon cooling was diluted with EtOAc, filtered through a plug of Celite, concentrated and purified by reverse phase HPLC to give 15-4.

Step D

To a solution of phthalamide 15-4 (1 eq.) in EtOH was added hydrazine (25 eq.) at room temperature. Reaction was heated at 60° C. Upon completion, the cooled reaction was filtered and concentrated. The resulting oil was purified by reverse phase HPLC to provide 21; MH+ 524.3.

Example 16

(2S)-2-(aminomethyl)-4-[(1R)-1-(1-benzyl-4-phenyl-1H-imidazol-2-yl)-2,2-dimethylpropyl]-1,4-oxazepan-5-one (22) and (2R)-2-(aminomethyl)-4-[(1R)-1-(1-benzyl-4-phenyl-1H-imidazol-2-yl)-2,2-dimethylpropyl]-1,4-oxazepan-5-one (23)

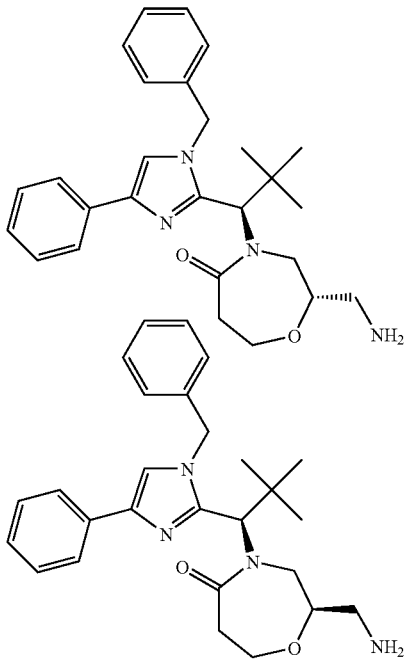

Step A

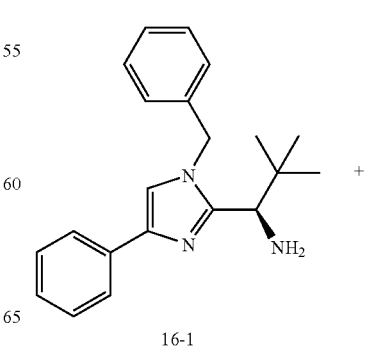

16-1

-continued

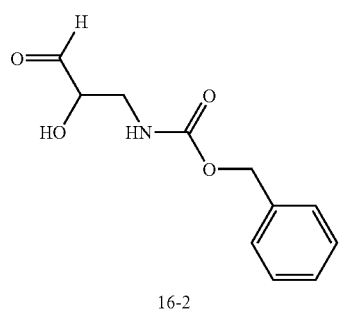

16-2

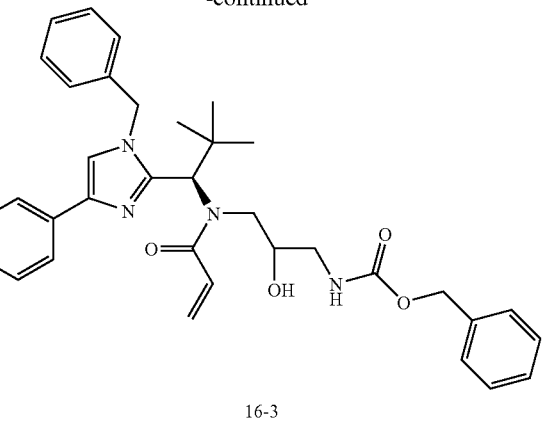

16-3

To a solution of amine 16-2 (1 eq.) in methylene chloride at 0° C. was added triethylamine (5 eq.) followed by acroloyl chloride (2.5 eq.). Reaction was allowed to stir at room temperature until complete whereupon the solution was quenched with water followed by methylene chloride extractions. Combined organics were dried over sodium sulfate, filtered and concentrated. Crude product was purified on silica gel with 0-100% EtOAc/Hexane gradient elution to provide compound 16-3.

Step C

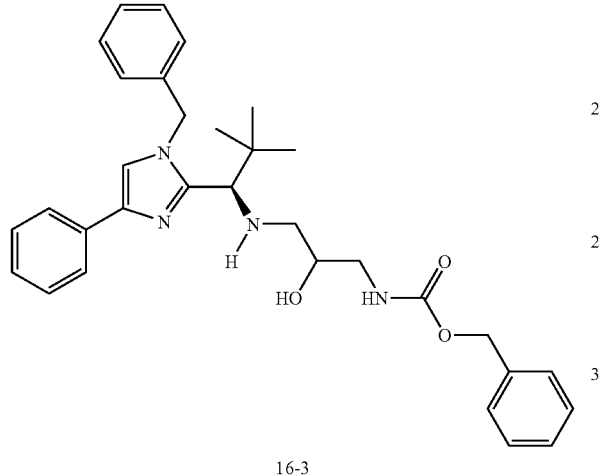

16-3

To a solution of 16-1 amine and aldehyde 16-2 (1.1 eq.) in methylene chloride at room temperature was added sodium triacetoxyborohydride (5 eq.) in portions. The reaction stirred for 12 hours and was quenched with water. The organic layer was separated, dried with magnesium sulfate, filtered and concentrated. The resulting residue was purified on silica gel with 0-100% EtOAc/Hexane gradient elution to provide compound 16-3.

Step B

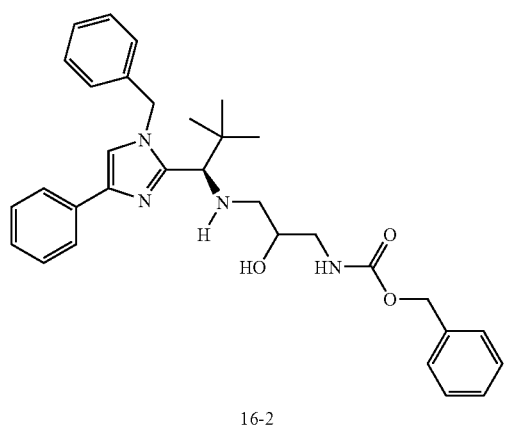

16-2

16-4

To a solution of amide 16-3 in THF was added mercury(II) trifluoroacetate (1 eq.) at room temperature and reaction stirred for 1 hour. After this time, the reaction was cooled to 0° C. and treated with 2N NaOH (2 eq.) followed by NaBH$_4$ (0.6 eq. of 0.5 N in 2N NaOH). The reaction was allowed to stir until complete conversion was observed and then diluted with EtOAc and washed with water. Organics were dried over sodium sulfate, filtered and concentrated. The crude material was purified by reverse phase HPLC to provide 16-4.

Step D

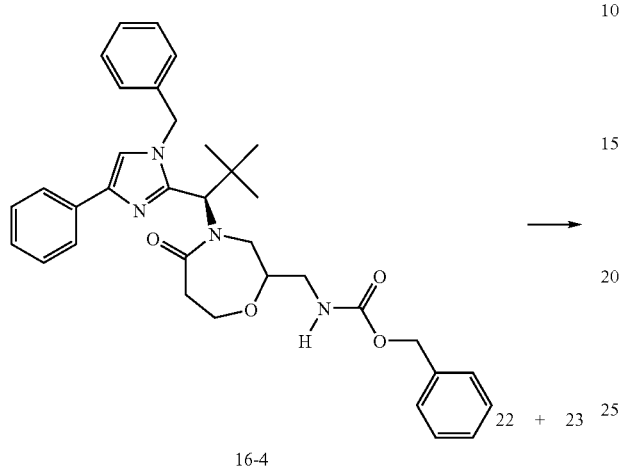

16-4

To a solution of amide 16-4 in EtOH was added Pd/C (0.5 eq.) at room temperature. Hydrogen gas was bubbled through the mixture for 10 minutes and the reaction was stirred for 3 hours under an atmosphere of H$_2$. After this time, the reaction was filtered through a pad of Celite, concentrated and purified by reverse phase HPLC to give 22 and 23; MH+ 447.3.

Example 17

(2,2-dimethyl-[1,3]dioxan-5-yl)-methanol

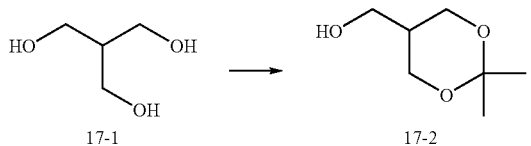

17-1          17-2

Triol 17-1 (1 eq.) was dissolved in DMF at a concentration of approximately 0.5 M and 2,2-dimethoxypropane (1.16 eq.) and p-toluenesulfonic acid monohydrate (0.03 eq.) were added. The solution was stirred for one or more days, and was quenched with TEA (0.5 eq.). As much solvent as possible was removed in vacuo and 17-2 was purified by distillation under vacuum.

Example 18

2,2-dimethyl-1,3-dioxane-5-carbaldehyde

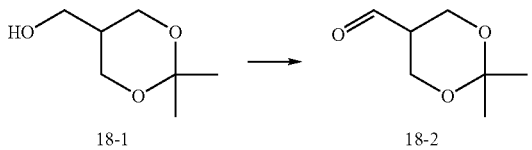

18-1          18-2

Under N$_2$ atmosphere, oxalyl chloride (1.4 eq.) was dissolved in DCM then cooled to −78° C. Dropwise, DMSO (2.2 eq.) was added. This solution was stirred for about 10 minutes, then 18-1 (1 eq.) was dissolved in more DCM for a total concentration of 0.2 M. After reacting for 5 minutes, TEA (5 eq.) was added. This mixture stirred for 10 minutes at −78° C., then for another 10 minutes at room temperature. This reaction was best monitored by TLC using a 1:1 ratio of hexane to ethyl acetate as the developing solvent and visualizing the results with CAM stain. The reaction mixture containing 18-2 was used without further workup.

Example 19

(6S)-6-(aminomethyl)-4-[(1R)-1-(1-benzyl-4-phenyl-1H-imidazol-2-yl)-2,2-dimethylpropyl]-1,4-oxazepan-3-one (24) and (6R)-6-(aminomethyl)-4-[(1R)-1-(1-benzyl-4-phenyl-1H-imidazol-2-yl)-2,2-dimethylpropyl]-1,4-oxazepan-3-one (25)

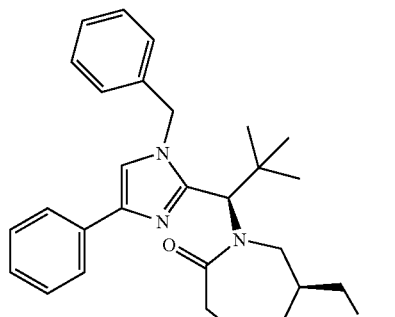

(R)-6-(aminomethyl)-4-((R)-1-(1-benzyl-3-phenyl-1H-1,2,4-triazol-5-yl)-2,2-dimethylpropyl)-1,4-oxazepan-3-one Step A: Reductive Amination

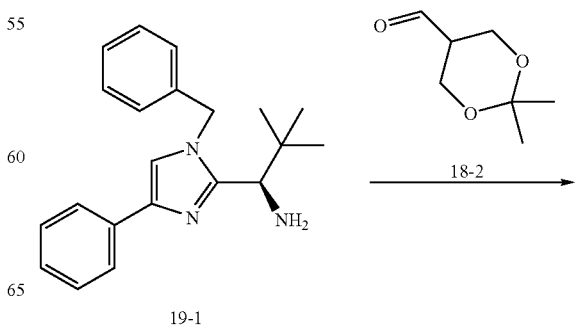

19-1

87

-continued

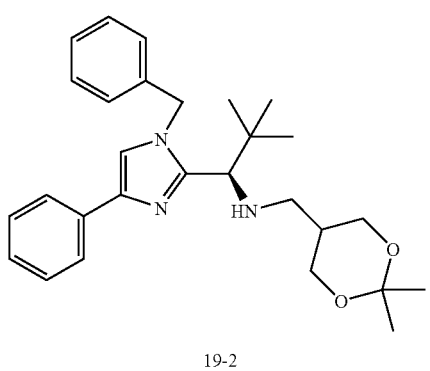

19-2

Amine 19-1 (1 eq.) was dissolved in DCM and added to aldehyde 18-2 for a total concentration between 0.1-0.15 M. After 5 minutes the reaction was cooled to 0° C. and Na(OAc)₃BH (1.5 eq.) and glacial acetic acid (1 eq.) was added. The reaction was monitored by LCMS for completion. The reaction was diluted with ethyl acetate then washed three times with a saturated sodium bicarbonate solution in water. Finally, the product was dried with anhydrous sodium sulfate, filtered, and the solvent was removed in vacuo.

Step B: Acetylation

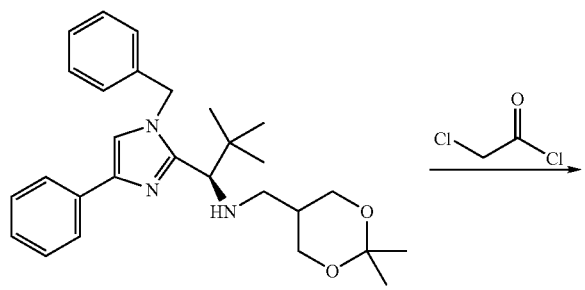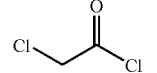

19-2

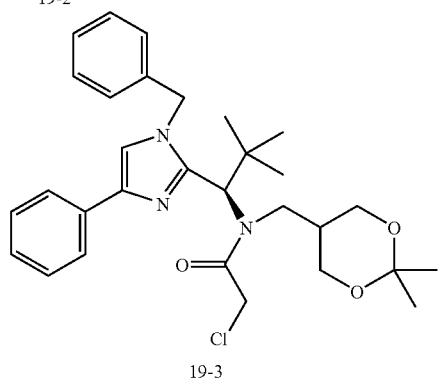

19-3

Amine 19-2 was dissolved in DCM to make a 0.2 M solution and cooled to 0° C. Slowly, TEA (5 eq.) was added and stirred for 5 minutes. Chloroacetyl chloride (3 eq.) was added dropwise. The reaction was diluted with ethyl acetate, washed three times with a saturated sodium bicarbonate solution in water, dried with anhydrous sodium sulfate, filtered, and con-

88 centrated in vacuo. The product 19-3 was purified by chromatography using a gradient of about 0-70% ethyl acetate in hexane.

Step C: Diol Deprotection

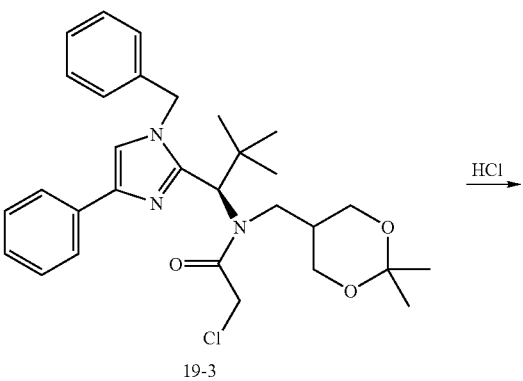

19-3

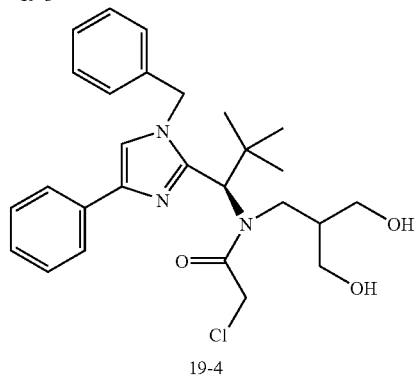

19-4

Chloride 19-3 was dissolved in acetonitrile and cooled to 0° C. 3N HCl was added dropwise and the reaction monitored by LCMS, with further addition of HCl until deprotection was complete. The solution was concentrated in vacuo, diluted with ethyl acetate, and washed three times with a saturated sodium bicarbonate solution in water. Finally, the product 19-4 was dried with anhydrous sodium sulfate, filtered, and the solvent was removed in vacuo.

Step D: Cyclization

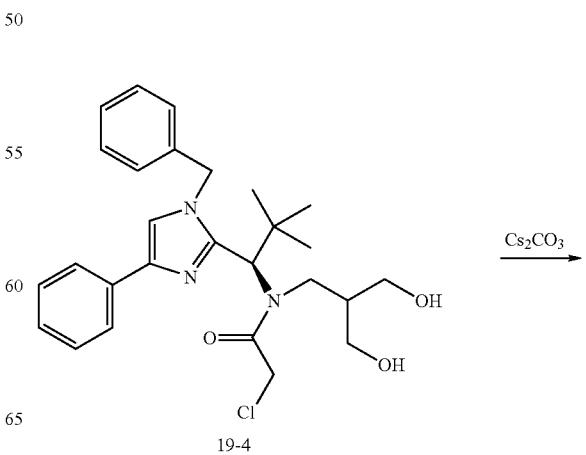

19-4

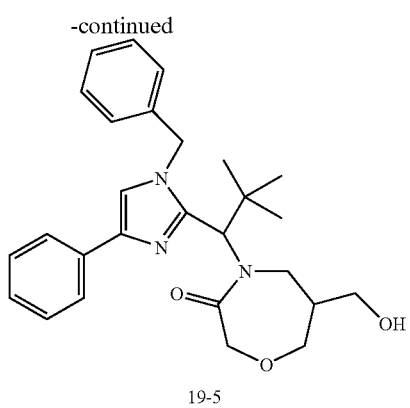

19-5

The deprotected alcohol 19-4 was dissolved in DMF to make a 0.1M solution. One equivalent of $Cs_2CO_3$ and a catalytic amount of TBAI (tetrabutyl ammonium iodide) was added. The reaction was heated to approximately 40-55° C. for 4-6 hours. On completion the reaction was concentrated in vacuo, diluted with EtOAc, and washed with saturated bicarbonate. The EtOAc layer was concentrated in vacuo and purified by chromatography using a gradient of about 0-75% ethyl acetate in hexane to give 19-5.

Step E. Aldehyde Formation to Racemise Alcohol

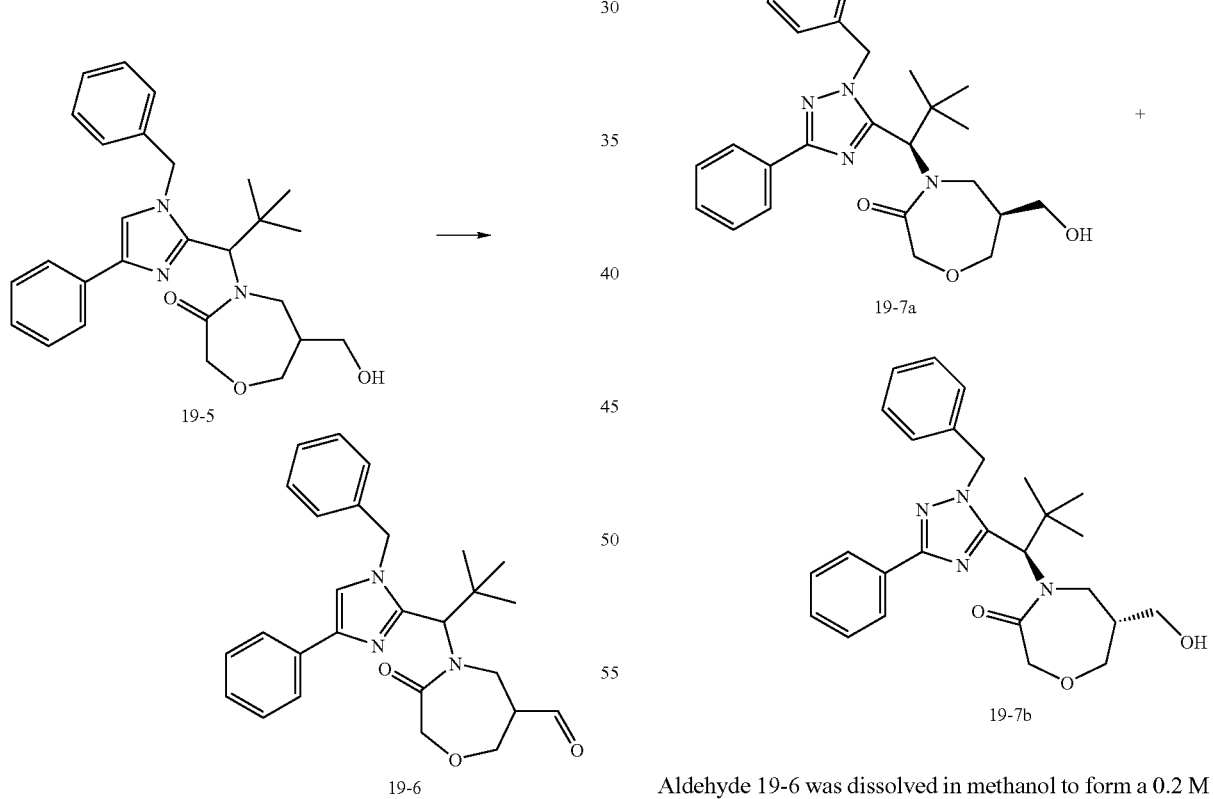

19-5

19-6

Under $N_2$ gas, oxalyl chloride (1.4 eq.) was dissolved in DCM and then cooled to −78° C. Dropwise, DMSO (2.2 eq.) was added. This solution was stirred for about 10 minutes, then alcohol 19-5 (1 eq.) was dissolved in more DCM for a total concentration of 0.2M. After reacting for 5 minutes, TEA (5 eq.) was added. This mixture was stirred for 10 minutes at −78° C., then another 10 minutes at room temperature. The reaction was diluted with ethyl acetate then washed three times with a saturated sodium bicarbonate solution in water. Finally, the product 19-6 was dried with anhydrous sodium sulfate, filtered, and the solvent was removed in vacuo.

Step F: Conversion to the (R) and (S) Alcohols

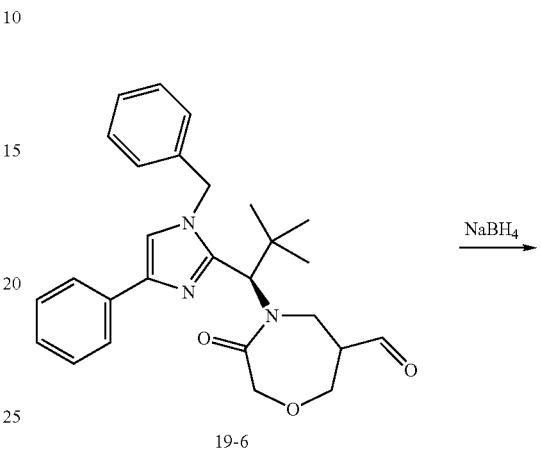

19-6

19-7a 19-7b

Aldehyde 19-6 was dissolved in methanol to form a 0.2 M solution and cooled to 0° C. Sodium borohydride (1.5 eq.) was added, and the reaction was maintained for 5 to 10 minutes. The solution was concentrated in vacuo, diluted with EtOAc, and washed with saturated bicarbonate. The EtOAc layer was concentrated in vacuo and purified by chromatography. At this step the two diastereomers of the alcohol were separated by reverse phase HPLC.

Step G: Conversion to Amine

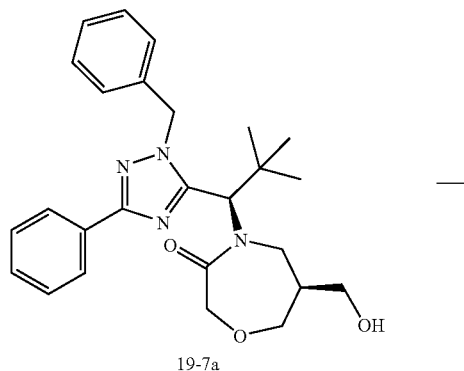

19-7a

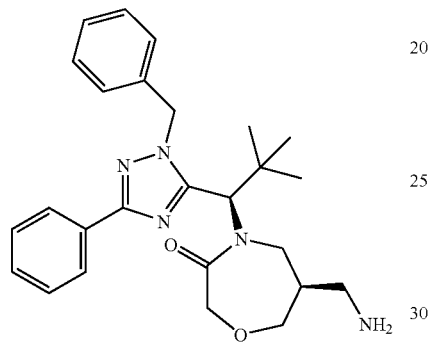

To each resolved alcohol diastereomer dissolved in dry THF was added 5 eq. of resin bound PPh₃, 5 eq. of phthalimide, and 5 eq. DIAD. The reaction was warmed to about 55° C. for 30 min. On complete conversion to the phthalimido derivative, the reaction was diluted with EOAc, filtered through celite, and washed with saturated NaHCO₃. The EtOAc layer was dried over anhydrous Na₂SO₄ and concentrated in vacuo, and purified by HPLC. The purified phthalimido derivatives were subjected to a final deprotection step with 2M MeNH₂ in methanol (used as solvent) at 60° C. for about 1 h. The crude product was purified by reverse phase HPLC; MH+ 447.3.

Example 20

(6R)-6-(aminomethyl)-4-{(1R)-1-[1-(3,5-difluorobenzyl)-4-(3-fluorophenyl)-1H-imidazol-2-yl]-2,2-dimethylpropyl}-1,4-oxazepan-3-one (26)

Compound 26 was prepared in a similar manner as Example 19; MH+ 501.2.

Example 21

(6R)-6-(aminomethyl)-4-{(1R)-1-[1-benzyl-4-(3-fluorophenyl)-1H-imidazol-2-yl]-2,2-dimethylpropyl}-1,4-oxazepan-3-one (27)

Compound 27 was prepared in a similar manner as Example 19; MH+ 465.3.

Example 22

(6R)-6-(aminomethyl)-4-{(1R)-1-[1-(3-fluorobenzyl)-4-(3-fluorophenyl)-1H-imidazol-2-yl]-2,2-dimethylpropyl}-1,4-oxazepan-3-one (28) and (6S)-6-(aminomethyl)-4-{(1R)-1-[1-(3-fluorobenzyl)-4-(3-fluorophenyl)-1H-imidazol-2-yl]-2,2-dimethylpropyl}-1,4-oxazepan-3-one (29)

Compounds 28 and 29 was prepared in a similar manner as Example 19; MH+ 483.2.

Example 23

(6S)-6-(aminomethyl)-1-[(1R)-1-(1-benzyl-4-phenyl-1H-imidazol-2-yl)-2,2-dimethylpropyl]-1,4-diazepane-2,3-dione (30)

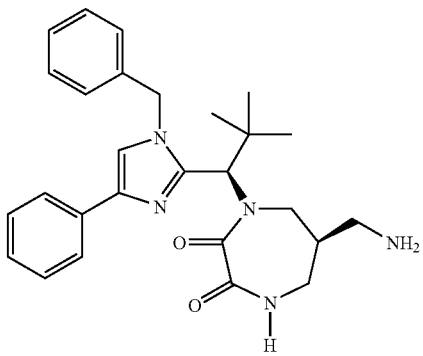

Step A

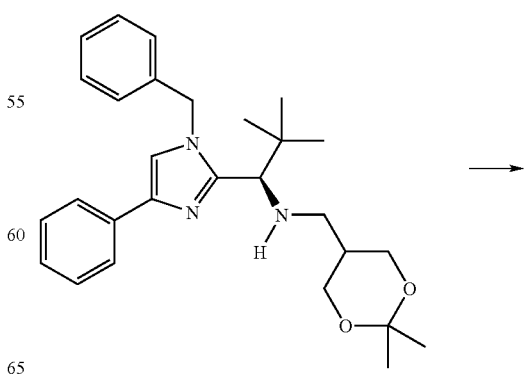

19-2

-continued

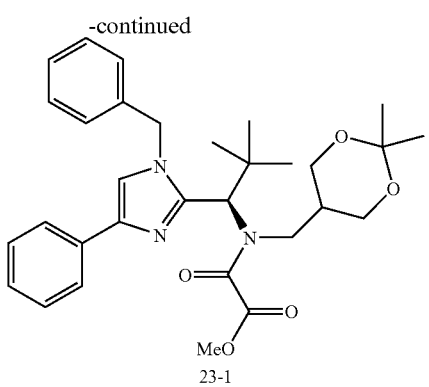
23-1

To a solution of amine 19-2 (1 eq.) in methylene chloride at 0° C. was added triethylamine (5 eq.) followed by methyl-2-chloro-2-oxoacetate (2.5 eq.). Reaction was allowed to stir at room temperature until complete whereupon the solution was quenched with water followed by methylene chloride extractions. Combined organics were dried over sodium sulfate, filtered and concentrated. Crude product was purified on silica gel with 0-100% EtOAc/Hexane gradient elution to provide compound 23-1.

Step B

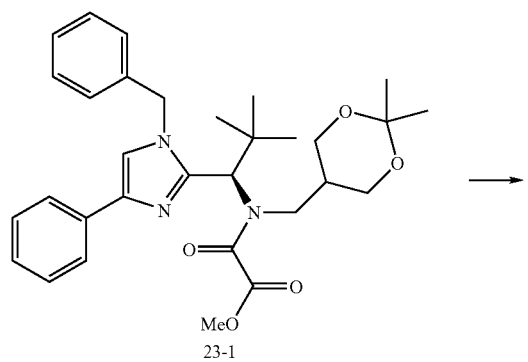
23-1

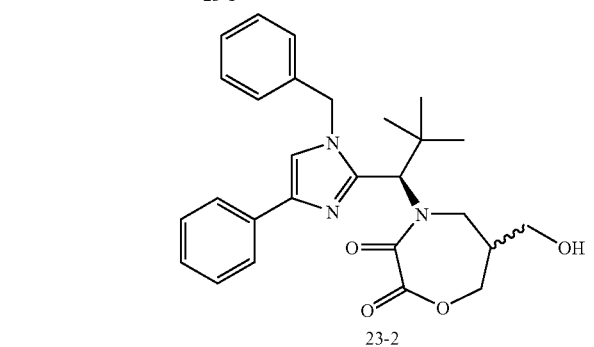
23-2

To a solution of amide 23-1 in acetonitrile (1 eq.) at 0° C. was added HCl (3N aq) (15 eq.) drop wise. Reaction was stirred at room temperature and upon complete conversion; the reaction was diluted with EtOAc and washed with sodium bicarbonate (saturated aq.) three times. Organics were dried over sodium sulfate, filtered and concentrated. Crude product was purified on silica gel with 0-100% EtOAc/Hexane gradient elution to provide the resulting diol that was next puri- fied, suspended in DMF, and treated with $CsCO_3$ (1 eq.) and TBAI (catalytic). Reaction was heated at 50° C. for 5 hours and upon completion was quenched by addition of sodium bicarbonate (saturated aq.) followed by EtOAc extraction (3×). Combined organics were dried over sodium sulfate, filtered and concentrated. Crude product was purified on silica gel with 0-100% EtOAc/Hexane gradient elution to provide compound 23-2.

Step C

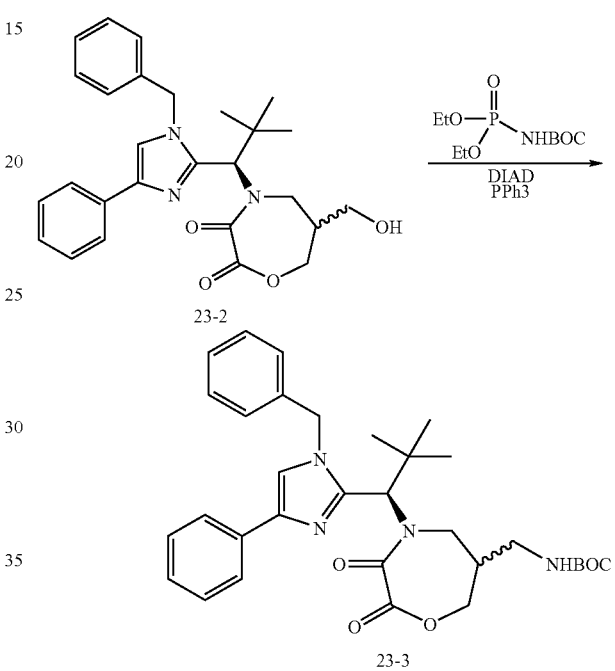

To a solution of alcohol 23-2 (1 eq.) in THF was added resin bound $PPh_3$ (2 eq.) followed by stirring at room temperature for 10 minutes. To this reaction was then added N—BOC phosphonate (2 eq.) and DIAD (2 eq.). Reaction was heated at 40° C. for 30 minutes and upon cooling was diluted with EtOAc, filtered through a plug of Celite, concentrated and purified by reverse phase HPLC to give 23-3.

Step D

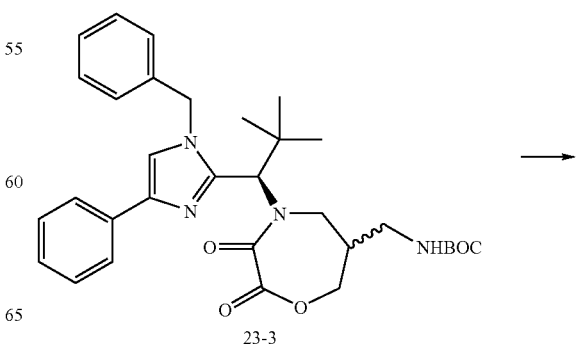
23-3

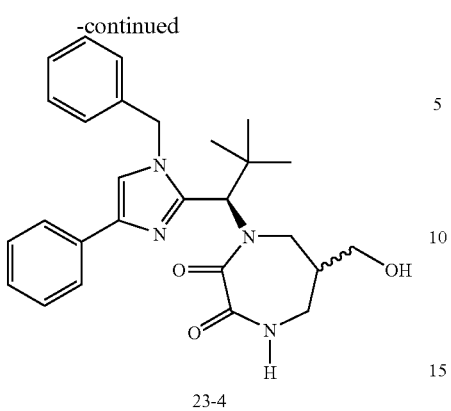

23-4

A solution of amide 23-3 in 20% HCl in benzene was stirred at room temperature. After complete conversion, the reaction was diluted with EtOAc and washed with water. Organics were dried over sodium sulfate, filtered and concentrated. Crude product was purified on silica gel with 0-100% EtOAc/Hexane gradient elution to provide compound 23-4.

Step E

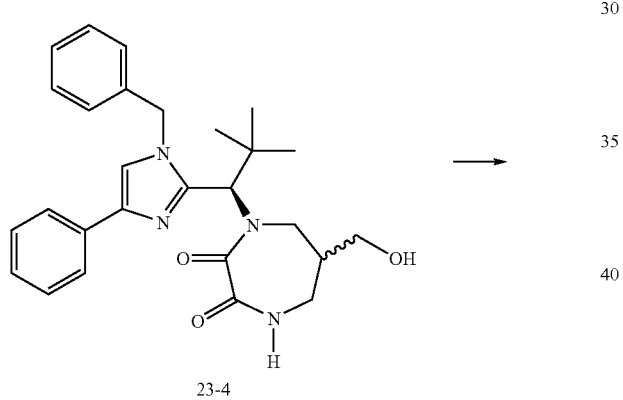

23-4

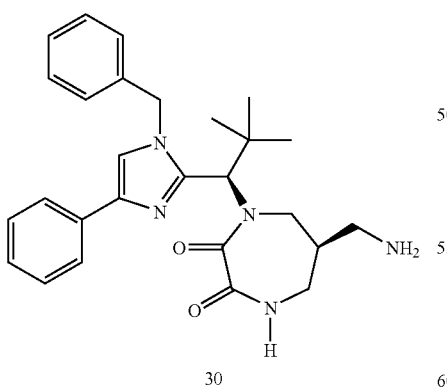

30

To a solution of alcohol 23-4 (1 eq.) in THF was added resin bound PPh$_3$ (2 eq.) followed by stirring at room temperature for 10 minutes. To this reaction were then added phthalamide (2 eq.) and DIAD (2 eq.). Reaction was heated at 40° C. for 30 minutes and upon cooling was diluted with EtOAc, filtered through a plug of Celite, concentrated and purified by reverse phase HPLC. To a solution of the resulting phthalamide (1 eq.) in EtOH was added hydrazine (25 eq.) at room temperature. Reaction was heated at 60° C. Upon completion, the cooled reaction was filtered and concentrated. The resulting oil was purified by reverse phase HPLC to provide 30; MH+ 460.3.

Example 24

(6R)-1-[(1R)-1-(1-benzyl-4-phenyl-1H-imidazol-2-yl)-2,2-dimethylpropyl]-6-fluoro-1,4-diazepan-2-one (31) and (32)

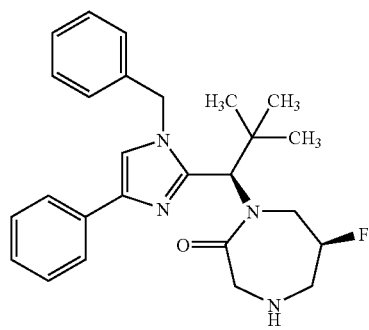

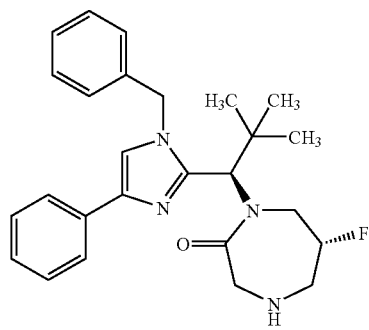

Step A

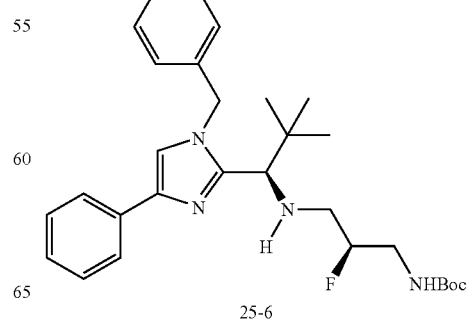

25-6

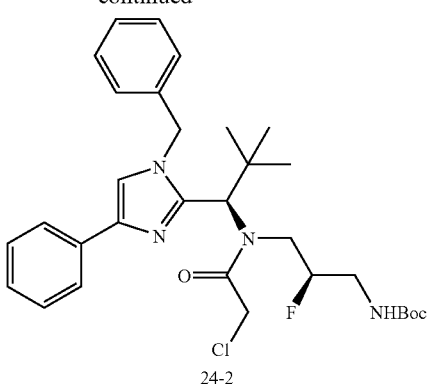

To a solution of amine 25-6, prepared as in Example 25, in methylene chloride at 0° C. was added triethylamine (5 eq.) followed by chloroacetyl chloride (2.5 eq.). Reaction was allowed to stir at room temperature until complete whereupon the solution was quenched with water followed by methylene chloride extractions. Combined organics were dried over sodium sulfate, filtered and concentrated. Crude product was purified on silica gel with 0-100% EtOAc/Hexane gradient elution to provide chloride 24-2.

Step B

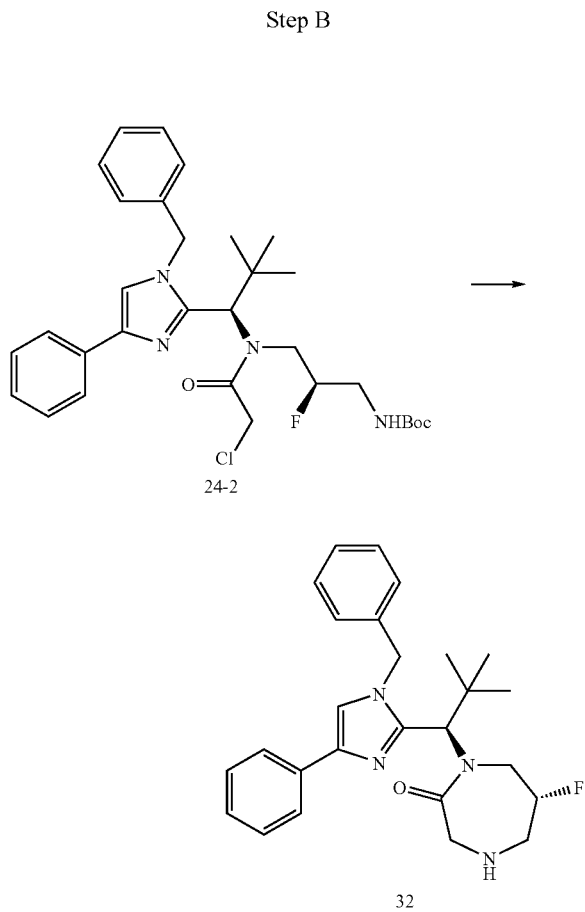

To a solution of chloride 24-2 (1 eq.) in DMSO was added tetrazole (10 eq.) and NaOH (10 eq.). Reaction was allowed to stir at room for 16 h whereupon the solution was quenched with water followed by EtOAc extractions. Combined organics were dried over sodium sulfate, filtered and concentrated. The crude material was then treated with 50% TFA in methylene chloride, and upon completion was concentrated and purified by reverse phase HPLC to provide the desired compound 32; MH+ 435.2.

The other diastereomer 31 was prepared in an analogous manner starting from the other fluoro-sidechain diastereomer of 24-1; MH+ 435.2.

Example 25

Synthesis of tert-butyl (S)-3-((R)-1-(1-benzyl-4-phenyl-1H-imidazol-2-yl)-2,2-dimethylpropylamino)-2-fluoropropylcarbamate Step E: Reductive Amination

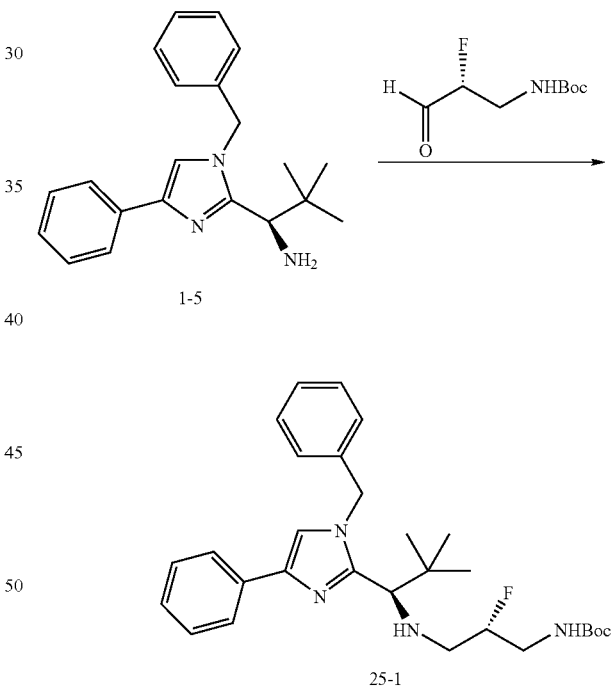

The phenyl imidazole 1-5 from step D of Example 1 (1 eq., 2.0 g) was combined with the aldehyde (1.3 eq., 1.56 g) and sodium triacetoxyborohydride (2 eq., 2.65 g) in 30 mL of methylene chloride. This was followed by acetic acid (2 eq., 0.72 mL) and the reaction was stirred at RT under nitrogen overnight. The reaction was worked up with water, saturated sodium bicarbonate then saturated sodium chloride. The organic layer was dried over magnesium sulfate, filtered and concentrated. The material was purified on a column and gave the resulting product 25-1 as 2.15 g of a white solid.

Example 26

Synthesis of (R)-5-(aminomethyl)-3-((R)-1-(1-benzyl-4-(2,5-difluorophenyl)-1H-imidazol-2-yl)-2,2-dimethylpropyl)oxazolidin-2-one and (S)-5-(aminomethyl)-3-((R)-1-(1-benzyl-4-(2,5-difluorophenyl)-1H-imidazol-2-yl)-2,2-dimethylpropyl)oxazolidin-2-one

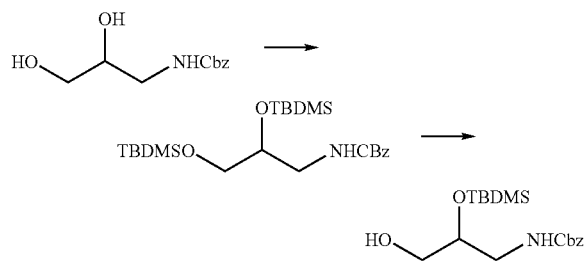

To a solution of benzyl 2,3-dihydroxypropylcarbamate in DMF (0.1 M) was added TBDMSCl (2.2 eq.) and imidazole (2.5 eq.) at room temperature. After stirred for 20 h, the reaction mixture was worked up with EtOAc, which was washed with water and brine. The organic layer was separated, dried and concentrated to give the crude bis-silylated product, which was dissolved in methanol (0.16 M) followed by addition of p-toluenesulfonic acid (0.1 equiv.) at 0° C. The reaction mixture was stirred for 1.5 h at the same temperature. After quenched with saturated NaHCO₃ aqueous solution, the reaction mixture was extracted with EtOAc, which was washed with water and brine. The organic layer was separated, dried, concentrated, and purified on silica gel with 0-100% EtOAc/Hexanes gradient elution to provide the pure benzyl 2-(tert-butyldimethylsilyloxy)-3-hydroxypropylcarbamate.

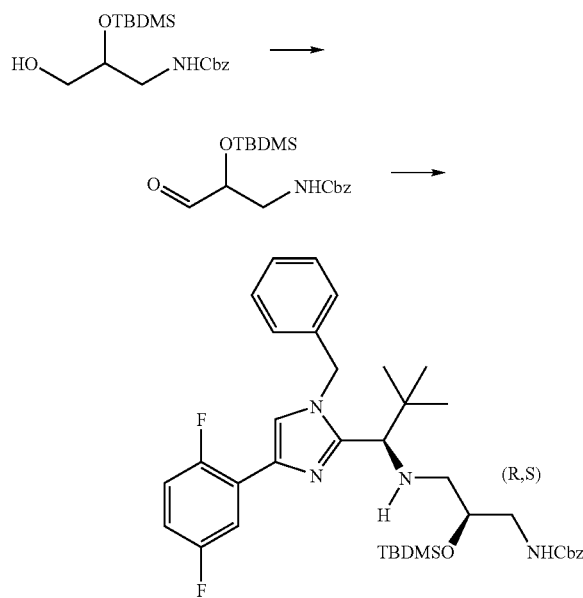

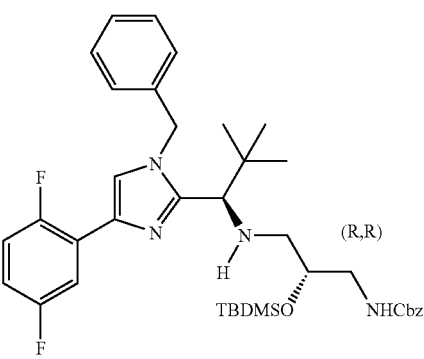

To a solution of benzyl 2-(tert-butyldimethylsilyloxy)-3-hydroxypropylcarbamate (1.0 eq.) in dichloromethane (0.1 M) was added pyridine (5.0 eq.) and Dess-Martin Periodinane® (1.5 eq.) at 0° C. The reaction mixture was stirred for 3 h and quenched with 5% NaHCO₃ aqueous solution and 1.0 M aqueous Na₂S₂O₃ solution. After stirred for 1 h, the organic layer was separated, washed with water and brine, dried, and concentrated. The crude aldehyde was added to a solution of (R)-1-(1-benzyl-4-(2,5-difluorophenyl)-1H-imidazol-2-yl)-2,2-dimethylpropan-1-amine (1.2 eq.), prepared according to the general procedure reported previously, in dichloromethane (0.2 M) with a drop of acetic acid at room temperature. After stirred for 0.5 h, sodium triacetoxyborohydride (1.5 eq.) was added to the reaction mixture at 0° C. followed by warming up to room temperature for 1 h. After quenched with saturated NaHCO₃ aqueous solution, the reaction mixture was worked up with EtOAc which was washed with water and brine. The organic layer was separated, dried, and concentrated. The crude diastereomeric mixture was separated on silica gel with 20% EtOAc/Hexanes elution to provide the pure diastereomers, benzyl (S)-3-((R)-1-(1-benzyl-4-(2,5-difluorophenyl)-1H-imidazol-2-yl)-2,2-dimethylpropylamino)-2-(tert-butyldimethylsilyloxy)propylcarbamate and benzyl (R)-3-((R)-1-(1-benzyl-4-(2,5-difluorophenyl)-1H-imidazol-2-yl)-2,2-dimethylpropylamino)-2-(tert-butyldimethylsilyloxy)propylcarbamate, where the stereochemistry at the carbon attached to oxygen atom was arbitrarily assigned ((R,R) diastereomer was more polar than (R,S) isomer on TLC).

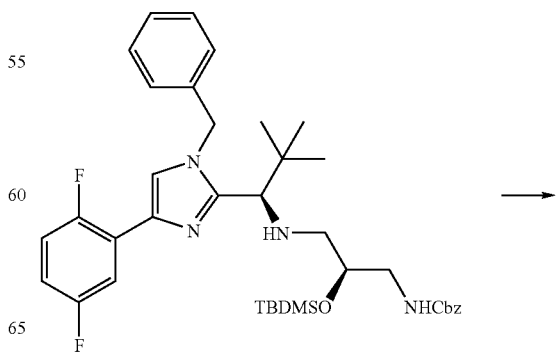

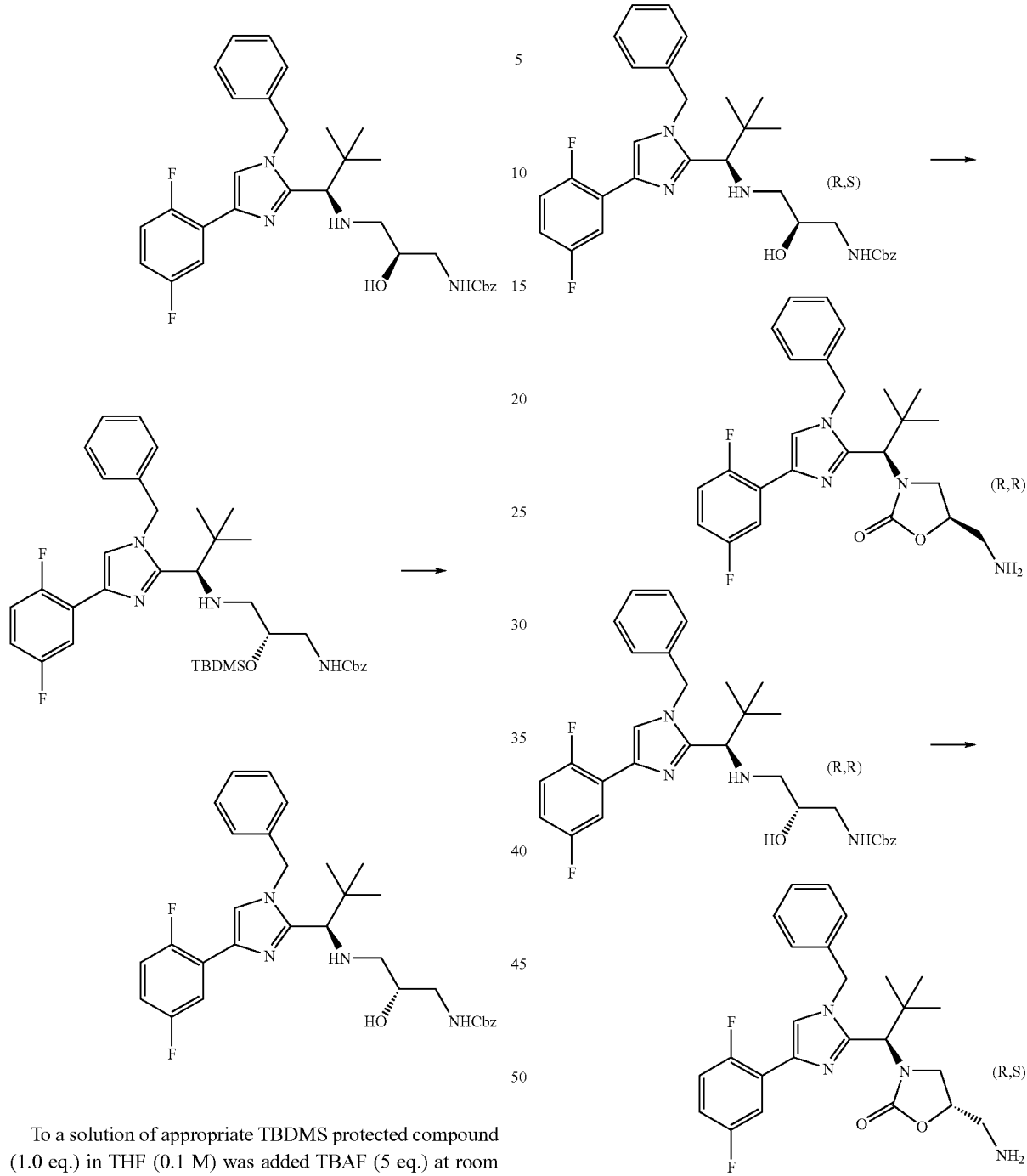

To a solution of appropriate TBDMS protected compound (1.0 eq.) in THF (0.1 M) was added TBAF (5 eq.) at room temperature. The reaction mixture was stirred for 20 h. After quenched with saturated NH$_4$Cl aqueous solution, the reaction mixture was worked up with EtOAc, which was washed with water and brine. The organic layer was separated, dried, and concentrated. The crude product was purified on silica gel with 30-50% EtOAc/Hexanes gradient elution to provide the pure alcohol (benzyl(S)-3-((R)-1-(1-benzyl-4-(2,5-difluorophenyl)-1H-imidazol-2-yl)-2,2-dimethylpropylamino)-2-hydroxypropylcarbamate and benzyl (R)-3-((R)-1-(1-benzyl-4-(2,5-difluorophenyl)-1H-imidazol-2-yl)-2,2-dimethylpropylamino)-2-hydroxypropylcarbamate).

To a solution of appropriate alcohol (1.0 eq.) in dichloromethane (0.3 M) was sequentially added triphosgene (1.5 eq.) and triethylamine (2.5 eq.) at room temperature. After stirred for 1 h, the reaction mixture was quenched with saturated NaHCO$_3$ aqueous solution and worked up with dichloromethane. The organic layer was separated, dried, and concentrated. The crude product was dissolved in acetonitrile (0.1 M) followed by addition of iodotrimethylsilane (10 eq.). After stirred for 1 h, the reaction mixture was quenched with aqueous Na$_2$S$_2$O$_3$ solution and worked up with EtOAc. The organic layer was separated, dried, and concentrated. The resulting oil was purified by reverse phase HPLC and lyophilized to provide the desired compound as a TFA salt.

(R)-5-(aminomethyl)-3-((R)-1-(1-benzyl-4-(2,5-difluorophenyl)-1H-imidazol-2-yl)-2,2-dimethylpropyl)oxazolidin-2-one, LCMS (m/z): 455.2 (MH$^+$); LC R$_t$=3.66 min (S)-5-(aminomethyl)-3-((R)-1-(1-benzyl-4-(2,5-difluorophenyl)-1H-imidazol-2-yl)-2,2-dimethylpropyl)oxazolidin-2-one, LCMS (m/z): 455.1 (MH$^+$); LC R$_t$=3.68 min Example 27

Assay for Determining KSP Activity

This example provides a representative in vitro assay for determining KSP activity in vitro. Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM MgCl$_2$, 10 mM DTT and 0.25 mg/mL BSA) to a final concentration of 35 μg/mL microtubules and 45 nM KSP. The microtubule/KSP mixture was then pre-incubated at 37° C. for 10 min to promote the binding of KSP to microtubules.

To each well of the testing plate (384-well plate) containing 1.25 μL of inhibitor or test compound in DMSO (or DMSO only in the case of controls) were added 25 μL of ATP solution (ATP diluted to a concentration of 300 μM in assay buffer) and 25 μL of the above-described microtubule/KSP solution. The plates were incubated at RT for 1 hour. Following incubation, 65 μL of Biomol Green (a malachite green-based dye that detects the release of inorganic phosphate) was added to each well. The plates were incubated for an additional 5-10 minutes then the absorbance at 630 nm was determined using a Victor II plate reader. The amount of absorbance at 630 nm corresponded to the amount of KSP activity in the samples. The IC$_{50}$ of each inhibitor or test compound was then determined based on the decrease in absorbance at 630 nm at each concentration, via nonlinear regression using either XLFit for Excel or Prism data analysis software by GraphPad Software Inc.

Preferred compounds of the invention have a biological activity as measured by an IC$_{50}$ of less than about 1 mM in the assay described in this example with preferred embodiments having biological activity of less than about 25 μM, with particularly preferred embodiments having biological activity of less than about 1000 nM, and with the most preferred embodiments having biological activity of less than about 100 nM.

Example 28

Inhibition of Cellular Proliferation in Tumor Cell Lines Treated with KSP Inhibitors Cells are plated in 96-well plates at densities of about 500 cells per well of a 96-well plate and are allowed to grow for 24 hours. The cells are then treated with various concentrations of compounds for 72 hours. Then, 100 μl of CellTiter Glo is added. CellTiter Glo is a tetrazolium-based assay using the reagent 3-(4,5-dimethylthiazol-2-yl) 5-(3-carboxymethoxyphenyl)-2-(4-sulfophenyl)-2H-tetrazolium (MTS) (U.S. Pat. No. 5,185,450) (see Promega product catalog #G3580, CellTiter 96 Aqueous One Solution Cell Proliferation Assay).

The cells are then incubated in the dark for 30 minutes. The amount of luminescence is determined for each well using a Walloc Trilux plate reader, which correlates with the number of cells per well. The number of viable cells in the wells that receive only DMSO (0.5%) serve as an indication of 0% inhibition, while wells without cells serve as 100% inhibition of cell growth. The compound concentration that results in a 50% growth inhibition (GI$_{50}$) is determined graphically from sigmoidal dose-response curves of log-transformed dose values versus cell counts (percent of control) at 72 hours of continuous compound exposure.

The cell lines used are listed below.

The cell proliferation assay is performed as described above.

| Cancer Cell Lines |
| --- |
| Colo 205 - colon carcinoma |
| RPMI 1640 + 10% FBS + 1% L-glutamine + 1% P/S + 1% |
| NaPyr. + Hepes + 4.5 g/L Glucose + 1% NaBicarb. |
| MDA 435- breast cancer- high met |
| EMEM + 10% FBS + 1% P/S + 1% L-Glutamine + 1% |
| NEAA + 1% NaPyr + 1% vitamins |
| HCT-15 and HCT116 -colon carcinoma |
| RPMI 1640 + 10% FBS + 1% L-glutamine + 1% P/S |
| Drug Resistant Cell Lines |
| KB3.1- colon epidermal carcinoma; parental cell line |
| Iscove's + 10% FBS + 1% L-glutamine + 1% P/S |
| KBV1 - p-glycoprotein associated multi-drug resistant |
| cell line |
| RPMI 1640 + 10% FBS + 1% L-glutamine + 1% P/S + 0.2 |
| ug/mL |
| Vinblastine |
| KB85 - p-glycoprotein associated multi-drug resistant |
| cell line |
| DMEM + 10% FBS + 1% L-glutamine + 1% P/S + 10 ng/mL |
| Colchicine |

Preferred compounds of the invention have a biological activity as measured by an GI$_{50}$ of less than about 1 mM in assay protocols described with some embodiments having biological activity of less than about 25 μM, with other embodiments having biological activity of less than about 1000 nM, and with still other embodiment having a GI$_{50}$ of less than about 100 nM.

Table 2 shows the activity of selected compounds listed in Table 1 as measured according to the assays described in Examples 27 and 28. A "+" indicates that the compound has an IC$_{50}$ or GI$_{50}$ of greater than 1 μM in the assay indicated; a "++" indicates that the compound has an IC$_{50}$ or GI$_{50}$ of less than or equal to 1 μM and greater than 100 nM in the assay indicated; a "+++" indicates that the compound has an IC$_{50}$ or GI$_{50}$ of less than or equal to 100 nM in the assay indicated.

TABLE 2

| Compound | Biochemical Activity IC$_{50}$ | Cell Base Activity GI$_{50}$ | | | |
| --- | --- | --- | --- | --- | --- |
| | | HCT-15 | HCT-116 | KB3.1 | KB8.5 |
| 1 | ++ | + | ++ | ++ | + |
| 3 | ++ | + | + | + | + |
| 4 | ++ | | | + | + |
| 5 | +++ | | | ++ | ++ |

TABLE 2-continued

| Compound | Biochemical Activity IC$_{50}$ | HCT-15 | HCT-116 | KB3.1 | KB8.5 |
|---|---|---|---|---|---|
| 6 | ++ | + | ++ | ++ | + |
| 7 | +++ | ++ | ++ | ++ | ++ |
| 8 | + | | | | |
| 9 | + | ++ | ++ | ++ | + |
| 10 | ++ | | | | |
| 11 | ++ | | | | |
| 12 | + | | | | |
| 14 | + | + | + | + | + |
| 15 | ++ | + | + | + | + |
| 16 | +++ | + | ++ | ++ | + |
| 17 | +++ | + | + | + | + |
| 18 | +++ | ++ | ++ | ++ | + |
| 19 | ++ | | | + | + |
| 20 | ++ | + | ++ | ++ | + |
| 21 | +++ | | | +++ | + |
| 22 | ++ | | | + | + |
| 23 | ++ | + | ++ | + | ++ |
| 24 | +++ | | | ++ | ++ |
| 25 | +++ | ++ | +++ | +++ | ++ |
| 26 | +++ | | ++ | ++ | ++ |
| 27 | +++ | ++ | +++ | +++ | +++ |
| 28 | +++ | +++ | +++ | +++ | +++ |
| 29 | +++ | ++ | ++ | ++ | ++ |
| 30 | +++ | | | | |
| 31 | ++ | | | | |
| 32 | ++ | | | + | + |

Example 29

Clonogenic Softagar Assay Protocol

Human cancer cells are plated at a density of 3×10$^5$ cells per well in a 6-well plate. The next day, a compound of interest at a certain concentration is added to each well. After 24 and 48 hours of incubation, the cells are harvested washed and counted. The following steps are performed using the Multimek 96 robot. Then, 500 viable cells per well are plated in a 96-well plate that is coated with PolyHema to prevent attachment of the cells to the bottom of the well. Agarose (3% stock) is melted, diluted in warmed media and added to the cells to a final concentration of 0.5%. After the soft agar solidified, the plates are incubated at 37° C. for 6 days. Alamar blue dye is added to cells and plates are incubated for an additional 6 hours. The optical density change is measured on a Tecan plate reader and is considered to correlate with the number of colonies formed in soft agar. A cancerous cell is able to grow on the agar and thus will show an increase in optical density. A reading of decreased optical density means that the cancer cells are being inhibited. It is contemplated that compounds of this invention will exhibit a decrease in optical density.

What is claimed is:

1. A compound of Formula (I):

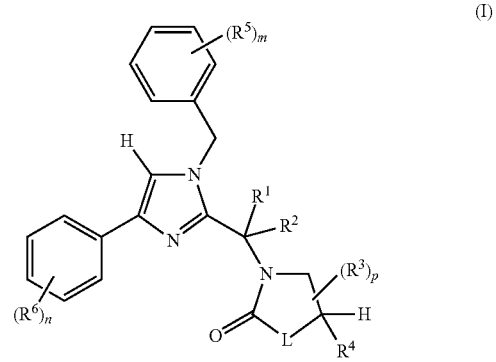

or a pharmaceutically acceptable salt thereof, wherein:
R$^1$ is selected from the group consisting of alkyl and substituted alkyl;
R$^2$ is selected from the group consisting of hydrogen, alkyl, and substituted alkyl;
L is selected from the group consisting of
a) —O—;
b) —OCH$_2$—, —CH$_2$O—, —C(O)NR$^7$—;
c) —CH$_2$OCH$_2$—, —CH$_2$NR$^7$CH$_2$—, —CH$_2$CH$_2$O—, —C(O)NR$^7$CH$_2$—, and —CH$_2$CH$_2$NR$^7$—;
R$^3$ and R$^4$ are independently selected from the group consisting of halo, alkyl, and substituted alkyl;
R$^5$ and R$^6$ are independently selected from the group consisting of cyano, alkyl, substituted alkyl, alkoxy, substituted alkoxy, halo, and hydroxy;
R$^7$ is selected from the group consisting of hydrogen, alkyl, and —SO$_2$alkyl;
m is 0, 1, 2, or 3;
n is 0, 1, 2, or 3; and
p is 0 or 1.

2. A compound of claim 1 wherein R$^1$ and R$^2$ are alkyl.

3. A compound of claim 1 wherein R$^1$ is alkyl and R$^2$ is hydrogen.

4. A compound of claim 3 wherein R$^1$ is selected from the group consisting of isopropyl, t-butyl, and propyl.

5. A compound of claim 1 wherein R$^4$ is substituted alkyl.

6. A compound of claim 5 wherein R$^4$ is alkyl substituted with 1 to 5 substituents selected from the group consisting of amino, substituted amino, halo, alkoxy, substituted alkoxy, and hydroxy.

7. A compound of claim 1 wherein R$^4$ is selected from the group consisting of halo, —CH$_2$NH$_2$, —(CH$_2$)$_2$NH$_2$, —(CH$_2$)$_3$NH$_2$, and —CH$_2$OH.

8. A compound of claim 1 wherein m is 0.

9. A compound of claim 1 wherein R$^6$ is halo.

10. A compound of claim 1 wherein R$^6$ and the phenyl ring to which it is attached is selected from the group consisting of phenyl, 3-bromophenyl, 3-chlorophenyl, 4-cyanophenyl, 2,5-difluorophenyl, 3-fluorophenyl, 2-methoxyphenyl, 3-methoxyphenyl, 4-methoxyphenyl, 4-methylphenyl, 2-trifluoromethylphenyl, and 3-trifluoromethylphenyl.

11. A compound of claim 1, wherein L and the atoms to which it is joined form a ring selected from the group consisting of

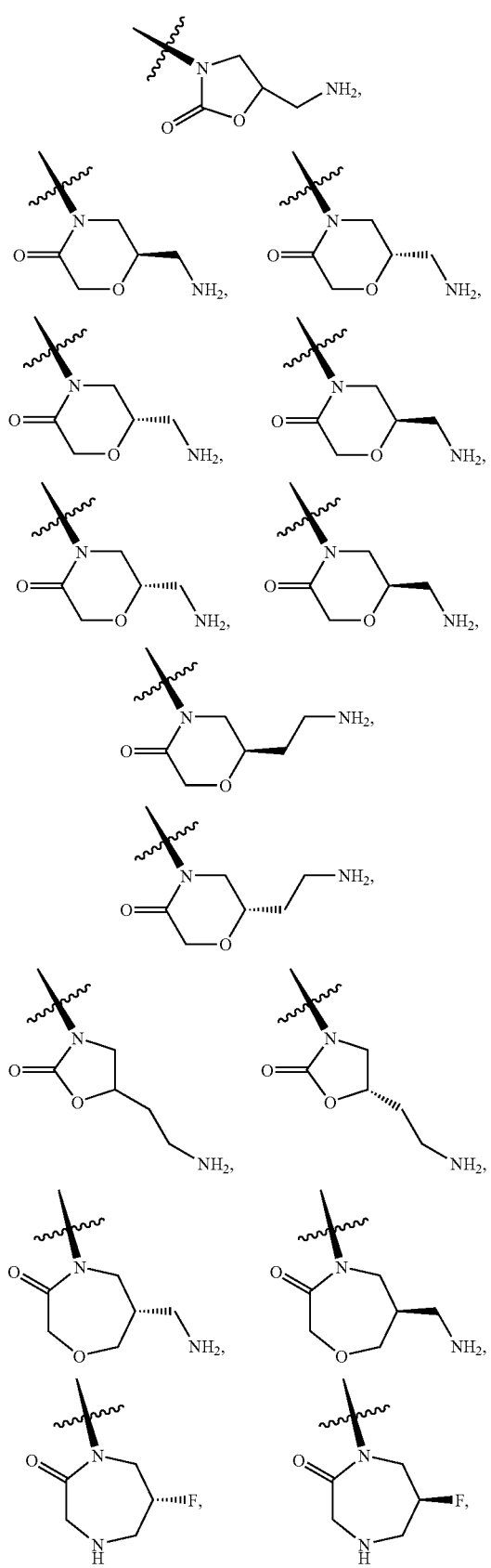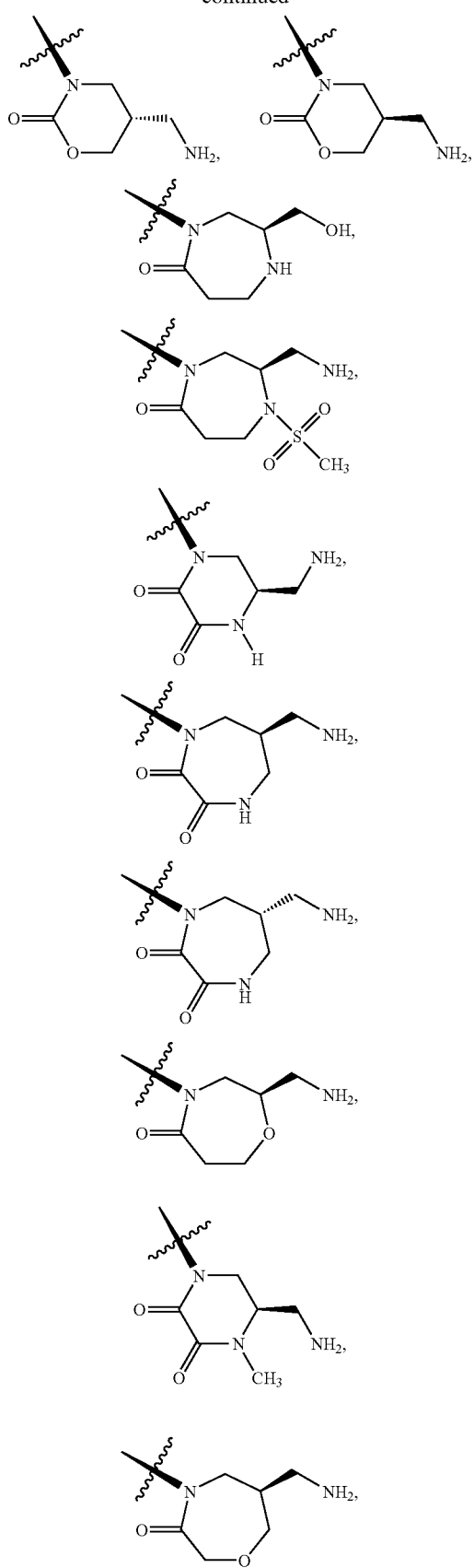

-continued
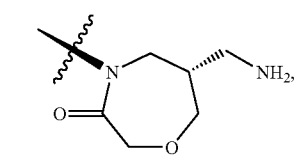
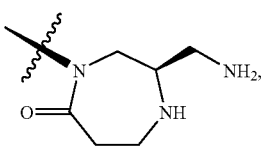
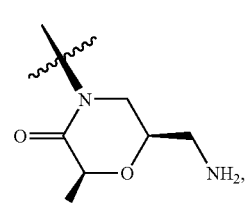
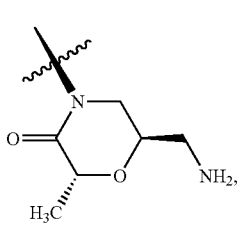
and
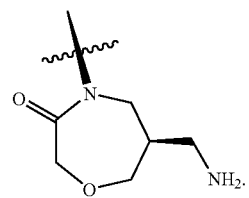
12. A compound of claim 1 having Formula (Ia) or a pharmaceutically acceptable salt thereof:
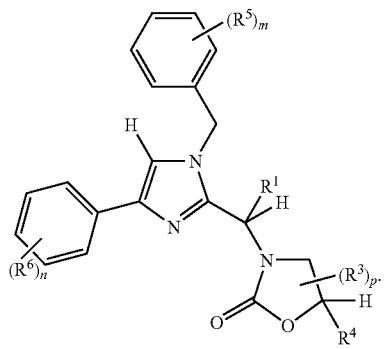
13. A compound of claim 1 having Formula (Ib)-(Id) or a pharmaceutically acceptable salt thereof:
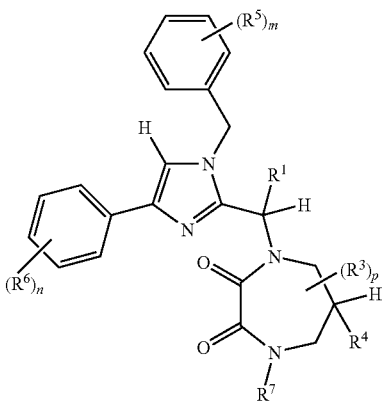
14. A compound of claim 1 having Formula (Ie)-(Ii) or a pharmaceutically acceptable salt thereof:

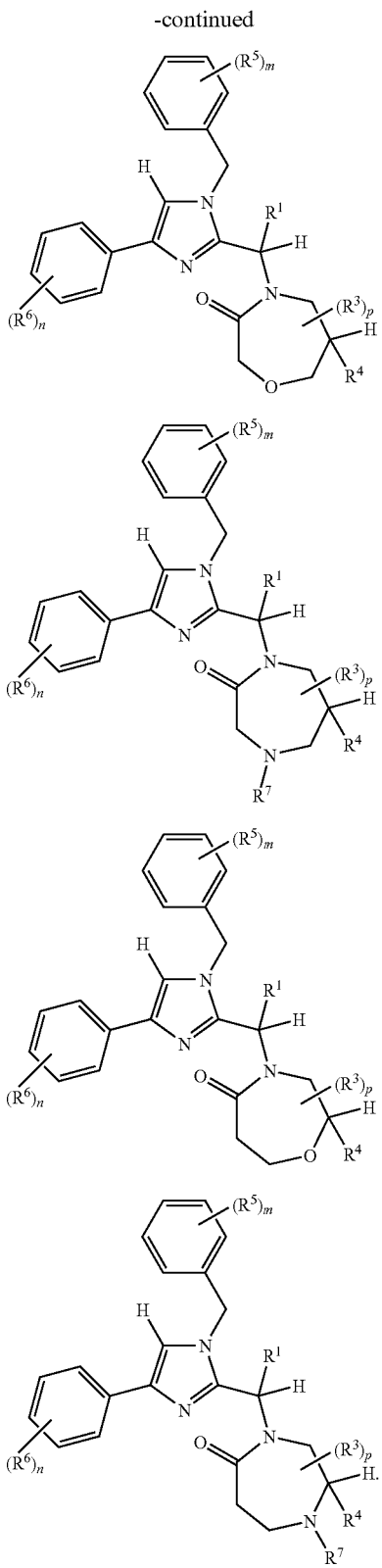

15. A compound that is (S)-5-(aminomethyl)-3-((R)-1-(1-benzyl-4-(2,5-difluorophenyl)-1H-imidazol-2-yl)-2,2-dimethylpropyl)oxazolidin-2-one or a pharmaceutically acceptable salt thereof:

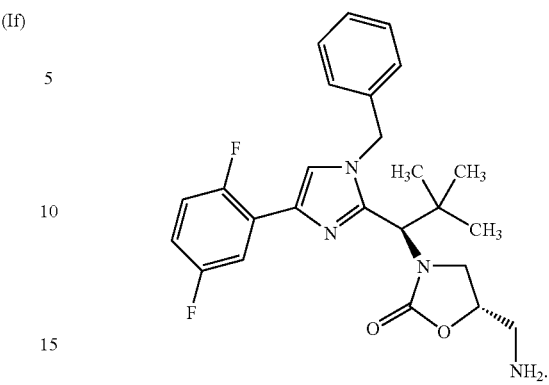

16. A compound that is (R)-5-(aminomethyl)-3-((R)-1-(1-benzyl-4-(2,5-difluorophenyl)-1H-imidazol-2-yl)-2,2-dimethylpropyl)oxazolidin-2-one or a pharmaceutically acceptable salt thereof:

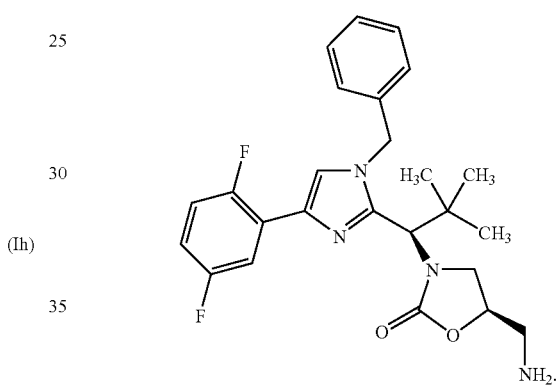

17. A compound claim 1 selected from:
- (5R)-5-(2-aminoethyl)-3-[(1R)-1-(1-benzyl-4-phenyl-1H-imidazol-2-yl)-2,2-dimethylpropyl]-1,3-oxazolidin-2-one;
- (5S)-5-(2-aminoethyl)-3-[(1R)-1-(1-benzyl-4-phenyl-1H-imidazol-2-yl)-2,2-dimethylpropyl]-1,3-oxazolidin-2-one;
- 5-(aminomethyl)-3-{(1R)-1-[1-benzyl-4-(3-chlorophenyl)-1H-imidazol-2-yl]-2-methylpropyl}-1,3-oxazolidin-2-one;
- (5S)-5-(aminomethyl)-3-[(1R)-1-(1-benzyl-4-phenyl-1H-imidazol-2-yl)-2,2-dimethylpropyl]-1,3-oxazinan-2-one;
- (5R)-5-(aminomethyl)-3-[(1R)-1-(1-benzyl-4-phenyl-1H-imidazol-2-yl)-2,2-dimethylpropyl]-1,3-oxazinan-2-one;
- (6S)-6-(aminomethyl)-4-[(1R)-1-(1-benzyl-4-phenyl-1H-imidazol-2-yl)-2,2-dimethylpropyl]morpholin-3-one;
- (6R)-6-(aminomethyl)-4-[(1R)-1-(1-benzyl-4-phenyl-1H-imidazol-2-yl)-2,2-dimethylpropyl]morpholin-3-one;
- (6R)-6-(aminomethyl)-4-{(1R)-1-[1-benzyl-4-(3-chlorophenyl)-1H-imidazol-2-yl]-2-methylpropyl}morpholin-3-one;
- (6S)-6-(aminomethyl)-4-{(1R)-1-[1-benzyl-4-(3-chlorophenyl)-1H-imidazol-2-yl]-2-methylpropyl}morpholin-3-one;

(6R)-6-(2-aminoethyl)-4-[(1R)-1-(1-benzyl-4-phenyl-1H-imidazol-2-yl)-2,2-dimethylpropyl]morpholin-3-one;

(6S)-6-(2-aminoethyl)-4-[(1R)-1-(1-benzyl-4-phenyl-1H-imidazol-2-yl)-2,2-dimethylpropyl]morpholin-3-one;

(6S)-6-(2-aminoethyl)-4-{(1R)-1-[1-benzyl-4-(3-chlorophenyl)-1H-imidazol-2-yl]-2-methylpropyl}morpholin-3-one;

(6R)-6-(2-aminoethyl)-4-{(1R)-1-[1-benzyl-4-(3-fluorophenyl)-1H-imidazol-2-yl]-2-methylpropyl}morpholin-3-one;

(2S,6R)-6-(aminomethyl)-4-{(1R)-1-[1-benzyl-4-(3-fluorophenyl)-1H-imidazol-2-yl]-2,2-dimethylpropyl}-2-methylmorpholin-3-one;

(2R,6R)-6-(aminomethyl)-4-{(1R)-1-[1-benzyl-4-(3-fluorophenyl)-1H-imidazol-2-yl]-2,2-dimethylpropyl}-2-methylmorpholin-3-one;

(5R)-5-(aminomethyl)-1-[(1R)-1-(1-benzyl-4-phenyl-1H-imidazol-2-yl)-2,2-dimethylpropyl]piperazine-2,3-dione;

(5S)-5-(aminomethyl)-1-[(1R)-1-(1-benzyl-4-phenyl-1H-imidazol-2-yl)-2,2-dimethylpropyl]piperazine-2,3-dione;

(5R)-5-(aminomethyl)-1-[(1R)-1-(1-benzyl-4-phenyl-1H-imidazol-2-yl)-2,2-dimethylpropyl]-4-methylpiperazine-2,3-dione;

(2S)-4-[(1R)-1-(1-benzyl-4-phenyl-1H-imidazol-2-yl)-2,2-dimethylpropyl]-2-(hydroxymethyl)-1,4-diazepan-5-one;

(2R)-2-(aminomethyl)-4-[(1R)-1-(1-benzyl-4-phenyl-1H-imidazol-2-yl)-2,2-dimethylpropyl]-1,4-diazepan-5-one;

(2R)-2-(aminomethyl)-4-[(1R)-1-(1-benzyl-4-phenyl-1H-imidazol-2-yl)-2,2-dimethylpropyl]-1-(methylsulfonyl)-1,4-diazepan-5-one;

(2S)-2-(aminomethyl)-4-[(1R)-1-(1-benzyl-4-phenyl-1H-imidazol-2-yl)-2,2-dimethylpropyl]-1,4-oxazepan-5-one;

(2R)-2-(aminomethyl)-4-[(1R)-1-(1-benzyl-4-phenyl-1H-imidazol-2-yl)-2,2-dimethylpropyl]-1,4-oxazepan-5-one;

(6S)-6-(aminomethyl)-4-[(1R)-1-(1-benzyl-4-phenyl-1H-imidazol-2-yl)-2,2-dimethylpropyl]-1,4-oxazepan-3-one;

(6R)-6-(aminomethyl)-4-{(1R)-1-(1-benzyl-4-phenyl-1H-imidazol-2-yl)-2,2-dimethylpropyl}-1,4-oxazepan-3-one;

(6R)-6-(aminomethyl)-4-{(1R)-1-[1-(3,5-difluorobenzyl)-4-(3-fluorophenyl)-1H-imidazol-2-yl]-2,2-dimethylpropyl}-1,4-oxazepan-3-one;

(6R)-6-(aminomethyl)-4-{(1R)-1-[1-benzyl-4-(3-fluorophenyl)-1H-imidazol-2-yl]-2,2-dimethylpropyl}-1,4-oxazepan-3-one;

(6R)-6-(aminomethyl)-4-{(1R)-1-[1-(3-fluorobenzyl)-4-(3-fluorophenyl)-1H-imidazol-2-yl]-2,2-dimethylpropyl}-1,4-oxazepan-3-one;

(6S)-6-(aminomethyl)-4-{(1R)-1-[1-(3-fluorobenzyl)-4-(3-fluorophenyl)-1H-imidazol-2-yl]-2,2-dimethylpropyl}-1,4-oxazepan-3-one;

(6S)-6-(aminomethyl)-1-[(1R)-1-(1-benzyl-4-phenyl-1H-imidazol-2-yl)-2,2-dimethylpropyl]-1,4-diazepane-2,3-dione;

(6R)-1-[(1R)-1-(1-benzyl-4-phenyl-1H-imidazol-2-yl)-2,2-dimethylpropyl]-6-fluoro-1,4-diazepan-2-one; or (6S)-1-[(1R)-1-(1-benzyl-4-phenyl-1H-imidazol-2-yl)-2,2-dimethylpropyl]-6-fluoro-1,4-diazepan-2-one;

or a pharmaceutically acceptable salt thereof.

18. A pharmaceutical composition comprising a therapeutically effective amount of a compound of any one of claims 1 to 17 and a pharmaceutically acceptable carrier.

19. The composition of claim 18 further comprising at least one additional agent for the treatment of cancer.

20. The composition of claim 19, wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

* * * * *